US011999929B2

(12) United States Patent
Frank et al.

(10) Patent No.: US 11,999,929 B2
(45) Date of Patent: Jun. 4, 2024

(54) METHODS AND SYSTEMS FOR COATING A CELL GROWTH SURFACE

(71) Applicant: Terumo BCT, Inc., Lakewood, CO (US)

(72) Inventors: Nathan D. Frank, Arvada, CO (US); Brian J. Nankervis, Golden, CO (US); Dennis J. Hlavinka, Arvada, CO (US); Thomas G. Dilorenzo, Arvada, CO (US)

(73) Assignee: Terumo BCT, Inc., Lakewood, CO (US)

( * ) Notice: Subject to any disclaimer, the term of this patent is extended or adjusted under 35 U.S.C. 154(b) by 602 days.

(21) Appl. No.: 16/845,686

(22) Filed: Apr. 10, 2020

(65) Prior Publication Data

US 2020/0239819 A1    Jul. 30, 2020

Related U.S. Application Data

(62) Division of application No. 15/616,635, filed on Jun. 7, 2017, now Pat. No. 11,685,883.

(Continued)

(51) Int. Cl.
*C12M 1/00* (2006.01)
*C12M 1/12* (2006.01)
*C12M 3/06* (2006.01)

(52) U.S. Cl.
CPC .......... *C12M 1/005* (2013.01); *C12M 21/00* (2013.01); *C12M 23/06* (2013.01); *C12M 23/16* (2013.01);

(Continued)

(58) Field of Classification Search
CPC .......... C12M 1/005; C12M 1/00; C12M 1/36; C12M 21/00; C12N 5/071
See application file for complete search history.

(56) References Cited

U.S. PATENT DOCUMENTS

| 2,997,077 A | 8/1961 | Rodrigues |
| 3,013,435 A | 12/1961 | Rodrigues |

(Continued)

FOREIGN PATENT DOCUMENTS

| CA | 1016332 A | 8/1977 |
| DE | 4007703 A1 | 9/1991 |

(Continued)

OTHER PUBLICATIONS

Chang et al., "Membrane Bioreactors: Present and Prospects", Advances in Biochemical Engineering, 1991, pp. 27-64, vol. 44.

(Continued)

*Primary Examiner* — Dah-Wei D. Yuan
*Assistant Examiner* — Andrew J Bowman
(74) *Attorney, Agent, or Firm* — Harness, Dickey & Pierce, P.L.C.

(57) ABSTRACT

Embodiments described herein generally provide for the expansion of cells in a cell expansion system using an active promotion of a coating agent(s) to a cell growth surface. A coating agent may be applied to a surface, such as the cell growth surface of a hollow fiber, by controlling the movement of a fluid in which a coating agent is suspended. Using ultrafiltration, the fluid may be pushed through the pores of a hollow fiber from a first side, e.g., an intracapillary (IC) side, of the hollow fiber to a second side, e.g., an extracapillary (EC) side, while the coating agent is actively promoted to the surface of the hollow fiber. In so doing, the coating agent may be hydrostatically deposited onto a wall, e.g., inner wall, of the hollow fiber.

15 Claims, 19 Drawing Sheets

Related U.S. Application Data

(60) Provisional application No. 62/347,025, filed on Jun. 7, 2016.

(52) U.S. Cl.
CPC ............. *C12M 23/20* (2013.01); *C12M 25/02* (2013.01); *C12M 25/12* (2013.01); *C12M 29/04* (2013.01); *C12M 29/18* (2013.01)

(56) References Cited

U.S. PATENT DOCUMENTS

| | | |
|---|---|---|
| 3,067,915 A | 12/1962 | Shapiro et al. |
| 3,191,807 A | 6/1965 | Rodrigues |
| 3,283,727 A | 11/1966 | Rodrigues |
| 3,701,717 A | 10/1972 | Ingvorsen |
| 3,821,087 A | 6/1974 | Knazek et al. |
| 3,896,061 A | 7/1975 | Tanzawa et al. |
| 4,173,415 A | 11/1979 | Wyatt |
| 4,301,010 A | 11/1981 | Eddleman et al. |
| 4,301,118 A | 11/1981 | Eddleman et al. |
| 4,391,912 A | 7/1983 | Yoshida et al. |
| 4,412,990 A | 11/1983 | Lundblad et al. |
| 4,418,691 A | 12/1983 | Yannas et al. |
| 4,439,322 A | 3/1984 | Sonoda et al. |
| 4,439,901 A | 4/1984 | Eddleman |
| 4,478,829 A | 10/1984 | Landaburu et al. |
| 4,486,188 A | 12/1984 | Altshuler et al. |
| 4,509,695 A | 4/1985 | Bessman |
| 4,585,654 A | 4/1986 | Landaburu et al. |
| 4,618,586 A | 10/1986 | Walker et al. |
| 4,629,686 A | 12/1986 | Gruenberg |
| 4,647,539 A | 3/1987 | Bach |
| 4,650,766 A | 3/1987 | Harm et al. |
| 4,670,544 A | 6/1987 | Schwinn et al. |
| 4,705,918 A | 11/1987 | Harmon |
| 4,722,902 A | 2/1988 | Harm et al. |
| 4,727,059 A | 2/1988 | Binder et al. |
| 4,804,628 A | 2/1989 | Cracauer et al. |
| 4,828,706 A | 5/1989 | Eddleman |
| 4,885,087 A | 12/1989 | Kopf |
| 4,889,812 A | 12/1989 | Guinn et al. |
| 4,894,342 A | 1/1990 | Guinn et al. |
| 4,897,358 A | 1/1990 | Carrasco |
| 4,918,019 A | 4/1990 | Guinn |
| 4,940,541 A | 7/1990 | Aoyagi |
| 4,960,521 A | 10/1990 | Keller |
| 4,973,558 A | 11/1990 | Wilson et al. |
| 4,988,623 A | 1/1991 | Schwarz et al. |
| 5,015,585 A | 5/1991 | Robinson |
| 5,019,054 A | 5/1991 | Clement et al. |
| 5,079,168 A | 1/1992 | Amiot |
| 5,126,238 A | 6/1992 | Gebhard et al. |
| 5,130,141 A | 7/1992 | Law et al. |
| 5,149,544 A | 9/1992 | Gentile et al. |
| 5,162,225 A | 11/1992 | Sager et al. |
| 5,169,930 A | 12/1992 | Ruoslahti et al. |
| 5,192,553 A | 3/1993 | Boyse et al. |
| 5,197,985 A | 3/1993 | Caplan et al. |
| 5,202,254 A | 4/1993 | Amiot |
| 5,225,346 A | 7/1993 | Matsumiya et al. |
| 5,226,914 A | 7/1993 | Caplan et al. |
| 5,240,614 A | 8/1993 | Ofsthun et al. |
| 5,240,861 A | 8/1993 | Bieri |
| 5,283,058 A | 2/1994 | Faustman |
| 5,310,676 A | 5/1994 | Johansson et al. |
| 5,324,428 A | 6/1994 | Flaherty |
| 5,330,915 A | 7/1994 | Wilson et al. |
| 5,342,752 A | 8/1994 | Platz et al. |
| 5,399,493 A | 3/1995 | Emerson et al. |
| 5,416,022 A | 5/1995 | Amiot |
| 5,422,197 A | 6/1995 | Zito |
| 5,436,151 A | 7/1995 | McGlave et al. |
| 5,437,994 A | 8/1995 | Emerson et al. |
| 5,439,757 A | 8/1995 | Zito |
| 5,459,069 A | 10/1995 | Palsson et al. |
| 5,460,964 A | 10/1995 | McGlave et al. |
| H1509 H | 12/1995 | Eran et al. |
| 5,478,739 A | 12/1995 | Slivka et al. |
| 5,486,359 A | 1/1996 | Caplan et al. |
| 5,496,659 A | 3/1996 | Zito |
| 5,507,949 A | 4/1996 | Ho |
| 5,510,257 A | 4/1996 | Sirkar et al. |
| 5,512,180 A | 4/1996 | Ho |
| 5,527,467 A | 6/1996 | Ofsthun et al. |
| 5,541,105 A | 7/1996 | Melink et al. |
| 5,543,316 A | 8/1996 | Zawadzka et al. |
| 5,545,492 A | 8/1996 | Zito |
| 5,549,674 A | 8/1996 | Humes et al. |
| 5,571,720 A | 11/1996 | Grandics et al. |
| 5,591,625 A | 1/1997 | Gerson et al. |
| 5,593,580 A | 1/1997 | Kopf |
| 5,595,909 A | 1/1997 | Hu et al. |
| 5,599,703 A | 2/1997 | Davis et al. |
| 5,605,822 A | 2/1997 | Emerson et al. |
| 5,605,829 A | 2/1997 | McGlave et al. |
| 5,605,835 A | 2/1997 | Hu et al. |
| 5,622,857 A | 4/1997 | Goffe |
| 5,626,731 A | 5/1997 | Cooley et al. |
| 5,627,070 A | 5/1997 | Gruenberg |
| 5,631,006 A | 5/1997 | Melink et al. |
| 5,635,386 A | 6/1997 | Palsson et al. |
| 5,635,387 A | 6/1997 | Fei et al. |
| 5,643,736 A | 7/1997 | Bruder et al. |
| 5,643,794 A | 7/1997 | Liu et al. |
| 5,646,043 A | 7/1997 | Emerson et al. |
| 5,654,186 A | 8/1997 | Cerami et al. |
| 5,656,421 A | 8/1997 | Gebhard et al. |
| 5,658,995 A | 8/1997 | Kohn et al. |
| 5,667,985 A | 9/1997 | O'Leary et al. |
| 5,670,147 A | 9/1997 | Emerson et al. |
| 5,670,351 A | 9/1997 | Emerson et al. |
| 5,674,750 A | 10/1997 | Kraus et al. |
| 5,684,712 A | 11/1997 | Goffe et al. |
| 5,686,289 A | 11/1997 | Humes et al. |
| 5,688,687 A | 11/1997 | Palsson et al. |
| 5,695,989 A | 12/1997 | Kalamasz |
| 5,700,289 A | 12/1997 | Breitbart et al. |
| 5,705,534 A | 1/1998 | D'Agostino et al. |
| 5,707,859 A | 1/1998 | Miller et al. |
| 5,712,163 A | 1/1998 | Parenteau et al. |
| 5,728,581 A | 3/1998 | Schwartz et al. |
| 5,733,541 A | 3/1998 | Taichman et al. |
| 5,733,542 A | 3/1998 | Haynesworth et al. |
| 5,736,396 A | 4/1998 | Bruder et al. |
| 5,744,347 A | 4/1998 | Wagner et al. |
| 5,750,651 A | 5/1998 | Oppermann et al. |
| 5,753,506 A | 5/1998 | Johe |
| 5,763,194 A | 6/1998 | Slowiaczek et al. |
| 5,763,197 A | 6/1998 | Tsukamoto et al. |
| 5,763,261 A | 6/1998 | Gruenberg |
| 5,763,266 A | 6/1998 | Palsson et al. |
| 5,766,944 A | 6/1998 | Ruiz |
| 5,772,994 A | 6/1998 | Ildstad et al. |
| 5,783,075 A | 7/1998 | Eddleman et al. |
| 5,783,216 A | 7/1998 | Faustman |
| 5,785,912 A | 7/1998 | Cooley et al. |
| 5,804,446 A | 9/1998 | Cerami et al. |
| 5,806,529 A | 9/1998 | Reisner et al. |
| 5,807,686 A | 9/1998 | Wagner et al. |
| 5,811,094 A | 9/1998 | Caplan et al. |
| 5,811,397 A | 9/1998 | Francavilla et al. |
| 5,817,773 A | 10/1998 | Wilson et al. |
| 5,821,218 A | 10/1998 | Toback et al. |
| 5,827,735 A | 10/1998 | Young et al. |
| 5,827,740 A | 10/1998 | Pittenger |
| 5,830,921 A | 11/1998 | Cooley et al. |
| 5,833,979 A | 11/1998 | Schinstine et al. |
| 5,837,258 A | 11/1998 | Grotendorst |
| 5,837,539 A | 11/1998 | Caplan et al. |
| 5,840,502 A | 11/1998 | Van Vlasselaer |
| 5,840,576 A | 11/1998 | Schinstine et al. |
| 5,840,580 A | 11/1998 | Terstappen et al. |
| 5,842,477 A | 12/1998 | Naughton et al. |

(56) References Cited

U.S. PATENT DOCUMENTS

| | | |
|---|---|---|
| 5,843,633 A | 12/1998 | Yin et al. |
| 5,846,796 A | 12/1998 | Cerami et al. |
| 5,853,247 A | 12/1998 | Shroyer |
| 5,853,717 A | 12/1998 | Schinstine et al. |
| 5,855,608 A | 1/1999 | Brekke et al. |
| 5,855,613 A | 1/1999 | Antanavich et al. |
| 5,855,619 A | 1/1999 | Caplan et al. |
| 5,858,747 A | 1/1999 | Schinstine et al. |
| 5,858,782 A | 1/1999 | Long et al. |
| 5,861,315 A | 1/1999 | Nakahata |
| 5,866,115 A | 2/1999 | Kanz et al. |
| 5,866,420 A | 2/1999 | Talbot et al. |
| 5,868,930 A | 2/1999 | Kopf |
| 5,882,295 A | 3/1999 | Kope |
| 5,882,918 A | 3/1999 | Goffe |
| 5,882,929 A | 3/1999 | Fofonoff et al. |
| 5,888,807 A | 3/1999 | Palsson et al. |
| 5,902,741 A | 5/1999 | Purchio et al. |
| 5,906,827 A | 5/1999 | Khouri et al. |
| 5,906,934 A | 5/1999 | Grande et al. |
| 5,908,782 A | 6/1999 | Marshak et al. |
| 5,908,784 A | 6/1999 | Johnstone et al. |
| 5,912,177 A | 6/1999 | Turner et al. |
| 5,914,108 A | 6/1999 | Tsukamoto et al. |
| 5,922,597 A | 7/1999 | Verfaillie et al. |
| 5,922,847 A | 7/1999 | Broudy et al. |
| 5,925,567 A | 7/1999 | Kraus et al. |
| 5,928,945 A | 7/1999 | Seliktar et al. |
| 5,935,849 A | 8/1999 | Schinstine et al. |
| 5,938,929 A | 8/1999 | Shimagaki et al. |
| 5,939,323 A | 8/1999 | Valentini et al. |
| 5,942,225 A | 8/1999 | Bruder et al. |
| 5,955,353 A | 9/1999 | Amiot |
| 5,958,763 A | 9/1999 | Goffe |
| 5,965,436 A | 10/1999 | Thiede et al. |
| 5,972,703 A | 10/1999 | Long et al. |
| 5,980,795 A | 11/1999 | Klotzer et al. |
| 5,981,211 A | 11/1999 | Hu et al. |
| 5,981,708 A | 11/1999 | Lawman et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,001,643 A | 12/1999 | Spaulding |
| 6,001,647 A | 12/1999 | Peck et al. |
| 6,004,743 A | 12/1999 | Kenyon et al. |
| 6,010,696 A | 1/2000 | Caplan et al. |
| 6,015,554 A | 1/2000 | Galy |
| 6,022,540 A | 2/2000 | Bruder et al. |
| 6,022,742 A | 2/2000 | Kopf |
| 6,022,743 A | 2/2000 | Naughton et al. |
| 6,027,743 A | 2/2000 | Khouri et al. |
| 6,030,836 A | 2/2000 | Thiede et al. |
| 6,040,180 A | 3/2000 | Johe |
| 6,045,818 A | 4/2000 | Cima et al. |
| 6,048,721 A | 4/2000 | Armstrong et al. |
| 6,048,727 A | 4/2000 | Kopf |
| 6,049,026 A | 4/2000 | Muschler |
| 6,054,121 A | 4/2000 | Cerami et al. |
| 6,060,270 A | 5/2000 | Humes |
| 6,066,317 A | 5/2000 | Yang et al. |
| 6,071,691 A | 6/2000 | Hoekstra et al. |
| 6,074,366 A | 6/2000 | Rogers et al. |
| 6,082,364 A | 7/2000 | Balian et al. |
| 6,083,747 A | 7/2000 | Wong et al. |
| 6,086,643 A | 7/2000 | Clark et al. |
| 6,087,113 A | 7/2000 | Caplan et al. |
| 6,096,532 A | 8/2000 | Armstrong et al. |
| 6,096,537 A | 8/2000 | Chappel |
| 6,103,117 A | 8/2000 | Shimagaki et al. |
| 6,103,522 A | 8/2000 | Torok-Storb et al. |
| 6,110,176 A | 8/2000 | Shapira |
| 6,110,482 A | 8/2000 | Khouri et al. |
| 6,114,307 A | 9/2000 | Jaspers et al. |
| 6,117,985 A | 9/2000 | Thomas et al. |
| 6,120,491 A | 9/2000 | Kohn et al. |
| 6,127,141 A | 10/2000 | Kopf |
| 6,129,911 A | 10/2000 | Faris |
| 6,143,293 A | 11/2000 | Weiss et al. |
| 6,146,360 A | 11/2000 | Rogers et al. |
| 6,146,888 A | 11/2000 | Smith et al. |
| 6,149,902 A | 11/2000 | Artavanis-Tsakonas et al. |
| 6,149,906 A | 11/2000 | Mosca |
| 6,150,164 A | 11/2000 | Humes |
| 6,152,964 A | 11/2000 | Van Blitterswijk et al. |
| 6,162,643 A | 12/2000 | Wille, Jr. |
| 6,165,225 A | 12/2000 | Antanavich et al. |
| 6,165,785 A | 12/2000 | Ogle et al. |
| 6,174,333 B1 | 1/2001 | Kadiyala et al. |
| 6,174,526 B1 | 1/2001 | Cerami et al. |
| 6,174,666 B1 | 1/2001 | Pavlakis et al. |
| 6,179,871 B1 | 1/2001 | Halpern |
| 6,197,325 B1 | 3/2001 | MacPhee et al. |
| 6,197,575 B1 | 3/2001 | Griffith et al. |
| 6,200,606 B1 | 3/2001 | Peterson et al. |
| 6,214,369 B1 | 4/2001 | Grande et al. |
| 6,214,574 B1 | 4/2001 | Kopf |
| 6,224,860 B1 | 5/2001 | Brown |
| 6,225,119 B1 | 5/2001 | Qasba et al. |
| 6,225,368 B1 | 5/2001 | D'Agostino et al. |
| 6,228,117 B1 | 5/2001 | De Bruijn et al. |
| 6,228,607 B1 | 5/2001 | Kersten et al. |
| 6,228,635 B1 | 5/2001 | Armstrong et al. |
| 6,238,908 B1 | 5/2001 | Armstrong et al. |
| 6,239,157 B1 | 5/2001 | Mbalaviele |
| 6,242,252 B1 | 6/2001 | Reid et al. |
| 6,248,319 B1 | 6/2001 | Zsebo et al. |
| 6,248,587 B1 | 6/2001 | Rodgers et al. |
| 6,255,112 B1 | 7/2001 | Thiede et al. |
| 6,258,597 B1 | 7/2001 | Bachovchin et al. |
| 6,258,778 B1 | 7/2001 | Rodgers et al. |
| 6,261,549 B1 | 7/2001 | Fernandez et al. |
| 6,280,718 B1 | 8/2001 | Kaufman et al. |
| 6,280,724 B1 | 8/2001 | Moore |
| 6,281,012 B1 | 8/2001 | McIntosh et al. |
| 6,281,195 B1 | 8/2001 | Rueger et al. |
| 6,287,864 B1 | 9/2001 | Bagnis et al. |
| 6,291,249 B1 | 9/2001 | Mahant et al. |
| 6,297,213 B1 | 10/2001 | Oppermann et al. |
| 6,299,650 B1 | 10/2001 | Van Blitterswijk et al. |
| 6,306,424 B1 | 10/2001 | Vyakarnam et al. |
| 6,306,575 B1 | 10/2001 | Thomas et al. |
| 6,322,784 B1 | 11/2001 | Pittenger et al. |
| 6,322,786 B1 | 11/2001 | Anderson |
| 6,326,198 B1 | 12/2001 | Emerson et al. |
| 6,326,201 B1 | 12/2001 | Fung et al. |
| 6,328,765 B1 | 12/2001 | Hardwick et al. |
| 6,328,960 B1 | 12/2001 | McIntosh et al. |
| 6,333,029 B1 | 12/2001 | Vyakarnam et al. |
| 6,335,195 B1 | 1/2002 | Rodgers et al. |
| 6,338,942 B2 | 1/2002 | Kraus et al. |
| 6,340,592 B1 | 1/2002 | Stringer |
| 6,342,370 B1 | 1/2002 | Connolly et al. |
| 6,372,495 B1 | 1/2002 | Flendrig |
| 6,355,239 B1 | 3/2002 | Bruder et al. |
| 6,358,252 B1 | 3/2002 | Shapira |
| 6,361,997 B1 | 3/2002 | Huss |
| 6,365,149 B2 | 4/2002 | Vyakarnam et al. |
| 6,368,636 B1 | 4/2002 | McIntosh et al. |
| 6,372,210 B2 | 4/2002 | Brown |
| 6,372,244 B1 | 4/2002 | Antanavich et al. |
| 6,372,494 B1 | 4/2002 | Naughton et al. |
| 6,372,892 B1 | 4/2002 | Ballinger et al. |
| 6,376,742 B1 | 4/2002 | Zdrahala et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,387,693 B2 | 5/2002 | Rieser et al. |
| 6,387,964 B1 | 5/2002 | D'Agostino et al. |
| 6,392,118 B1 | 5/2002 | Hammang et al. |
| 6,394,812 B1 | 5/2002 | Sullivan et al. |
| 6,399,580 B1 | 6/2002 | Elias et al. |
| 6,410,320 B1 | 6/2002 | Humes |
| 6,414,219 B1 | 7/2002 | Denhardt et al. |

(56) References Cited

U.S. PATENT DOCUMENTS

| | | |
|---|---|---|
| 6,416,496 B1 | 7/2002 | Rogers et al. |
| 6,417,205 B1 | 7/2002 | Cooke et al. |
| 6,419,829 B2 | 7/2002 | Ho et al. |
| 6,420,138 B1 | 7/2002 | Gentz et al. |
| 6,423,681 B1 | 7/2002 | Barasch et al. |
| 6,426,332 B1 | 7/2002 | Rueger et al. |
| 6,428,802 B1 | 8/2002 | Atala |
| 6,429,012 B1 | 8/2002 | Kraus et al. |
| 6,429,013 B1 | 8/2002 | Halvorsen et al. |
| 6,432,653 B1 | 8/2002 | Okarma |
| 6,432,711 B1 | 8/2002 | Dinsmore et al. |
| 6,440,407 B1 | 8/2002 | Bauer et al. |
| 6,440,734 B1 | 8/2002 | Pykett et al. |
| 6,451,562 B1 | 9/2002 | Ruben et al. |
| 6,454,811 B1 | 9/2002 | Sherwood et al. |
| 6,455,678 B1 | 9/2002 | Yin et al. |
| 6,458,585 B1 | 10/2002 | Vachula et al. |
| 6,458,589 B1 | 10/2002 | Rambhatla et al. |
| 6,461,495 B1 | 10/2002 | Morrissey et al. |
| 6,461,853 B1 | 10/2002 | Zhu |
| 6,464,983 B1 | 10/2002 | Grotendorst |
| 6,465,205 B2 | 10/2002 | Hicks, Jr. |
| 6,465,247 B1 | 10/2002 | Weissman et al. |
| 6,465,249 B2 | 10/2002 | Reya et al. |
| 6,468,794 B1 | 10/2002 | Uchida et al. |
| 6,472,200 B1 | 10/2002 | Mitrani |
| 6,475,481 B2 | 11/2002 | Talmadge |
| 6,479,064 B1 | 11/2002 | Atala |
| 6,482,231 B1 | 11/2002 | Abatangelo et al. |
| 6,482,411 B1 | 11/2002 | Ahuja et al. |
| 6,482,645 B2 | 11/2002 | Atala |
| 6,482,926 B1 | 11/2002 | Thomas et al. |
| 6,488,925 B2 | 12/2002 | Ruben et al. |
| 6,491,918 B1 | 12/2002 | Thomas et al. |
| 6,495,129 B1 | 12/2002 | Li et al. |
| 6,495,364 B2 | 12/2002 | Hammang et al. |
| 6,497,875 B1 | 12/2002 | Sorrell et al. |
| 6,498,034 B1 | 12/2002 | Strobl |
| 6,506,574 B1 | 1/2003 | Rambhatla et al. |
| 6,511,510 B1 | 1/2003 | de Bruijn et al. |
| 6,511,767 B1 | 1/2003 | Calver et al. |
| 6,511,958 B1 | 1/2003 | Atkinson et al. |
| 6,514,514 B1 | 2/2003 | Atkinson et al. |
| 6,524,452 B1 | 2/2003 | Clark et al. |
| 6,528,052 B1 | 3/2003 | Smith et al. |
| 6,528,245 B2 | 3/2003 | Sanchez-Ramos et al. |
| 6,531,445 B1 | 3/2003 | Cohen et al. |
| 6,534,084 B1 | 3/2003 | Vyakarnam et al. |
| 6,537,807 B1 | 3/2003 | Smith et al. |
| 6,541,024 B1 | 4/2003 | Kadiyala et al. |
| 6,541,249 B2 | 4/2003 | Wager et al. |
| 6,544,506 B2 | 4/2003 | Reisner |
| 6,548,734 B1 | 4/2003 | Glimcher et al. |
| 6,555,324 B1 | 4/2003 | Olweus et al. |
| 6,555,374 B1 | 4/2003 | Gimble et al. |
| 6,559,119 B1 | 5/2003 | Burgess et al. |
| 6,562,616 B1 | 5/2003 | Toner et al. |
| 6,565,843 B1 | 5/2003 | Cohen et al. |
| 6,566,126 B2 | 5/2003 | Cadwell |
| 6,569,421 B2 | 5/2003 | Hodges |
| 6,569,427 B1 | 5/2003 | Boyse et al. |
| 6,569,428 B1 | 5/2003 | Isner et al. |
| 6,569,654 B2 | 5/2003 | Shastri et al. |
| 6,576,188 B1 | 6/2003 | Rose et al. |
| 6,576,428 B1 | 6/2003 | Assenmacher et al. |
| 6,576,464 B2 | 6/2003 | Gold et al. |
| 6,576,465 B1 | 6/2003 | Long |
| 6,582,471 B1 | 6/2003 | Bittmann et al. |
| 6,582,955 B2 | 6/2003 | Martinez et al. |
| 6,586,192 B1 | 7/2003 | Peschle et al. |
| 6,589,728 B2 | 7/2003 | Csete et al. |
| 6,589,786 B1 | 7/2003 | Mangano et al. |
| 6,596,274 B1 | 7/2003 | Abatangelo et al. |
| 6,599,300 B2 | 7/2003 | Vibe-Hansen et al. |
| 6,599,520 B2 | 7/2003 | Scarborough et al. |
| 6,610,535 B1 | 8/2003 | Lu et al. |
| 6,613,798 B1 | 9/2003 | Porter et al. |
| 6,616,912 B2 | 9/2003 | Eddleman et al. |
| 6,617,070 B1 | 9/2003 | Morrissey et al. |
| 6,617,152 B2 | 9/2003 | Bryhan et al. |
| 6,617,159 B1 | 9/2003 | Cancedda et al. |
| 6,623,749 B2 | 9/2003 | Williams et al. |
| 6,623,942 B2 | 9/2003 | Ruben et al. |
| 6,624,108 B1 | 9/2003 | Clark et al. |
| 6,626,950 B2 | 9/2003 | Brown et al. |
| 6,627,191 B1 | 9/2003 | Bartelmez et al. |
| 6,632,425 B1 | 10/2003 | Li et al. |
| 6,632,620 B1 | 10/2003 | Makarovskiy |
| 6,632,934 B1 | 10/2003 | Moreadith et al. |
| 6,638,765 B1 | 10/2003 | Rosenberg |
| 6,642,019 B1 | 11/2003 | Anderson et al. |
| 6,642,048 B2 | 11/2003 | Xu et al. |
| 6,642,049 B1 | 11/2003 | Chute et al. |
| 6,642,201 B1 | 11/2003 | Khavinson et al. |
| 6,645,489 B2 | 11/2003 | Pykett et al. |
| 6,645,727 B2 | 11/2003 | Thomas et al. |
| 6,645,763 B2 | 11/2003 | Kobayashi et al. |
| 6,649,189 B2 | 11/2003 | Talmadge et al. |
| 6,649,595 B2 | 11/2003 | Clackson et al. |
| 6,649,631 B1 | 11/2003 | Orme et al. |
| 6,653,105 B2 | 11/2003 | Triglia et al. |
| 6,653,134 B2 | 11/2003 | Prockop et al. |
| 6,660,523 B2 | 12/2003 | Blom et al. |
| 6,662,805 B2 | 12/2003 | Frondoza et al. |
| 6,667,034 B2 | 12/2003 | Palsson et al. |
| 6,667,176 B1 | 12/2003 | Funk et al. |
| 6,670,169 B1 | 12/2003 | Schob et al. |
| 6,670,175 B2 | 12/2003 | Wang et al. |
| 6,673,603 B2 | 1/2004 | Baetge et al. |
| 6,673,606 B1 | 1/2004 | Tennekoon et al. |
| 6,677,306 B1 | 1/2004 | Veis et al. |
| 6,680,166 B1 | 1/2004 | Mullon et al. |
| 6,683,192 B2 | 1/2004 | Baxter et al. |
| 6,685,936 B2 | 2/2004 | McIntosh et al. |
| 6,685,971 B2 | 2/2004 | Xu |
| 6,686,198 B1 | 2/2004 | Melton et al. |
| 6,696,575 B2 | 2/2004 | Schmidt et al. |
| 6,699,716 B2 | 3/2004 | Sullivan et al. |
| 6,703,017 B1 | 3/2004 | Peck et al. |
| 6,703,209 B1 | 3/2004 | Baetscher et al. |
| 6,706,293 B1 | 3/2004 | Quintanilla Almagro et al. |
| 6,709,864 B1 | 3/2004 | Pittenger et al. |
| 6,712,850 B2 | 3/2004 | Vyakarnam et al. |
| 6,719,969 B1 | 4/2004 | Hogaboam et al. |
| 6,719,970 B1 | 4/2004 | Costantino et al. |
| 6,720,340 B1 | 4/2004 | Cooke et al. |
| 6,730,314 B2 | 5/2004 | Jeschke et al. |
| 6,730,315 B2 | 5/2004 | Usala et al. |
| 6,730,510 B2 | 5/2004 | Roos et al. |
| 6,733,746 B2 | 5/2004 | Daley et al. |
| 6,734,000 B2 | 5/2004 | Chin et al. |
| 6,740,493 B1 | 5/2004 | Long et al. |
| 6,759,039 B2 | 7/2004 | Tsang et al. |
| 6,759,245 B1 | 7/2004 | Toner et al. |
| 6,761,883 B2 | 7/2004 | Weissman et al. |
| 6,761,887 B1 | 7/2004 | Kavalkovich et al. |
| 6,767,699 B2 | 7/2004 | Polo et al. |
| 6,767,737 B1 | 7/2004 | Wilson et al. |
| 6,767,738 B1 | 7/2004 | Gage et al. |
| 6,767,740 B2 | 7/2004 | Sramek et al. |
| 6,770,478 B2 | 8/2004 | Crowe et al. |
| 6,777,227 B2 | 8/2004 | Ricci et al. |
| 6,777,231 B1 | 8/2004 | Katz et al. |
| 6,780,612 B1 | 8/2004 | Ford et al. |
| 6,787,355 B1 | 9/2004 | Miller et al. |
| 6,790,455 B2 | 9/2004 | Chu et al. |
| 6,793,939 B2 | 9/2004 | Badylak |
| 6,797,269 B2 | 9/2004 | Mosca et al. |
| 6,797,514 B2 | 9/2004 | Berenson et al. |
| 6,800,480 B1 | 10/2004 | Bodnar et al. |
| 6,802,971 B2 | 10/2004 | Gorsuch et al. |
| 6,805,860 B1 | 10/2004 | Alt |
| 6,809,117 B2 | 10/2004 | Enikolopov et al. |
| 6,811,773 B1 | 11/2004 | Gentz et al. |

(56) References Cited

U.S. PATENT DOCUMENTS

| | | |
|---|---|---|
| 6,811,776 B2 | 11/2004 | Kale et al. |
| 6,814,961 B1 | 11/2004 | Jensen et al. |
| 6,821,513 B1 | 11/2004 | Fleming |
| 6,821,790 B2 | 11/2004 | Mahant et al. |
| 6,828,145 B2 | 12/2004 | Avital et al. |
| 6,833,269 B2 | 12/2004 | Carpenter |
| 6,835,377 B2 | 12/2004 | Goldberg et al. |
| 6,835,566 B2 | 12/2004 | Smith et al. |
| 6,838,284 B2 | 1/2005 | de Bruijn et al. |
| 6,841,150 B2 | 1/2005 | Halvorsen et al. |
| 6,841,151 B2 | 1/2005 | Stringer |
| 6,841,294 B1 | 1/2005 | Morrissey et al. |
| 6,841,355 B2 | 1/2005 | Livant |
| 6,841,386 B2 | 1/2005 | Kraus et al. |
| 6,841,542 B2 | 1/2005 | Bartelmez et al. |
| 6,844,011 B1 | 1/2005 | Faustman |
| 6,844,187 B1 | 1/2005 | Weschler et al. |
| 6,849,051 B2 | 2/2005 | Sramek et al. |
| 6,849,255 B2 | 2/2005 | Gazit et al. |
| 6,849,454 B2 | 2/2005 | Kelly et al. |
| 6,849,662 B2 | 2/2005 | Enikolopov et al. |
| 6,852,308 B2 | 2/2005 | Kohn et al. |
| 6,852,321 B2 | 2/2005 | Colucci et al. |
| 6,852,533 B1 | 2/2005 | Rafii et al. |
| 6,855,242 B1 | 2/2005 | Comninellis et al. |
| 6,855,542 B2 | 2/2005 | DiMilla et al. |
| 6,863,900 B2 | 3/2005 | Kadiyala et al. |
| 6,866,843 B2 | 3/2005 | Habener et al. |
| 6,872,389 B1 | 3/2005 | Faris |
| 6,875,430 B2 | 4/2005 | McIntosh et al. |
| 6,887,600 B2 | 5/2005 | Morrissey et al. |
| 6,887,704 B2 | 5/2005 | Peled et al. |
| 6,908,763 B1 | 6/2005 | Akashi et al. |
| 6,911,201 B1 | 6/2005 | Merchav et al. |
| 6,914,279 B2 | 7/2005 | Lu et al. |
| 6,939,955 B2 | 9/2005 | Rameshwar |
| 6,943,008 B1 | 9/2005 | Ma |
| 6,965,018 B2 | 11/2005 | Mikesell et al. |
| 6,969,308 B2 | 11/2005 | Doi et al. |
| 6,979,308 B1 | 12/2005 | McDonald et al. |
| 6,979,321 B2 | 12/2005 | Geis et al. |
| 6,988,004 B2 | 1/2006 | Kanno et al. |
| 7,008,394 B2 | 3/2006 | Geise et al. |
| 7,015,037 B1 | 3/2006 | Furcht et al. |
| 7,029,666 B2 | 4/2006 | Bruder et al. |
| 7,033,339 B1 | 4/2006 | Lynn |
| 7,033,823 B2 | 4/2006 | Chang |
| 7,041,493 B2 | 5/2006 | Rao |
| 7,045,098 B2 | 5/2006 | Stephens |
| 7,052,517 B2 | 5/2006 | Murphy et al. |
| 7,056,493 B2 | 6/2006 | Kohn et al. |
| 7,112,441 B2 | 9/2006 | Uemura et al. |
| 7,118,672 B2 | 10/2006 | Husain et al. |
| 7,122,178 B1 | 10/2006 | Simmons et al. |
| 7,160,719 B2 | 1/2007 | Nyberg |
| 7,169,295 B2 | 1/2007 | Husain et al. |
| 7,172,696 B1 | 2/2007 | Martinez et al. |
| 7,175,763 B2 | 2/2007 | Husain et al. |
| 7,192,776 B2 | 3/2007 | Stephens |
| 7,195,711 B2 | 3/2007 | Gorsuch et al. |
| 7,250,154 B2 | 7/2007 | Kohn et al. |
| 7,270,996 B2 | 9/2007 | Cannon et al. |
| 7,271,234 B2 | 9/2007 | Kohn et al. |
| 7,294,259 B2 | 11/2007 | Cote et al. |
| 7,300,571 B2 | 11/2007 | Cote et al. |
| 7,303,676 B2 | 12/2007 | Husain et al. |
| 7,303,677 B2 | 12/2007 | Cote et al. |
| 7,341,062 B2 | 3/2008 | Chachques et al. |
| 7,358,001 B2 | 4/2008 | Morrissey et al. |
| 7,361,493 B1 | 4/2008 | Hammond et al. |
| 7,368,169 B2 | 5/2008 | Kohn et al. |
| 7,378,271 B2 | 5/2008 | Bader |
| 7,399,872 B2 | 7/2008 | Webster et al. |
| 7,416,884 B2 | 8/2008 | Gemmiti et al. |
| 7,425,440 B2 | 9/2008 | Malinge et al. |
| 7,435,586 B2 | 10/2008 | Bartlett et al. |
| 7,438,902 B2 | 10/2008 | Habener et al. |
| 7,439,057 B2 | 10/2008 | Frangos et al. |
| 7,452,529 B2 | 11/2008 | Brown, Jr. et al. |
| 7,491,388 B1 | 2/2009 | McIntosh et al. |
| 7,494,811 B2 | 2/2009 | Wolfinbarger, Jr. et al. |
| 7,514,074 B2 | 4/2009 | Pittenger et al. |
| 7,514,075 B2 | 4/2009 | Hedrick et al. |
| 7,524,676 B2 | 4/2009 | Reiter et al. |
| 7,531,351 B2 | 5/2009 | Marx et al. |
| 7,534,601 B2 | 5/2009 | Wikswo et al. |
| 7,534,609 B2 | 5/2009 | Merchav et al. |
| 7,572,374 B2 | 8/2009 | Gorsuch et al. |
| 7,579,179 B2 | 8/2009 | Bryhan et al. |
| 7,585,412 B2 | 9/2009 | Gorsuch et al. |
| 7,588,938 B2 | 9/2009 | Ma |
| 7,598,075 B2 | 10/2009 | Smith et al. |
| 7,608,447 B2 | 10/2009 | Cohen et al. |
| 7,659,118 B2 | 2/2010 | Furcht et al. |
| 7,678,573 B2 | 3/2010 | Merchav et al. |
| 7,682,822 B2 | 3/2010 | Noll et al. |
| 7,682,823 B1 | 3/2010 | Runyon |
| 7,718,430 B2 | 5/2010 | Antwiler |
| 7,722,896 B2 | 5/2010 | Kohn et al. |
| D620,732 S | 8/2010 | Andrews |
| 7,838,122 B2 | 11/2010 | Kohn et al. |
| 7,838,289 B2 | 11/2010 | Furcht et al. |
| 7,892,829 B2 | 2/2011 | Pittenger et al. |
| 7,919,307 B2 | 4/2011 | Klaus et al. |
| 7,927,587 B2 | 4/2011 | Blazer et al. |
| 7,989,851 B2 | 8/2011 | Lu et al. |
| 8,008,528 B2 | 8/2011 | Kohn et al. |
| 8,034,365 B2 | 10/2011 | Baluca |
| 8,075,881 B2 | 12/2011 | Verfaillie et al. |
| 8,147,824 B2 | 4/2012 | Maziarz et al. |
| 8,147,863 B2 | 4/2012 | Kohn et al. |
| 8,158,120 B2 | 4/2012 | Pittenger et al. |
| 8,158,121 B2 | 4/2012 | Pittenger et al. |
| 8,252,280 B1 | 8/2012 | Verfaillie et al. |
| 8,252,887 B2 | 8/2012 | Bolikal et al. |
| 8,288,159 B2 | 10/2012 | Warren et al. |
| 8,288,590 B2 | 10/2012 | Kohn et al. |
| 8,298,823 B2 | 10/2012 | Warren et al. |
| 8,309,347 B2 | 11/2012 | Antwiler |
| 8,361,453 B2 | 1/2013 | Uhrich et al. |
| 8,377,683 B2 | 2/2013 | Lu et al. |
| 8,383,397 B2 | 2/2013 | Wojciechowski et al. |
| 8,383,806 B2 | 2/2013 | Rameshwar |
| 8,399,245 B2 | 3/2013 | Leuthaeuser et al. |
| 8,415,449 B2 | 4/2013 | Kohn et al. |
| 8,435,781 B2 | 5/2013 | Kodama |
| 8,461,289 B2 | 6/2013 | Kohn et al. |
| 8,476,399 B2 | 7/2013 | Bolikal et al. |
| 8,486,621 B2 | 7/2013 | Luo et al. |
| 8,486,695 B2 | 7/2013 | Danilkovitch et al. |
| 8,492,140 B2 | 7/2013 | Smith et al. |
| 8,492,150 B2 | 7/2013 | Parker et al. |
| 8,524,496 B2 | 9/2013 | Meiron et al. |
| 8,529,888 B2 | 9/2013 | Meiron et al. |
| 8,540,499 B2 | 9/2013 | Page et al. |
| 8,551,511 B2 | 10/2013 | Brandom et al. |
| 8,580,249 B2 | 11/2013 | Blazar et al. |
| 8,678,638 B2 | 3/2014 | Wong |
| 8,785,181 B2 | 7/2014 | Antwiler |
| 8,852,570 B2 | 10/2014 | Pittenger et al. |
| 8,852,571 B2 | 10/2014 | Pittenger et al. |
| 8,852,572 B2 | 10/2014 | Pittenger et al. |
| 8,852,573 B2 | 10/2014 | Pittenger et al. |
| 8,852,574 B2 | 10/2014 | Pittenger et al. |
| 8,852,575 B2 | 10/2014 | Pittenger et al. |
| 8,895,291 B2 | 11/2014 | DiLorenzo et al. |
| 9,057,045 B2 | 6/2015 | Gibbons et al. |
| 9,109,193 B2 | 8/2015 | Galliher et al. |
| 9,175,259 B2 | 11/2015 | Nankervis |
| 9,220,810 B2 | 12/2015 | Ma et al. |
| 9,441,195 B2 | 9/2016 | Wojciechowski et al. |
| 9,534,198 B2 | 1/2017 | Page et al. |
| 9,732,313 B2 | 8/2017 | Hirschel et al. |
| 10,093,956 B2 | 10/2018 | Hirschel et al. |

(56) References Cited

U.S. PATENT DOCUMENTS

| | | |
|---|---|---|
| 10,494,421 B2 | 12/2019 | Castillo |
| 10,577,575 B2 | 3/2020 | Frank |
| 2001/0017188 A1 | 8/2001 | Cooley et al. |
| 2001/0020086 A1 | 9/2001 | Hubbell et al. |
| 2001/0021516 A1 | 9/2001 | Wei et al. |
| 2001/0029046 A1 | 10/2001 | Beaulieu |
| 2001/0033834 A1 | 10/2001 | Wilkison et al. |
| 2001/0036663 A1 | 11/2001 | Kraus et al. |
| 2001/0041687 A1 | 11/2001 | Mruk |
| 2001/0044413 A1 | 11/2001 | Pierce et al. |
| 2001/0049139 A1 | 12/2001 | Lagasse et al. |
| 2002/0015724 A1 | 2/2002 | Yang et al. |
| 2002/0018804 A1 | 2/2002 | Austin et al. |
| 2002/0028510 A1 | 3/2002 | Sanberg et al. |
| 2002/0031757 A1 | 3/2002 | Ohgushi et al. |
| 2002/0037278 A1 | 3/2002 | Ueno et al. |
| 2002/0045260 A1 | 4/2002 | Hung et al. |
| 2002/0064869 A1 | 5/2002 | Ebner et al. |
| 2002/0076400 A1 | 6/2002 | Katz et al. |
| 2002/0077687 A1 | 6/2002 | Ahn |
| 2002/0082698 A1 | 6/2002 | Parenteau et al. |
| 2002/0116054 A1 | 8/2002 | Lundell et al. |
| 2002/0128581 A1 | 9/2002 | Vishnoi et al. |
| 2002/0128582 A1 | 9/2002 | Farrell et al. |
| 2002/0128583 A1 | 9/2002 | Min et al. |
| 2002/0128584 A1 | 9/2002 | Brown et al. |
| 2002/0130100 A1 | 9/2002 | Smith |
| 2002/0132343 A1 | 9/2002 | Lum |
| 2002/0139743 A1 | 10/2002 | Critz et al. |
| 2002/0142457 A1 | 10/2002 | Umezawa et al. |
| 2002/0146678 A1 | 10/2002 | Benvenisty |
| 2002/0146817 A1 | 10/2002 | Cannon et al. |
| 2002/0150989 A1 | 10/2002 | Greene et al. |
| 2002/0151056 A1 | 10/2002 | Sasai et al. |
| 2002/0159981 A1 | 10/2002 | Peled et al. |
| 2002/0160032 A1 | 10/2002 | Long et al. |
| 2002/0160510 A1 | 10/2002 | Hariri |
| 2002/0168765 A1 | 11/2002 | Prockop et al. |
| 2002/0169408 A1 | 11/2002 | Beretta et al. |
| 2002/0182241 A1 | 12/2002 | Borenstein et al. |
| 2002/0182664 A1 | 12/2002 | Dolecek et al. |
| 2002/0188962 A1 | 12/2002 | Denhardt et al. |
| 2002/0197240 A1 | 12/2002 | Chiu |
| 2003/0021850 A1 | 1/2003 | Xu |
| 2003/0022390 A1 | 1/2003 | Stephens |
| 2003/0027330 A1 | 2/2003 | Lanza et al. |
| 2003/0027331 A1 | 2/2003 | Yan et al. |
| 2003/0032143 A1 | 2/2003 | Neff et al. |
| 2003/0036168 A1 | 2/2003 | Ni et al. |
| 2003/0040113 A1 | 2/2003 | Mizuno et al. |
| 2003/0049236 A1 | 3/2003 | Kassem et al. |
| 2003/0054331 A1 | 3/2003 | Fraser et al. |
| 2003/0059851 A1 | 3/2003 | Smith |
| 2003/0059939 A1 | 3/2003 | Page et al. |
| 2003/0078345 A1 | 4/2003 | Morrisey |
| 2003/0082795 A1 | 5/2003 | Shuler et al. |
| 2003/0086915 A1 | 5/2003 | Rader et al. |
| 2003/0089471 A1 | 5/2003 | Gehr et al. |
| 2003/0092101 A1 | 5/2003 | Ni et al. |
| 2003/0101465 A1 | 5/2003 | Lawman et al. |
| 2003/0103957 A1 | 6/2003 | McKerracher |
| 2003/0104568 A1 | 6/2003 | Lee |
| 2003/0113813 A1 | 6/2003 | Heidaran et al. |
| 2003/0113910 A1 | 6/2003 | Levanduski |
| 2003/0124091 A1 | 7/2003 | Tuse et al. |
| 2003/0124721 A1 | 7/2003 | Cheatham et al. |
| 2003/0130593 A1 | 7/2003 | Gonzalez |
| 2003/0133918 A1 | 7/2003 | Sherley |
| 2003/0138950 A1 | 7/2003 | McAllister et al. |
| 2003/0143727 A1 | 7/2003 | Chang |
| 2003/0148152 A1 | 8/2003 | Morrisey |
| 2003/0149011 A1 | 8/2003 | Ackerman et al. |
| 2003/0152558 A1 | 8/2003 | Luft et al. |
| 2003/0157078 A1 | 8/2003 | Hall et al. |
| 2003/0157709 A1 | 8/2003 | DiMilla et al. |
| 2003/0161817 A1 | 8/2003 | Young et al. |
| 2003/0166272 A1 | 9/2003 | Abuljadayel |
| 2003/0170214 A1 | 9/2003 | Bader |
| 2003/0180296 A1 | 9/2003 | Salcedo et al. |
| 2003/0185817 A1 | 10/2003 | Thomas et al. |
| 2003/0202938 A1 | 10/2003 | Rameshwar |
| 2003/0203483 A1 | 10/2003 | Seshi |
| 2003/0204323 A1 | 10/2003 | Morrisey |
| 2003/0211602 A1 | 11/2003 | Atala |
| 2003/0211603 A1 | 11/2003 | Earp et al. |
| 2003/0216718 A1 | 11/2003 | Hamblin et al. |
| 2003/0219898 A1 | 11/2003 | Sugaya et al. |
| 2003/0223968 A1 | 12/2003 | Yang |
| 2003/0224420 A1 | 12/2003 | Hellerstein et al. |
| 2003/0224510 A1 | 12/2003 | Yamaguchi et al. |
| 2003/0225010 A1 | 12/2003 | Rameshwar |
| 2003/0232432 A1 | 12/2003 | Bhat |
| 2003/0232752 A1 | 12/2003 | Freeman et al. |
| 2003/0235909 A1 | 12/2003 | Hariri et al. |
| 2004/0009158 A1 | 1/2004 | Sands et al. |
| 2004/0009589 A1 | 1/2004 | Levenberg et al. |
| 2004/0010231 A1 | 1/2004 | Leonhardt et al. |
| 2004/0014209 A1 | 1/2004 | Lassar et al. |
| 2004/0018174 A1 | 1/2004 | Palasis |
| 2004/0018617 A1 | 1/2004 | Hwang |
| 2004/0023324 A1 | 2/2004 | Sakano et al. |
| 2004/0023370 A1 | 2/2004 | Yu et al. |
| 2004/0027914 A1 | 2/2004 | Vrane |
| 2004/0033214 A1 | 2/2004 | Young et al. |
| 2004/0033599 A1 | 2/2004 | Rosenberg |
| 2004/0037811 A1 | 2/2004 | Penn et al. |
| 2004/0037815 A1 | 2/2004 | Clarke et al. |
| 2004/0038316 A1 | 2/2004 | Kaiser et al. |
| 2004/0053869 A1 | 3/2004 | Andrews et al. |
| 2004/0062753 A1 | 4/2004 | Rezania et al. |
| 2004/0063205 A1 | 4/2004 | Xu |
| 2004/0067585 A1 | 4/2004 | Wang et al. |
| 2004/0071668 A1 | 4/2004 | Bays et al. |
| 2004/0072259 A1 | 4/2004 | Scadden et al. |
| 2004/0077079 A1 | 4/2004 | Storgaard et al. |
| 2004/0079248 A1 | 4/2004 | Mayer et al. |
| 2004/0087016 A1 | 5/2004 | Keating et al. |
| 2004/0091936 A1 | 5/2004 | West |
| 2004/0096476 A1 | 5/2004 | Uhrich et al. |
| 2004/0097408 A1 | 5/2004 | Leder et al. |
| 2004/0101959 A1 | 5/2004 | Marko et al. |
| 2004/0107453 A1 | 6/2004 | Furcht et al. |
| 2004/0110286 A1 | 6/2004 | Bhatia |
| 2004/0115804 A1 | 6/2004 | Fu et al. |
| 2004/0115806 A1 | 6/2004 | Fu |
| 2004/0120932 A1 | 6/2004 | Zahner |
| 2004/0121461 A1 | 6/2004 | Honmou et al. |
| 2004/0121464 A1 | 6/2004 | Rathjen et al. |
| 2004/0126405 A1 | 7/2004 | Sahatjian et al. |
| 2004/0128077 A1 | 7/2004 | Koebler et al. |
| 2004/0131601 A1 | 7/2004 | Epstein et al. |
| 2004/0132184 A1 | 7/2004 | Dennis et al. |
| 2004/0136967 A1 | 7/2004 | Weiss et al. |
| 2004/0137612 A1 | 7/2004 | Baksh |
| 2004/0137613 A1 | 7/2004 | Vacanti et al. |
| 2004/0143174 A1 | 7/2004 | Brubaker |
| 2004/0143863 A1 | 7/2004 | Li et al. |
| 2004/0151700 A1 | 8/2004 | Harlan et al. |
| 2004/0151701 A1 | 8/2004 | Kim et al. |
| 2004/0151706 A1 | 8/2004 | Shakhov et al. |
| 2004/0151729 A1 | 8/2004 | Michalopoulos et al. |
| 2004/0152190 A1 | 8/2004 | Sumita |
| 2004/0161419 A1 | 8/2004 | Strom et al. |
| 2004/0171533 A1 | 9/2004 | Zehentner et al. |
| 2004/0180347 A1 | 9/2004 | Stanton et al. |
| 2004/0191902 A1 | 9/2004 | Hambor et al. |
| 2004/0197310 A1 | 10/2004 | Sanberg et al. |
| 2004/0197375 A1 | 10/2004 | Rezania et al. |
| 2004/0208786 A1 | 10/2004 | Kevy et al. |
| 2004/0214275 A1 | 10/2004 | Soejima et al. |
| 2004/0219134 A1 | 11/2004 | Naughton et al. |
| 2004/0219136 A1 | 11/2004 | Hariri |
| 2004/0219563 A1 | 11/2004 | West et al. |
| 2004/0224403 A1 | 11/2004 | Bhatia |

(56) References Cited

U.S. PATENT DOCUMENTS

| | | |
|---|---|---|
| 2004/0229351 A1 | 11/2004 | Rodriguez et al. |
| 2004/0234972 A1 | 11/2004 | Owens et al. |
| 2004/0235158 A1 | 11/2004 | Bartlett et al. |
| 2004/0235160 A1 | 11/2004 | Nishikawa et al. |
| 2004/0235166 A1 | 11/2004 | Prockop et al. |
| 2004/0242469 A1 | 12/2004 | Lee et al. |
| 2004/0258669 A1 | 12/2004 | Dzau et al. |
| 2004/0259242 A1 | 12/2004 | Malinge et al. |
| 2004/0259254 A1 | 12/2004 | Honmou et al. |
| 2004/0260058 A1 | 12/2004 | Scheek et al. |
| 2004/0260318 A1 | 12/2004 | Hunter et al. |
| 2004/0265996 A1 | 12/2004 | Schwarz et al. |
| 2005/0002914 A1 | 1/2005 | Rosen et al. |
| 2005/0003460 A1 | 1/2005 | Nilsson et al. |
| 2005/0003527 A1 | 1/2005 | Lang et al. |
| 2005/0003534 A1 | 1/2005 | Huberman et al. |
| 2005/0008624 A1 | 1/2005 | Peled et al. |
| 2005/0008626 A1 | 1/2005 | Fraser et al. |
| 2005/0009178 A1 | 1/2005 | Yost et al. |
| 2005/0009179 A1 | 1/2005 | Gemmiti et al. |
| 2005/0009181 A1 | 1/2005 | Black et al. |
| 2005/0013804 A1 | 1/2005 | Kato et al. |
| 2005/0014252 A1 | 1/2005 | Chu et al. |
| 2005/0014253 A1 | 1/2005 | Ehmann et al. |
| 2005/0014254 A1 | 1/2005 | Kruse |
| 2005/0014255 A1 | 1/2005 | Tang et al. |
| 2005/0019801 A1 | 1/2005 | Rubin et al. |
| 2005/0019908 A1 | 1/2005 | Hariri |
| 2005/0019910 A1 | 1/2005 | Takagi et al. |
| 2005/0019911 A1 | 1/2005 | Gronthos et al. |
| 2005/0026836 A1 | 2/2005 | Dack et al. |
| 2005/0031587 A1 | 2/2005 | Tsutsui et al. |
| 2005/0031595 A1 | 2/2005 | Peled et al. |
| 2005/0031598 A1 | 2/2005 | Levenberg et al. |
| 2005/0032122 A1 | 2/2005 | Hwang et al. |
| 2005/0032207 A1 | 2/2005 | Wobus et al. |
| 2005/0032209 A1 | 2/2005 | Messina et al. |
| 2005/0032218 A1 | 2/2005 | Gerlach |
| 2005/0036980 A1 | 2/2005 | Chaney et al. |
| 2005/0037488 A1 | 2/2005 | Mitalipova et al. |
| 2005/0037490 A1 | 2/2005 | Rosenberg et al. |
| 2005/0037492 A1 | 2/2005 | Xu et al. |
| 2005/0037493 A1 | 2/2005 | Mandalam et al. |
| 2005/0037949 A1 | 2/2005 | O'Brien et al. |
| 2005/0106119 A1 | 5/2005 | Brandom et al. |
| 2005/0106127 A1 | 5/2005 | Kraus et al. |
| 2005/0112447 A1 | 5/2005 | Fletcher et al. |
| 2005/0112762 A1 | 5/2005 | Hart et al. |
| 2005/0118712 A1 | 6/2005 | Tsai et al. |
| 2005/0130297 A1 | 6/2005 | Sarem et al. |
| 2005/0136093 A1 | 6/2005 | Denk |
| 2005/0137517 A1 | 6/2005 | Blickhan et al. |
| 2005/0142162 A1 | 6/2005 | Hunter et al. |
| 2005/0149157 A1 | 7/2005 | Hunter et al. |
| 2005/0152946 A1 | 7/2005 | Hunter et al. |
| 2005/0158289 A1 | 7/2005 | Simmons et al. |
| 2005/0172340 A1 | 8/2005 | Logvinov et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0180957 A1 | 8/2005 | Scharp et al. |
| 2005/0181502 A1 | 8/2005 | Furcht et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0186671 A1 | 8/2005 | Cannon et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2005/0244963 A1 | 11/2005 | Teplyashin |
| 2005/0249731 A1 | 11/2005 | Aslan et al. |
| 2005/0255118 A1 | 11/2005 | Wehner |
| 2005/0261674 A1 | 11/2005 | Nobis et al. |
| 2005/0277577 A1 | 12/2005 | Hunter et al. |
| 2005/0281790 A1 | 12/2005 | Simmons et al. |
| 2005/0282733 A1 | 12/2005 | Prins et al. |
| 2005/0283844 A1 | 12/2005 | Furcht et al. |
| 2006/0002900 A1 | 1/2006 | Binder et al. |
| 2006/0008452 A1 | 1/2006 | Simmons et al. |
| 2006/0019388 A1 | 1/2006 | Hutmacher et al. |
| 2006/0019389 A1 | 1/2006 | Yayon et al. |
| 2006/0054941 A1 | 3/2006 | Lu et al. |
| 2006/0083720 A1 | 4/2006 | Fraser et al. |
| 2006/0099198 A1 | 5/2006 | Thomson et al. |
| 2006/0166364 A1 | 7/2006 | Senesac |
| 2006/0172008 A1 | 8/2006 | Yayon et al. |
| 2006/0193840 A1 | 8/2006 | Gronthos et al. |
| 2006/0228798 A1 | 10/2006 | Verfaillie et al. |
| 2006/0233834 A1 | 10/2006 | Guehenneux et al. |
| 2006/0239909 A1 | 10/2006 | Anderson et al. |
| 2006/0258586 A1 | 11/2006 | Sheppard et al. |
| 2006/0258933 A1 | 11/2006 | Ellis et al. |
| 2006/0259998 A1 | 11/2006 | Brumbley et al. |
| 2006/0280748 A1 | 12/2006 | Buckheit |
| 2006/0286077 A1 | 12/2006 | Gronthos et al. |
| 2007/0005148 A1 | 1/2007 | Barofsky et al. |
| 2007/0011752 A1 | 1/2007 | Paleyanda |
| 2007/0042462 A1 | 2/2007 | Hildinger |
| 2007/0065938 A1 | 3/2007 | Gronthos et al. |
| 2007/0105222 A1 | 5/2007 | Wolfinbarger et al. |
| 2007/0116612 A1 | 5/2007 | Williamson |
| 2007/0117180 A1 | 5/2007 | Morikawa et al. |
| 2007/0122904 A1 | 5/2007 | Nordon |
| 2007/0123996 A1 | 5/2007 | Sugaya et al. |
| 2007/0160583 A1 | 7/2007 | Lange et al. |
| 2007/0166834 A1 | 7/2007 | Williamson et al. |
| 2007/0178071 A1 | 8/2007 | Westenfelder |
| 2007/0196421 A1 | 8/2007 | Hunter et al. |
| 2007/0197957 A1 | 8/2007 | Hunter et al. |
| 2007/0198063 A1 | 8/2007 | Hunter et al. |
| 2007/0202485 A1 | 8/2007 | Nees et al. |
| 2007/0203330 A1 | 8/2007 | Kretschmar et al. |
| 2007/0208134 A1 | 9/2007 | Hunter et al. |
| 2007/0231305 A1 | 10/2007 | Noll et al. |
| 2007/0238169 A1 | 10/2007 | Abilez et al. |
| 2007/0258943 A1 | 11/2007 | Penn et al. |
| 2007/0274970 A1 | 11/2007 | Gordon et al. |
| 2007/0275457 A1 | 11/2007 | Granchelli et al. |
| 2007/0295651 A1 | 12/2007 | Martinez et al. |
| 2007/0298015 A1 | 12/2007 | Beer et al. |
| 2007/0298497 A1 | 12/2007 | Antwiler |
| 2008/0003663 A1 | 1/2008 | Bryhan et al. |
| 2008/0009458 A1 | 1/2008 | Dornan et al. |
| 2008/0032398 A1 | 2/2008 | Cannon et al. |
| 2008/0050770 A1 | 2/2008 | Zhang et al. |
| 2008/0063600 A1 | 3/2008 | Aguzzi et al. |
| 2008/0064649 A1 | 3/2008 | Rameshwar |
| 2008/0069807 A1 | 3/2008 | Jy et al. |
| 2008/0095676 A1 | 4/2008 | Andretta |
| 2008/0095690 A1 | 4/2008 | Liu |
| 2008/0103412 A1 | 5/2008 | Chin |
| 2008/0110827 A1 | 5/2008 | Cote et al. |
| 2008/0113426 A1 | 5/2008 | Smith et al. |
| 2008/0113440 A1 | 5/2008 | Gurney et al. |
| 2008/0153077 A1 | 6/2008 | Henry |
| 2008/0160597 A1 | 7/2008 | van der Heiden et al. |
| 2008/0166808 A1 | 7/2008 | Nyberg |
| 2008/0181879 A1 | 7/2008 | Catelas et al. |
| 2008/0190857 A1 | 8/2008 | Beretta et al. |
| 2008/0194017 A1 | 8/2008 | Esser et al. |
| 2008/0206831 A1 | 8/2008 | Coffey et al. |
| 2008/0220522 A1 | 9/2008 | Antwiler |
| 2008/0220523 A1 | 9/2008 | Antwiler |
| 2008/0220524 A1 | 9/2008 | Noll et al. |
| 2008/0220526 A1 | 9/2008 | Ellison et al. |
| 2008/0221443 A1 | 9/2008 | Ritchie et al. |
| 2008/0227189 A1 | 9/2008 | Bader |
| 2008/0227190 A1 | 9/2008 | Antwiler |
| 2008/0248572 A1 | 10/2008 | Antwiler |
| 2008/0254533 A1 | 10/2008 | Antwiler |
| 2008/0268165 A1 | 10/2008 | Fekety et al. |
| 2008/0306095 A1 | 12/2008 | Crawford |
| 2009/0004738 A1 | 1/2009 | Merchav et al. |

(56) References Cited

U.S. PATENT DOCUMENTS

| | | |
|---|---|---|
| 2009/0011399 A1 | 1/2009 | Fischer |
| 2009/0047289 A1 | 2/2009 | Denhardt et al. |
| 2009/0074728 A1 | 3/2009 | Gronthos et al. |
| 2009/0075881 A1 | 3/2009 | Catelas et al. |
| 2009/0076481 A1 | 3/2009 | Stegmann et al. |
| 2009/0081770 A1 | 3/2009 | Srienc et al. |
| 2009/0081797 A1 | 3/2009 | Fadeev et al. |
| 2009/0092608 A1 | 4/2009 | Ni et al. |
| 2009/0098103 A1 | 4/2009 | Madison et al. |
| 2009/0098645 A1 | 4/2009 | Fang et al. |
| 2009/0100944 A1 | 4/2009 | Newby |
| 2009/0104163 A1 | 4/2009 | Deans et al. |
| 2009/0104692 A1 | 4/2009 | Bartfeld et al. |
| 2009/0104699 A1 | 4/2009 | Newby et al. |
| 2009/0118161 A1 | 5/2009 | Cruz |
| 2009/0181087 A1 | 7/2009 | Kraus et al. |
| 2009/0183581 A1 | 7/2009 | Wilkinson et al. |
| 2009/0191627 A1 | 7/2009 | Fadeev et al. |
| 2009/0191632 A1 | 7/2009 | Fadeev et al. |
| 2009/0191634 A1 | 7/2009 | Martin et al. |
| 2009/0203065 A1 | 8/2009 | Gehman et al. |
| 2009/0203129 A1 | 8/2009 | Furcht et al. |
| 2009/0203130 A1 | 8/2009 | Furcht et al. |
| 2009/0214382 A1 | 8/2009 | Burgess et al. |
| 2009/0214481 A1 | 8/2009 | Muhs et al. |
| 2009/0214652 A1 | 8/2009 | Hunter et al. |
| 2009/0215022 A1 | 8/2009 | Page et al. |
| 2009/0227024 A1 | 9/2009 | Baker et al. |
| 2009/0227027 A1 | 9/2009 | Baker et al. |
| 2009/0233334 A1 | 9/2009 | Hildinger et al. |
| 2009/0233353 A1 | 9/2009 | Furcht et al. |
| 2009/0233354 A1 | 9/2009 | Furcht et al. |
| 2009/0258379 A1 | 10/2009 | Klein et al. |
| 2009/0269841 A1 | 10/2009 | Wojciechowski et al. |
| 2009/0270725 A1 | 10/2009 | Leimbach et al. |
| 2009/0280153 A1 | 11/2009 | Hunter et al. |
| 2009/0280565 A1 | 11/2009 | Jolicoeur et al. |
| 2009/0291890 A1 | 11/2009 | Madison et al. |
| 2010/0009409 A1 | 1/2010 | Hubbell et al. |
| 2010/0021954 A1 | 1/2010 | Deshayes et al. |
| 2010/0021990 A1 | 1/2010 | Edwards et al. |
| 2010/0028311 A1 | 2/2010 | Motlagh et al. |
| 2010/0042260 A1 | 2/2010 | Antwiler |
| 2010/0075410 A1 | 3/2010 | Desai et al. |
| 2010/0086481 A1 | 4/2010 | Baird et al. |
| 2010/0092536 A1 | 4/2010 | Hunter et al. |
| 2010/0093607 A1 | 4/2010 | Dickneite |
| 2010/0105138 A1 | 4/2010 | Dodd et al. |
| 2010/0111910 A1 | 5/2010 | Rakoczy |
| 2010/0129376 A1 | 5/2010 | Denhardt et al. |
| 2010/0129912 A1 | 5/2010 | Su et al. |
| 2010/0136091 A1 | 6/2010 | Moghe et al. |
| 2010/0144037 A1 | 6/2010 | Antwiler |
| 2010/0144634 A1 | 6/2010 | Zheng et al. |
| 2010/0183561 A1 | 7/2010 | Sakthivel et al. |
| 2010/0183585 A1 | 7/2010 | Van Zant et al. |
| 2010/0203020 A1 | 8/2010 | Ghosh |
| 2010/0230203 A1 | 9/2010 | Karayianni |
| 2010/0248366 A1 | 9/2010 | Fadeev et al. |
| 2010/0278933 A1 | 11/2010 | Sayeski et al. |
| 2010/0285453 A1 | 11/2010 | Goodrich |
| 2010/0285590 A1 | 11/2010 | Verfaillie et al. |
| 2010/0291180 A1 | 11/2010 | Uhrich |
| 2010/0291181 A1 | 11/2010 | Uhrich et al. |
| 2010/0297234 A1 | 11/2010 | Sugino et al. |
| 2010/0304427 A1 | 12/2010 | Faris et al. |
| 2010/0304482 A1 | 12/2010 | Deshayes et al. |
| 2010/0310524 A1 | 12/2010 | Bechor et al. |
| 2010/0316446 A1 | 12/2010 | Runyon |
| 2011/0085746 A1 | 4/2011 | Wong et al. |
| 2011/0111498 A1 | 5/2011 | Oh et al. |
| 2011/0129447 A1 | 6/2011 | Meretzki et al. |
| 2011/0129486 A1 | 6/2011 | Meiron |
| 2011/0143433 A1 | 6/2011 | Oh et al. |
| 2011/0159584 A1 | 6/2011 | Gibbons et al. |
| 2011/0171182 A1 | 7/2011 | Abelman |
| 2011/0171659 A1 | 7/2011 | Furcht et al. |
| 2011/0177595 A1 | 7/2011 | Furcht et al. |
| 2011/0212493 A1 | 9/2011 | Hirschel et al. |
| 2011/0256108 A1 | 10/2011 | Meiron et al. |
| 2011/0256160 A1 | 10/2011 | Meiron et al. |
| 2011/0293583 A1 | 12/2011 | Aberman |
| 2012/0028352 A1 | 2/2012 | Oh et al. |
| 2012/0051976 A1 | 3/2012 | Lu et al. |
| 2012/0058554 A1 | 3/2012 | Deshayes et al. |
| 2012/0064047 A1 | 3/2012 | Verfaillie et al. |
| 2012/0064583 A1 | 3/2012 | Edwards et al. |
| 2012/0086657 A1 | 4/2012 | Stanton, IV et al. |
| 2012/0118919 A1 | 5/2012 | Cianciolo |
| 2012/0122220 A1 | 5/2012 | Merchav et al. |
| 2012/0135043 A1 | 5/2012 | Maziarz et al. |
| 2012/0145580 A1 | 6/2012 | Paruit et al. |
| 2012/0156779 A1 | 6/2012 | Anneren et al. |
| 2012/0178885 A1 | 7/2012 | Kohn et al. |
| 2012/0189713 A1 | 7/2012 | Kohn et al. |
| 2012/0208039 A1 | 8/2012 | Barbaroux et al. |
| 2012/0219531 A1 | 8/2012 | Oh et al. |
| 2012/0219737 A1 | 8/2012 | Sugino et al. |
| 2012/0226013 A1 | 9/2012 | Kohn et al. |
| 2012/0231519 A1 | 9/2012 | Bushman et al. |
| 2012/0237557 A1 | 9/2012 | Lewitus et al. |
| 2012/0295352 A1 | 11/2012 | Antwiler |
| 2012/0308531 A1 | 12/2012 | Pinxteren et al. |
| 2012/0315696 A1 | 12/2012 | Luitjens et al. |
| 2013/0004465 A1 | 1/2013 | Aberman |
| 2013/0039892 A1 | 2/2013 | Aberman |
| 2013/0058907 A1 | 3/2013 | Wojciechowski et al. |
| 2013/0059383 A1 | 3/2013 | Dijkhuizen Borgart et al. |
| 2013/0101561 A1 | 4/2013 | Sabaawy |
| 2013/0143313 A1 | 6/2013 | Niazi |
| 2013/0157353 A1 | 6/2013 | Dijkhuizen Borgart et al. |
| 2013/0259843 A1 | 10/2013 | Duda et al. |
| 2013/0319575 A1 | 12/2013 | Mendyk |
| 2013/0323213 A1 | 12/2013 | Meiron et al. |
| 2013/0337558 A1 | 12/2013 | Meiron et al. |
| 2014/0004553 A1 | 1/2014 | Parker et al. |
| 2014/0017209 A1 | 1/2014 | Aberman et al. |
| 2014/0030805 A1 | 1/2014 | Kasuto et al. |
| 2014/0051162 A1 | 2/2014 | Nankervis |
| 2014/0051167 A1 | 2/2014 | Nankervis et al. |
| 2014/0112893 A1 | 4/2014 | Tom et al. |
| 2014/0186937 A1 | 7/2014 | Smith et al. |
| 2014/0193895 A1 | 7/2014 | Smith et al. |
| 2014/0193911 A1 | 7/2014 | Newby et al. |
| 2014/0242039 A1 | 8/2014 | Meiron et al. |
| 2014/0248244 A1 | 9/2014 | Danilkovitch et al. |
| 2014/0315300 A1 | 10/2014 | Oh et al. |
| 2014/0342448 A1 | 11/2014 | Nagels |
| 2015/0004693 A1 | 1/2015 | Danilkovitch et al. |
| 2015/0104431 A1 | 4/2015 | Pittenger et al. |
| 2015/0111252 A1 | 4/2015 | Hirschel et al. |
| 2015/0125138 A1 | 5/2015 | Karnieli et al. |
| 2015/0140653 A1* | 5/2015 | Jones .................. C12M 27/10 435/325 |
| 2015/0175950 A1 | 6/2015 | Hirschel et al. |
| 2015/0225685 A1 | 8/2015 | Hirschel et al. |
| 2015/0247122 A1 | 9/2015 | Tom et al. |
| 2015/0259749 A1 | 9/2015 | Santos et al. |
| 2015/0275170 A1 | 10/2015 | Nankervis |
| 2016/0090569 A1 | 3/2016 | Vang |
| 2016/0326494 A1* | 11/2016 | Cunha .................. C12N 5/0676 |
| 2016/0362650 A1 | 12/2016 | Wojciechowski et al. |
| 2016/0362652 A1 | 12/2016 | Page et al. |
| 2017/0349869 A1 | 12/2017 | Frank et al. |
| 2017/0349872 A1 | 12/2017 | Frank |
| 2017/0349873 A1 | 12/2017 | Frank et al. |
| 2018/0010082 A1 | 1/2018 | Jaques et al. |
| 2018/0030398 A1 | 2/2018 | Castillo |

(56) References Cited

U.S. PATENT DOCUMENTS

| | | |
|---|---|---|
| 2018/0155668 A1 | 6/2018 | Hirschel et al. |
| 2019/0194628 A1 | 6/2019 | Rao et al. |

FOREIGN PATENT DOCUMENTS

| | | | |
|---|---|---|---|
| DE | 10244859 A1 | 4/2004 | |
| DE | 10327988 A1 | 7/2004 | |
| DE | 102012200939 A1 | 7/2013 | |
| EP | 0220650 A2 | 5/1987 | |
| EP | 750938 A1 | 1/1997 | |
| EP | 906415 A1 | 4/1999 | |
| EP | 959980 A1 | 12/1999 | |
| EP | 1007631 A1 | 6/2000 | |
| EP | 1028737 A1 | 8/2000 | |
| EP | 1028991 A1 | 8/2000 | |
| EP | 1066052 A2 | 1/2001 | |
| EP | 1066060 A2 | 1/2001 | |
| EP | 1084230 A2 | 3/2001 | |
| EP | 1147176 A1 | 10/2001 | |
| EP | 1220611 A1 | 7/2002 | |
| EP | 1223956 A1 | 7/2002 | |
| EP | 1325953 A1 | 7/2003 | |
| EP | 1437404 A1 | 7/2004 | |
| EP | 1437406 A2 | 7/2004 | |
| EP | 1447443 A1 | 8/2004 | |
| EP | 1452594 A1 | 9/2004 | |
| EP | 1062321 B1 | 12/2004 | |
| EP | 1484080 A1 | 12/2004 | |
| EP | 1498478 A1 | 1/2005 | |
| EP | 1538196 A1 | 6/2005 | |
| EP | 1036057 B1 | 10/2005 | |
| EP | 1605044 A2 | 12/2005 | |
| EP | 1756262 A1 | 2/2007 | |
| EP | 1771737 A1 | 4/2007 | |
| EP | 1882030 A1 | 1/2008 | |
| EP | 1908490 A1 | 4/2008 | |
| EP | 1971679 A2 | 9/2008 | |
| EP | 1991668 A2 | 11/2008 | |
| EP | 2200622 A1 | 6/2010 | |
| EP | 2208782 A2 | 7/2010 | |
| EP | 2264145 A1 | 12/2010 | |
| EP | 2027247 B1 | 1/2011 | |
| EP | 2303293 A1 | 4/2011 | |
| EP | 2311938 A1 | 4/2011 | |
| EP | 2331957 A1 | 6/2011 | |
| EP | 2334310 A2 | 6/2011 | |
| EP | 2334783 A2 | 6/2011 | |
| EP | 2361968 A1 | 8/2011 | |
| EP | 2366775 A1 | 9/2011 | |
| EP | 2465922 A2 | 6/2012 | |
| EP | 2548951 A1 | 1/2013 | |
| EP | 2561066 A1 | 2/2013 | |
| EP | 2575831 A1 | 4/2013 | |
| EP | 2591789 A2 | 5/2013 | |
| EP | 2624845 A2 | 8/2013 | |
| EP | 2626417 A1 | 8/2013 | |
| EP | 2641606 A1 | 9/2013 | |
| EP | 2689008 A1 | 1/2014 | |
| EP | 2694639 A1 | 2/2014 | |
| EP | 2697362 A2 | 2/2014 | |
| EP | 2739720 A1 | 6/2014 | |
| EP | 2807246 A1 | 12/2014 | |
| GB | 1414671 A | 11/1975 | |
| GB | 2297980 A | 8/1996 | |
| GB | 2360789 A | 10/2001 | |
| HU | 3285 U | 5/2007 | |
| JP | H02245177 A | 9/1990 | |
| JP | 2003/052360 A | 2/2003 | |
| JP | 2003510068 A | 3/2003 | |
| JP | 2005278564 A | 10/2005 | |
| JP | 2006223273 A | 8/2006 | |
| JP | 2007000038 A | 1/2007 | |
| JP | 5548207 B2 | 7/2014 | |
| MY | 115206 A | 4/2003 | |
| WO | 86/02379 A1 | 4/1986 | |
| WO | 88/01643 A1 | 3/1988 | |
| WO | 90/02171 A1 | 3/1990 | |
| WO | WO-9013306 A2 | 11/1990 | |
| WO | WO-9105238 A1 | 4/1991 | |
| WO | 91/07485 A1 | 5/1991 | |
| WO | WO-9106641 A1 | 5/1991 | |
| WO | WO-9109194 A1 | 6/1991 | |
| WO | 92/10564 A1 | 6/1992 | |
| WO | WO-94/25571 A1 | 11/1994 | |
| WO | 95/04813 A1 | 2/1995 | |
| WO | 95/21911 A1 | 8/1995 | |
| WO | WO-96/29395 A1 | 9/1996 | |
| WO | WO-96/39035 A1 | 12/1996 | |
| WO | WO-97/05826 A1 | 2/1997 | |
| WO | 97/16527 A1 | 5/1997 | |
| WO | WO-97/29792 A1 | 8/1997 | |
| WO | WO-97/39104 A1 | 10/1997 | |
| WO | WO-1997-040137 A1 | 10/1997 | |
| WO | WO-98/31403 A1 | 7/1998 | |
| WO | 98/53046 A1 | 11/1998 | |
| WO | WO-98/51317 A1 | 11/1998 | |
| WO | WO-98/51785 A1 | 11/1998 | |
| WO | WO-99/05180 A1 | 2/1999 | |
| WO | WO-99/24391 A1 | 5/1999 | |
| WO | WO-99/24490 A1 | 5/1999 | |
| WO | WO-99/27167 A1 | 6/1999 | |
| WO | WO-99/49015 A2 | 9/1999 | |
| WO | WO-00/06704 A2 | 2/2000 | |
| WO | WO-0009018 A1 | 2/2000 | |
| WO | WO-00/16420 A1 | 3/2000 | |
| WO | WO-00/17326 A1 | 3/2000 | |
| WO | WO-00/29002 A2 | 5/2000 | |
| WO | WO-0032225 A1 | 6/2000 | |
| WO | WO-00/44058 A2 | 7/2000 | |
| WO | WO-0054651 A2 | 9/2000 | |
| WO | WO-0056405 A2 | 9/2000 | |
| WO | WO-00/59933 A2 | 10/2000 | |
| WO | WO-00/69449 A2 | 11/2000 | |
| WO | 00/75275 A2 | 12/2000 | |
| WO | WO-00/75196 A1 | 12/2000 | |
| WO | WO-00/77236 A2 | 12/2000 | |
| WO | WO-2001/000783 A2 | 1/2001 | |
| WO | WO-2001/011011 A2 | 2/2001 | |
| WO | WO-2001/018174 A2 | 3/2001 | |
| WO | WO-2001/021766 A2 | 3/2001 | |
| WO | 01/23520 A1 | 4/2001 | |
| WO | WO-2001/025402 A1 | 4/2001 | |
| WO | WO-2001/029189 A2 | 4/2001 | |
| WO | WO-0122810 A2 | 4/2001 | |
| WO | WO-2001/034167 A1 | 5/2001 | |
| WO | WO-2001/049851 A1 | 7/2001 | |
| WO | WO-2001/054706 A2 | 8/2001 | |
| WO | WO-2001-094541 A2 | 12/2001 | |
| WO | 02/28996 A1 | 4/2002 | |
| WO | WO-2002/042422 A2 | 5/2002 | |
| WO | WO-2002/057430 A2 | 7/2002 | |
| WO | WO-2002/092794 A2 | 11/2002 | |
| WO | WO-2002/101385 A1 | 12/2002 | |
| WO | WO-2003/010303 A1 | 2/2003 | |
| WO | WO-2003/014313 A2 | 2/2003 | |
| WO | WO-2003/016916 A1 | 2/2003 | |
| WO | WO-2003/023018 A2 | 3/2003 | |
| WO | WO-2003/023019 A1 | 3/2003 | |
| WO | WO-2003/025167 A2 | 3/2003 | |
| WO | WO-2003/029402 A2 | 4/2003 | |
| WO | WO-2003/040336 A2 | 5/2003 | |
| WO | WO-2003/042405 A2 | 5/2003 | |
| WO | WO-2003/046161 A2 | 6/2003 | |
| WO | WO-2003/055989 A2 | 7/2003 | |
| WO | WO-2003/061685 A1 | 7/2003 | |
| WO | WO-2003/061686 A1 | 7/2003 | |
| WO | WO-2003/068961 A2 | 8/2003 | |
| WO | WO-2003/072064 A2 | 9/2003 | |
| WO | WO-2003/078609 A1 | 9/2003 | |
| WO | WO-2003/078967 A2 | 9/2003 | |
| WO | WO-2003/080816 A2 | 10/2003 | |
| WO | WO-2003/082145 A2 | 10/2003 | |
| WO | WO-2003/085099 A2 | 10/2003 | |
| WO | WO-2003/089631 A1 | 10/2003 | |

(56) References Cited

FOREIGN PATENT DOCUMENTS

| | | |
|---|---|---|
| WO | WO-2003/091398 A2 | 11/2003 |
| WO | WO-2003/095631 A1 | 11/2003 |
| WO | 03/105663 A2 | 12/2003 |
| WO | WO-2004/001697 A1 | 12/2003 |
| WO | WO-2004/012226 A2 | 2/2004 |
| WO | WO-2004/016779 A1 | 2/2004 |
| WO | 2004024303 A2 | 3/2004 |
| WO | WO-2004/018526 A1 | 3/2004 |
| WO | WO-2004/018655 A2 | 3/2004 |
| WO | WO-2004/026115 A2 | 4/2004 |
| WO | WO-2004/029231 A1 | 4/2004 |
| WO | WO-2004/042023 A2 | 5/2004 |
| WO | WO-2004/042033 A2 | 5/2004 |
| WO | WO-2004/042040 A1 | 5/2004 |
| WO | WO-2004/044127 A2 | 5/2004 |
| WO | WO-2004/044158 A2 | 5/2004 |
| WO | WO-2004/046304 A1 | 6/2004 |
| WO | WO-2004/050826 A2 | 6/2004 |
| WO | WO-2004/053096 A2 | 6/2004 |
| WO | WO-2004/055155 A2 | 7/2004 |
| WO | WO-2004/056186 A1 | 7/2004 |
| WO | WO-2004/065616 A2 | 8/2004 |
| WO | WO-2004/069172 A2 | 8/2004 |
| WO | WO-2004/070013 A2 | 8/2004 |
| WO | WO-2004/072264 A2 | 8/2004 |
| WO | WO-2004/073633 A2 | 9/2004 |
| WO | WO-2004/074464 A1 | 9/2004 |
| WO | WO-2004/076642 A2 | 9/2004 |
| WO | WO-2004/076653 A1 | 9/2004 |
| WO | 2004/090112 A2 | 10/2004 |
| WO | WO-2004/087870 A2 | 10/2004 |
| WO | WO-2004/094588 A2 | 11/2004 |
| WO | WO-2004/096975 A2 | 11/2004 |
| WO | WO-2004/104166 A2 | 12/2004 |
| WO | WO-2004/106499 A1 | 12/2004 |
| WO | WO-2004/113513 A2 | 12/2004 |
| WO | WO-2005/001033 A2 | 1/2005 |
| WO | WO-2005/001081 A1 | 1/2005 |
| WO | WO-2005/003320 A2 | 1/2005 |
| WO | WO-2005/007799 A2 | 1/2005 |
| WO | WO-2005/010172 A2 | 2/2005 |
| WO | WO-2005/011524 A1 | 2/2005 |
| WO | WO-2005/012480 A2 | 2/2005 |
| WO | WO-2005/012510 A1 | 2/2005 |
| WO | WO-2005/012512 A1 | 2/2005 |
| WO | WO-05014775 A2 | 2/2005 |
| WO | WO-2005/028433 A2 | 3/2005 |
| WO | WO-05044972 A2 | 5/2005 |
| WO | WO-2005/056747 A2 | 6/2005 |
| WO | WO-05051316 A2 | 6/2005 |
| WO | WO-2005/063303 A1 | 7/2005 |
| WO | WO-2005/075636 A1 | 8/2005 |
| WO | 2005087915 A2 | 9/2005 |
| WO | WO-2005/107760 A1 | 11/2005 |
| WO | WO-2006/009291 A1 | 1/2006 |
| WO | WO-2006/032075 A1 | 3/2006 |
| WO | WO-2006/032092 A1 | 3/2006 |
| WO | WO-2006/108229 A1 | 10/2006 |
| WO | WO-2006/113881 A2 | 10/2006 |
| WO | WO-2006/121445 A2 | 11/2006 |
| WO | WO-06124021 A1 | 11/2006 |
| WO | WO-06129312 A2 | 12/2006 |
| WO | WO-2007/115367 A1 | 10/2007 |
| WO | WO-2007/115368 A1 | 10/2007 |
| WO | 2007/136821 A1 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A2 | 12/2007 |
| WO | WO-2008/006168 A1 | 1/2008 |
| WO | WO-2008/011664 A1 | 1/2008 |
| WO | WO-2008/017128 A1 | 2/2008 |
| WO | WO-2008/028241 A1 | 3/2008 |
| WO | WO-08040812 A1 | 4/2008 |
| WO | 2008/109674 A2 | 9/2008 |
| WO | WO-2008/116261 A1 | 10/2008 |
| WO | WO-2008/149129 A1 | 12/2008 |
| WO | 2009/034186 A2 | 3/2009 |
| WO | WO-2009/026635 A1 | 3/2009 |
| WO | WO-09058146 A1 | 5/2009 |
| WO | WO-09080054 A1 | 7/2009 |
| WO | WO-09081408 A2 | 7/2009 |
| WO | WO-2009/140452 A2 | 11/2009 |
| WO | WO-09132457 A1 | 11/2009 |
| WO | WO-2009/144720 A1 | 12/2009 |
| WO | WO-10005527 A1 | 1/2010 |
| WO | WO-2010/019886 A1 | 2/2010 |
| WO | WO-10014253 A2 | 2/2010 |
| WO | WO-10019997 A1 | 2/2010 |
| WO | WO-2010/026573 A1 | 3/2010 |
| WO | WO-2010/026574 A2 | 3/2010 |
| WO | WO-2010/026575 A2 | 3/2010 |
| WO | WO-2010/036760 A1 | 4/2010 |
| WO | WO-2010/059487 A1 | 5/2010 |
| WO | WO-10061377 A2 | 6/2010 |
| WO | WO-10068710 A2 | 6/2010 |
| WO | WO-10071826 A2 | 6/2010 |
| WO | WO-10083385 A2 | 7/2010 |
| WO | WO-10111255 A1 | 9/2010 |
| WO | WO-10119036 A1 | 10/2010 |
| WO | WO-10123594 A2 | 10/2010 |
| WO | WO-2011/025445 A1 | 3/2011 |
| WO | WO-2011/132087 A1 | 10/2011 |
| WO | WO-2011/147967 A1 | 12/2011 |
| WO | WO-2012/072924 A1 | 6/2012 |
| WO | WO-2012/127320 A1 | 9/2012 |
| WO | WO-2012/138968 A1 | 10/2012 |
| WO | WO-2012/140519 A2 | 10/2012 |
| WO | 2012/171026 A2 | 12/2012 |
| WO | 2012/171030 A2 | 12/2012 |
| WO | WO-2013/110651 A1 | 8/2013 |
| WO | WO-2014/037862 A1 | 3/2014 |
| WO | WO-2014/037863 A1 | 3/2014 |
| WO | WO-2014/068508 A2 | 5/2014 |
| WO | WO-2014/128306 A1 | 8/2014 |
| WO | WO-2014/128634 A1 | 8/2014 |
| WO | WO-2014/131846 A1 | 9/2014 |
| WO | WO-2014/141111 A1 | 9/2014 |
| WO | WO-2015/004609 A2 | 1/2015 |
| WO | 2015/073913 A1 | 5/2015 |
| WO | WO-2015/118148 A1 | 8/2015 |
| WO | WO-2015/118149 A1 | 8/2015 |
| WO | WO-2015/131143 A1 | 9/2015 |
| WO | WO-2017/072201 A2 | 5/2017 |

OTHER PUBLICATIONS

Chang, Ho Nam, "Membrane Bioreactors: Engineering Aspects", Biotech. Adv., 1987, pp. 129-145, vol. 5.
Edgington, Stephen M., "New Horizons for Stem-Cell Bioreactors", Biotechnology, Oct. 1992, pp. 1099-1106, vol. 10.
Gastens et al., "Good Manufacturing Practice-Compliant Expansion of Marrow-Derived Stem and Progenitor Cells for Cell Therapy", Cell Transplantation, 2007, pp. 685-696, vol. 16.
Gramer et al., "Screening Tool for Hollow-Fiber Bioreactor Process Development", Biotechnol. Prog., 1998, pp. 203-209, vol. 14.
Hirschel et al., "An Automated Hollow Fiber System for the Large Scale Manufacture of Mammalian Cell Secreted Product", Large Scale Cell Culture Technology, ed. Bjorn K. Lydersen, 1987, pp. 113-144, Hanser Publishers.
Infanger et al., "Simulated weightlessness changes the cytoskeleton and extracellular matrix proteins in papillary thyroid carcinoma cells", Cell and Tissue Research, 2006, 324(2): 267-277.
Jones et al., "Genetic stability of bone marrow-derived human mesenchymal stromal cells in the Quantum System", Cytotherapy, 2013; 15: 1323-1339.
Liu et al., "Ex vivo Expansion of Hematopoietic Stem Cells Derived from Umbilical Cord Blood in Rotating Wall Vessel", Journal of Biotechnology, 2006, 124:592-601.
Nankervis et al., "Shear Stress Conditions in the Quantum Cell Expansion System", Poster Session—TERMIS AM Annual Conference 2013, Nov. 12, 2013.

(56) References Cited

OTHER PUBLICATIONS

Nguyen et al., "Quantum® Cell Expansion System: Automated Expansion of Human Mesenchymal Stem Cells from Precultured Cells Using the Quantum Cell Expansion System", Terumo BCT, Inc., 2012.
Nielsen, Lars Keld, "Bioreactors for Hematopoietic Cell Culture", Annu. Rev. Biomed. Eng., 1999, vol. 1, pp. 129-152.
Pörtner et al., "An Overview on Bioreactor Design, Prototyping and Process Control for Reproducible Three-Dimensional Tissue Culture", Drug Testing in Vitro: Breakthroughs and Trends in Cell Culture Technology, ed. Uwe Marx and Volker Sandig, 2007, Wiley-VCH, pp. 53-78.
Zhao et al., "Perfusion Bioreactor System for Human Mesenchymal Stem Cell Tissue Engineering: Dynamic Cell Seeding and Construct Development", Biotechnology and Bioengineering, Aug. 20, 2005, vol. 91, No. 4, pp. 482-493.
Biovest International, "AutovaxIDTM: advanced hollow fibre bioreactors with automated lactate control yield higher density monoclonal antibody production", VWRbioMarke, No. 21, Sep. 2008, pp. 10-11.
Clausen et al., "Lactate as an Indicator of Terminating Time in Insect Cell Culture Baculovirus Expression Vector Systems", Biotechnology Techniques, vol. 10, No. 10, Oct. 1996, pp. 721-726.
Gerlach, J.C. et al., "Comparison of hollow fibre membranes for hepatocyte immobilization in bioreactors," The International Journal of Artificial Organs, 1996, vol. 19 No. 10, pp. 610-616.
Gloeckner et al., "New Miniaturized Hollow-Fiber Bioreacter for in Vivo Like Cell Culture, Cell Expansion, and Production of Cell-Derived Products", Biotechnol. Prog., Aug. 21, 2001, vol. 17, No. 5, pp. 828-831.
Grayson et al., "Effects of Hypoxia on Human Mesenchymal Stem Cell Expansion and Plasticity in 3D Constructs", J. Cellular Physiology, 2006, 207:331-339.
Lloyd, J.R. et al., "Hollow-Fibre bioreactors compared to batch and chemostat culture for the production of a recombinant toxoid by a marine Vibrio," Appl. Microbiol Biotechnol, Aug. 1997, vol. 48, pp. 155-161.
Neumann, Detlef et al., "Bioreaktorsteurung mit grafischer Bedienoberflache," ATP Automatisierungstechnische Praxis, Mar. 1995, pp. 16-23, vol. 37, No. 3, Munchen, DE. (English language translation provided).
Notice of Allowance and Fee(s) Due, U.S. Appl. No. 15/616,635, dated Feb. 5, 2020.
Notice of Allowance and Fee(s) Due, U.S. Appl. No. 15/616,635, dated Apr. 22, 2020.
Notice of Allowance and Fee(s) Due, U.S. Appl. No. 15/616,745, dated Nov. 14, 2019.
Notice of Allowance and Fee(s) Due, U.S. Appl. No. 15/616,876, dated Jan. 2, 2020.
Office Action, U.S. Appl. No. 15/616,635, dated Jun. 24, 2019.
Office Action, U.S. Appl. No. 15/616,745, dated Jun. 10, 2019.
Office Action, U.S. Appl. No. 15/616,876, dated Apr. 18, 2019.
Ozturk et al., "Real-Time Monitoring and Control of Glucose and Lactate Concentrations in a Mammalian Cell Perfusion Reactor", Biotechnology and Bioengineering, vol. 53, No. 4, Feb. 20, 1997, pp. 372-378.
Sauer, I. et al., "Extracorporeal liver support based on primary human liver cells and albumin dialysis—treatment of patient with primary graft non function," Journal of Hepatology, Oct. 2003, vol. 39 No. 4, pp. 649-653.
Wang et al., "Influence of Oxygen on the Proliferation and Metabolism of Adipose Derived Adult Stem Cells", J. Cellular Physiology, 2005, 204:184-161.
Zhao et al., "Effects of Oxygen Transport on 3-D human Mesenchymal Stem Cell Metabolic Activity in Perfusion and Static Cultures: Experiments and Mathematical Model", Biotechnol. Prog, 2005, 27, 1269-1280.
Abumiya, et al at National Cardiovascular Center Research Institute in Japan, suggest that subjecting human umbilical vein endothelial cells (HUVECs) to laminar shear stress for a period of 8 hours increased the relative expression of VEGFR-2 mRNA (Ateriosclerosis, Thrombosis, and Vascular Biology, 2002).
Afzali B, Edozie FC, Fazekasova H, Scotta C, Mitchell PJ, Canavan JB, Kordasti SY, Chana PS, Ellis R, Lord GM, John S, Hilton R, Lechler RI, Lombardi G. Comparison of regulatory T cells in hemodialysis patients and healthy controls: implications for cell therapy in transplantation. Clin J Am Soc Nephrol. 2013;8(8):1396-405.
Akram, Khondoker M., et al. "Mesenchymal stem cells promote alveolar epithelial cell wound repair in vitro through distinct migratory and paracrine mechanisms." Respiratory research 14.1 (2013): 1-16.
Alberts B, Johnson A, Lewis J, et al. Molecular Biology of the Cell. 4th edition. New York: Garland Science; 2002. Fibroblasts and Their Transformations: The Connective-Tissue Cell Family. Available from: https://www.ncbi.nlm.nih.gov/books/NBK26889.
Alenazi, Noof A., et al. "Modified polyether-sulfone membrane: A mini review." Designed monomers and polymers 20.1 (2017): 532-546.
Almeida L, Lochner M, Berod L, Sparwasser T. Metabolic pathways in T cell activation and lineage differentiation. Semin Immunol. 2016;28(5):514-524.
Amy Putnam, Todd M. Brusko, Michael R. Lee, Weihong Liu, Gregory L. Szot, Taumoha Ghosh, Mark A. Atkinson, and Jeffrey A. Bluestone. Expansion of human regulatory T-Cells from patients with Type 1 Diabetes. Diabetes, 58: 652-662, 2009.
Anamelechi, Charles C., et al. "Streptavidin binding and endothelial cell adhesion to biotinylated fibronectin." *Langmuir* 23.25 (2007): 12583-12588.
Anurathapan et al., "Engineered T cells for cancer treatment," Cytotherapy, vol. 16, pp. 713-733, 2014.
Aronowski J, Samways E, Strong R, Rhoades HM, Grotta JC. An alternative method for the quantitation of neuronal damage after experimental middle cerebral artery occlusion in rats: Analysis of behavioral deficit. Journal of cerebral blood flow and metabolism : official journal of the International Society of Cerebral Blood Flow and Metabolism. 1996;16:705-713.
Arrigoni, Chiara, et al. "Rotating versus perfusion bioreactor for the culture of engineered vascular constructs based on hyaluronic acid." Biotechnology and bioengineering 100.5 (2008): 988-997.
Azar, Toni, Jody Sharp, and David Lawson. "Heart rates of male and female Sprague-Dawley and spontaneously hypertensive rats housed singly or in groups." Journal of the American Association for Laboratory Animal Science 50.2 (2011): 175-184.
Baecher-Allan, Clare, et al. "CD4+ CD25high regulatory cells in human peripheral blood." The Journal of Immunology 167.3 (2001): 1245-1253.
Bai, Tao, et al. "Expansion of primitive human hematopoietic stem cells by culture in a zwitterionic hydrogel." *Nature medicine* 25.10 (2019): 1566-1575.
Bai/Delaney (Nohla Therapeutics) showed that expanding Cord Blood-derived CD34+CD38-CD45RA-HSPCs in a biodegradable zwitterionic hydrogel with a rNotch ligand cocktail for 24 days mitigated HSPC differentiation and promoted self-renewal of lymphoid and myeloid cell phenotypes in an NSG mouse model (Nature Medicine, 2019).
Ballas CB, Zielske SP, Gerson SL (2002) Adult bone marrow stem cells for cell and gene therapies: implications for greater use. J Cell Biochem Suppl 38: 20-28.
Ballke C, Gran E, Baekkevold ES, Jahnsen FL. Characterization of Regulatory T-Cell Markers in CD4+ T Cells of the Upper Airway Mucosa. PLoS One. 2016;11(2):e0148826.
Baraniak PR, McDevitt TC (2010) Stem cell paracrine actions and tissue regeneration. Regen Med 5(1): 121-143.
Barckhausen C, Rice B, Baila S, et al. (2016) GMP-Compliant Expansion of Clinical-Grade Human Mesenchymal Stromal/Stem Cells Using a Closed Hollow Fiber Bioreactor. Methods Mol Biol 1416: 389-412.
Barker et al. "CD34+ Cell Content of 126 341 Cord Blood Units in the US Inventory: Implications for Transplantation and Banking," blood Advances, vol. 3, No. 8, pp. 1267-1271, Apr. 23, 2019.

(56) References Cited

OTHER PUBLICATIONS

Barker, Juliet N., et al. "CD34+ cell content of 126 341 cord blood units in the US inventory: implications for transplantation and banking." *Blood advances* 3.8 (2019): 1267-1271.
Bazarian JJ, Cernak I, Noble-Haeusslein L, Potolicchio S, Temkin N. Long-term neurologic outcomes after traumatic brain injury. The Journal of head trauma rehabilitation. 2009;24:439-451.
Bending D, Pesenacker AM, Ursu S, Wu Q, Lom H, Thirugnanabalan B, Wedderburn LR. Hypomethylation at the regulatory T cell-specific demethylated region in CD25hi T cells is decoupled from FOXP3 expression at the inflamed site in childhood arthritis. J Immunol. 2014;193(6):2699-708.
Berendse M, Grounds MD, Lloyd CM (2003) Myoblast structure affects subsequent skeletal myotube morphology and sarcomere assembly. Exp Cell Res 291(2): 435-450.
Bernard, A., Payton, Mark 1995. "Fermentation and Growth of *Escherichia coli* for Optimal Protein Production".
Berney SM, Schaan T, Wolf RE, van der Heyde H, Atkinson TP. CD2 (OKT11) augments CD3-mediated intracellular signaling events in human T lymphocytes. J Investig Med. 2000;48(2):102-9.
Bioheart Clinical Trial Clinica 1302 Apr. 18, 2008.
Biomolecular and Cellular Interactions with the Hollow Fiber Membrane Currently Used in the Quantum® Cell Expansion System. 12th NJ Symposium on Biomaterials Science, Oct. 6-7, 2014, New Brunswick, NJ.
Blache C, Chauvin JM, Marie-Cardine A, Contentin N, Pommier P, Dedreux I, Francois S, Jacquot S, Bastit D, Boyer O. Reduced frequency of regulatory T cells in peripheral blood stem cell compared to bone marrow transplantations. Biol Blood Marrow Transplant. 2010;16(3):430-4.
Bluestone et al. Type 1 diabetes immunotherapy using polyclonal regulatory T cells. Science Translational Medicine 7(315):1-34, 2015.
Bluestone JA, Tang Q. Treg cells—the next frontier of cell therapy. Science. 2018;362(6411):154-155.
Bluestone, Jeffrey A., et al. "Type 1 diabetes immunotherapy using polyclonal regulatory T cells." *Science translational medicine* 7.315 (2015): 315ra189-315ra189.
Blum S, Moore AN, Adams F, Dash PK. A mitogen-activated protein kinase cascade in the ca1/ca2 subfield of the dorsal hippocampus is essential for long-term spatial memory. The Journal of neuroscience : the official journal of the Society for Neuroscience. 1999; 19:3535-3544.
Boitano, Anthony E., et al. "Aryl hydrocarbon receptor antagonists promote the expansion of human hematopoietic stem cells." Science 329.5997 (2010): 1345-1348.
Bojun Li et al. Heparin-induced conformation changes of fibronectin within the extracellular matrix promote hMSC osteogenic differentiation. Biomaterials Science 3: 73-84, 2015.
Boquest AC, Shahdadfar A, Brinchmann JE, Collas P. Isolation of Stromal Stem Cells from Human Adipose Tissue. Methods Mol Biol. 2006;325:35-46. doi: 10.1385/1-59745-005-7:35. PMID: 16761717.
Borden, M. and Longo, M., "Dissolution Behavior of Lipid Monolayer-Coated, Air-Filled Microbubbles: Effect of Lipid Hydrophobic Chain Length," Langmuir, vol. 18, pp. 9225-9233, 2002.
Bourke, Sharon L., and Joachim Kohn. "Polymers derived from the amino acid L-tyrosine: polycarbonates, polyarylates and copolymers with poly (ethylene glycol)." Advanced drug delivery reviews 55.4 (2003): 447-466.
Brand, K. and Hermfisse, U., "Aerobic Glycolysis by Proliferating Cells: a Protective Strategy against Reactive Oxygen Species," The FASEB Journal, vol. 11, pp. 388-395, Apr. 1997.
Brentjens et al., "CD19-Targeted T Cells Rapidly Induce Molecular Remission in Adults with Chemotherapy-Refractory Acute Lympohblastic Leukemia," Science Translational Medicine, vol. 5, Issue 177, pp. 1-9, Mar. 20, 2013.
Brentjens et al., "Safety and Persistance of Adoptively Transferred Autologous CD19-Target T Cells in Patients with Relapsed or Chemotherapy Refractory B-Cell Leukemias," Blood, vol. 118, No. 18, pp. 4817-4828, Nov. 3, 2011.
Brunstein C, Miller J, Cao Q, Mckenna D, Hippen K, Curtsinger J, DeFor T, Levine B, June C, Rubinstein P, McGlave P, Blazar B, Wagner J. Infusion of ex vivo expanded T regulatory cells in adults transplanted with umbilical cord blood: safety profile and detection kinetics. Blood 2011; 117(3):1061-1070.
C. H. Weaver, et al. An Analysis of Engraftment Kinetics as a function of the CD34 Content of the Peripheral Blood Progenitor Cell Collections in 692 Patients After the Administration of Myeloablative Chemotherapy. Blood 86(10): 3691-3969, 1995.
Cano, Àngels, Cristina Minguillón, and Cristina Palet. "Immobilization of endo-1, 4-β-xylanase on polysulfone acrylate membranes: Synthesis and characterization." Journal of membrane science 280. 1-2 (2006): 383-388.
Carswell, K. and Papoutsakis, E. "Culture of Human T Cells in Stirred Bioreactors for Cellular Immunotherapy Applications: Shear, Proliferation, and the IL-2 Receptor," Biotechnology and Bioengineering, vol. 68, No. 3, pp. 329-338, May 5, 2000.
Celeste Nelson et al., Emergent patterns of growth controlled by multicellular form and mechanics, (in Christopher Chen's Lab demonstrated, in separate experiments, that curved surfaces with a radius of curvature (200 ?m) that is greater than the cell diameter and surfaces that have undulating special patterning (depressions) increase the patterned growth of ECs [PNAS 102(33): 11594-11599, 2005].
Chapman NM, Chi H. mTOR signaling, Tregs and immune modulation. Immunotherapy. 2014;6(12):1295-311.
Chaudhry A, Samstein RM, Treuting P, Liang Y, Pils MC, Heinrich JM, Jack RS, Wunderlich FT, Bruning JC, Muller W, Rudensky AY. Interleukin-10 signaling in regulatory T cells is required for suppression of Th17 cell-mediated inflammation. Immunity. 2011;34(4):566-78.
Chen, C. and Broden, M., "The Role of Poly(theylene glycol) Brush Architecture in Complement Activation on Targeted Microbubble Surfaces," Biomaterials, vol. 32, No. 27, pp. 6579-6587, Jun. 17, 2011.
Choi W, Kwon SJ, Jin HJ, et al. (2017) Optimization of culture conditions for rapid clinical-scale expansion of human umbilical cord blood-derived mesenchymal stem cells. Clin Transl Med 6(1): 38.
Chullikana A, Majumdar AS, Gottipamula S, et al. (2015) Randomized, double-blind, phase I/II study of intravenous allogeneic mesenchymal stromal cells in acute myocardial infarction. Cytotherapy 17(3): 250-261.
Claudio G. Brunstein, Jeffrey S. Miller, Qing Cao, Daivd H. McKenna, Keli L. Hippen, Julie Curtsinger, Todd Defor, Bruce L. Levine, Carl H. June, Pablo Rubinstein, Philip B. McGlave, Bruce R. Blazar, and John E. Wagner. Infusion of ex vivo expanded T regulatory cells in adults transplanted with umbilical cord blood: safety profile and detection kinetics. Blood, 117(3): 1061-1070, 2010.
Coeshott C, Vang B, Jones M, Nankervis B. Large-scale expansion and characterization of CD3(+) T-cells in the Quantum((R)) Cell Expansion System. J Transl Med. 2019;17(1):258.
Coombes JL, Robinson NJ, Maloy KJ, Uhlig HH, Powrie F. Regulatory T cells and intestinal homeostasis. Immunol Rev. 2005;204:184-94.
Coquillard C. mTOR Signaling in Regulatory T cell Differentiation and Expansion. SOJ Immunology. 2015;3(1):1-10.
Creed JA, DiLeonardi AM, Fox DP, Tessler AR, Raghupathi R. Concussive brain trauma in the mouse results in acute cognitive deficits and sustained impairment of axonal function. Journal of neurotrauma. 2011;28:547-563.
Cuchiara, Maude L., et al. "Covalent immobilization of stem cell factor and stromal derived factor 1α for in vitro culture of hematopoietic progenitor cells." Acta biomaterialia 9.12 (2013): 9258-9269.
Da Silva, Ricardo MP, Joao F. Mano, and Rui L. Reis. "Smart thermoresponsive coatings and surfaces for tissue engineering: switching cell-material boundaries." Trends in Biotechnology 25.12 (2007): 577-583.

(56) References Cited

OTHER PUBLICATIONS

Dash PK, Hochner B, Kandel ER. Injection of the camp-responsive element into the nucleus of aplysia sensory neurons blocks long-term facilitation. Nature. 1990;345:718-721.

Dash PK, Johnson D, Clark J, Orsi SA, Zhang M, Zhao J, Grill RJ, Moore AN, Pati S. Involvement of the glycogen synthase kinase-3 signaling pathway in tbi pathology and neurocognitive outcome. PloS one. 2011;6:e24648.

Dash PK, Mach SA, Blum S, Moore AN. Intrahippocampal wortmannin infusion enhances long-term spatial and contextual memories. Learn Mem. 2002;9:167-177.

Dash PK, Orsi SA, Zhang M, Grill RJ, Pati S, Zhao J, Moore AN. Valproate administered after traumatic brain injury provides neuroprotection and improves cognitive function in rats. PloS one. 2010;5:e11383.

Dash PK, Zhao J, Orsi SA, Zhang M, Moore AN. Sulforaphane improves cognitive function administered following traumatic brain injury. Neuroscience letters. 2009;460:103-107.

Davila et al., "Efficacy and Toxicity Management of 19-28z CAR T Cell Therapy in B cell Acute Lymphoblastic Leukemia," Science Translational Medicine, vol. 6, No. 224, pp. 1-10, Feb. 19, 2014.

Dejana E, Orsenigo F, Lampugnani MG. The role of adherens junctions and ve-cadherin in the control of vascular permeability. Journal of cell science. 2008;121:2115-2122.

Dejana E, Spagnuolo R, Bazzoni G. Interendothelial junctions and their role in the control of angiogenesis, vascular permeability and leukocyte transmigration. Thrombosis and haemostasis. 2001;86:308-315.

Dejana E, Tournier-Lasserve E, Weinstein BM. The control of vascular integrity by endothelial cell junctions: Molecular basis and pathological implications. Developmental cell. 2009;16:209-221.

Del Pino A, Ligero G, Lopez MB, et al. (2015) Morphology, cell viability, karyotype, expression of surface markers and plasticity of three primary cell line cultures before and after the cryostorage in LN2 and GN2. Cryobiology 70(1): 1-8.

Delaney, Colleen, et al. "Notch-mediated expansion of human cord blood progenitor cells capable of rapid myeloid reconstitution." Nature medicine 16.2 (2010): 232-236.

Ding, Zhongli, Guohua Chen, and Allan S. Hoffman. "Synthesis and purification of thermally sensitive oligomer? enzyme conjugates of poly (N-isopropylacrylamide)? trypsin." Bioconjugate chemistry 7.1 (1996): 121-125.

Dixon CE, Clifton GL, Lighthall JW, Yaghmai AA, Hayes Rl. A controlled cortical impact model of traumatic brain injury in the rat. Journal of neuroscience methods. 1991;39:253-262.

Dominici M, Le Blanc K, Mueller I, et al. (2006) Minimal criteria for defining multipotent mesenchymal stromal cells. The International Society for Cellular Therapy position statement. Cytotherapy 8(4): 315-317.

Durrani S, Konoplyannikov M, Ashraf M, Haider KH (2010) Skeletal myoblasts for cardiac repair. Regen Med 5(6): 919-932.

Esensten JH, Muller YD, Bluestone JA, Tang Q. Regulatory T-cell therapy for autoimmune and autoinflammatory diseases: The next frontier. J Allergy Clin Immunol. 2018;142(6):1710-1718.

Fakin R, Hamacher J, Gugger M, Gazdhar A, Moser H, Schmid RA. Prolonged amelioration of acute lung allograft rejection by sequential overexpression of human interleukin-10 and hepatocyte growth factor in rats. Exp Lung Res. 2011;37(9):555-62.

Fedorov et al., "PD-1- and CTLA-4-Based Inhibitory Chimeric Antigen Receptors (iCARs) Divert Off-Target Immunotherapy Responses," Science Translational Medicine, vol. 5, No. 215, pp. 1-12, Dec. 11, 2013.

Ferreira LMR, Muller YD, Bluestone JA, Tang Q. Next-generation regulatory T cell therapy. Nat Rev Drug Discov. 2019;18(10):749-769.

Fischbach, Michael A., Jeffrey A. Bluestone, and Wendell A. Lim. "Cell-based therapeutics: the next pillar of medicine." Science translational medicine 5.179 (2013): 179ps7-179ps7.

Fisk, Nicholas M., et al. "Can routine commercial cord blood banking be scientifically and ethically justified?." PLoS medicine 2.2 (2005): e44.

Forbes Jun. 23, 2014 article "Will this man cure cancer?"

Fowler DH. Rapamycin-resistant effector T-cell therapy. Immunol Rev. 2014;257(1):210-25.

Fraser H, Safinia N, Grageda N, Thirkell S, Lowe K, Fry LJ, Scotta C, Hope A, Fisher C, Hilton R, Game D, Harden P, Bushell A, Wood K, Lechler RI, Lombardi G. A Rapamycin-Based GMP-Compatible Process for the Isolation and Expansion of Regulatory T Cells for Clinical Trials. Mol Ther Methods Clin Dev. 2018;8:198-209.

Frauwirth KA, Riley JL, Harris MH, Parry RV, Rathmell JC, Plas DR, Elstrom RL, June CH, Thompson CB. The CD28 signaling pathway regulates glucose metabolism. Immunity. 2002;16(6):769-77.

Fuchs A, Gliwinski M, Grageda N, Spiering R, Abbas AK, Appel S, Bacchetta R, Battaglia M, Berglund D, Blazar B, Bluestone JA, Bornhauser M, Ten Brinke A, Brusko TM, Cools N, Cuturi MC, Geissler E, Giannoukakis N, Golab K, Hafler DA, van Ham SM, Hester J et al. Minimum Information about T Regulatory Cells: A Step toward Reproducibility and Standardization. Front Immunol. 2017;8:1844.

G0211: Study for Gamma Irradiation of Bioreactor Membranes, undated, author unknown, 3 pages.

Galgani M, De Rosa V, La Cava A, Matarese G. Role of Metabolism in the Immunobiology of Regulatory T Cells. J Immunol. 2016;197(7):2567-75.

Garlie, Nina K., et al. "T cells coactivated with immobilized anti-CD3 and anti-CD28 as potential immunotherapy for cancer." Journal of immunotherapy (Hagerstown, Md.: 1997) 22.4 (1999): 336-345.

Gedaly R, De Stefano F, Turcios L, Hill M, Hidalgo G, Mitov MI, Alstott MC, Butterfield DA, Mitchell HC, Hart J, Al-Attar A, Jennings CD, Marti F. mTOR Inhibitor Everolimus in Regulatory T Cell Expansion for Clinical Application in Transplantation. Transplantation. 2019;103(4):705-715.

Gimble, Jeffrey M., Adam J. Katz, and Bruce A. Bunnell. "Adipose-derived stem cells for regenerative medicine." Circulation research 100.9 (2007): 1249-1260.

Gingras AC, Raught B, Sonenberg N. Regulation of translation initiation by FRAP/mTOR. Genes Dev. 2001;15(7):807-26.

Godin, Michel, et al. "Measuring the mass, density, and size of particles and cells using a suspended microchannel resonator." Applied physics letters 91.12 (2007): 123121.

Goh, Celeste, Sowmya Narayanan, and Young S. Hahn. "Myeloid-derived suppressor cells: the dark knight or the joker in viral infections?." *Immunological reviews* 255.1 (2013): 210-221.

Golab K, Leveson-Gower D, Wang XJ, Grzanka J, Marek-Trzonkowska N, Krzystyniak A, Millis JM, Trzonkowski P, Witkowski P. Challenges in cryopreservation of regulatory T cells (Tregs) for clinical therapeutic applications. Int Immunopharmacol. 2013;16(3):371-5.

Goldring CE, Duffy PA, Benvenisty N, Andrews PW, Ben-David U, Eakins R, French N, Hanley NA, Kelly L, Kitteringham NR, Kurth J, Ladenheim D, Laverty H, McBlane J, Narayanan G, Patel S, Reinhardt J, Rossi A, Sharpe M, Park BK. Assessing the safety of stem cell therapeutics. Cell stem cell. 2011;8:618-628.

Griesche, Nadine, et al. "A simple modification of the separation method reduces heterogeneity of adipose-derived stem cells." cells tissues organs 192.2 (2010): 106-115.

Gutcher I, Donkor MK, Ma Q, Rudensky AY, Flavell RA, Li MO. Autocrine transforming growth factor-beta1 promotes in vivo Th17 cell differentiation. Immunity. 2011;34(3):396-408.

Haack-Sorensen M, Follin B, Juhl M, et al. (2016) Culture expansion of adipose derived stromal cells. A closed automated Quantum Cell Expansion System compared with manual flask-based culture. J Transl Med 14(1): 319.

Hall ED, Sullivan PG, Gibson TR, Pavel KM, Thompson BM, Scheff SW. Spatial and temporal characteristics of neurodegeneration after controlled cortical impact in mice: More than a focal brain injury. Journal of neurotrauma. 2005;22:252-265.

Hami et al., "GMP Production and Testing of Xcellerated T Cells for the Treatment of Patients with CLL," Cytotherapy, pp. 554-562, 2004.

(56) References Cited

OTHER PUBLICATIONS

Hamm RJ, Dixon CE, Gbadebo DM, Singha AK, Jenkins LW, Lyeth BG, Hayes RL. Cognitive deficits following traumatic brain injury produced by controlled cortical impact. Journal of neurotrauma. 1992;9:11-20.

Hanley PJ, Mei Z, Durett AG, et al. (2014) Efficient manufacturing of therapeutic mesenchymal stromal cells with the use of the Quantum Cell Expansion System. Cytotherapy 16(8): 1048-1058.

Harimoto, Masami, et al. "Novel approach for achieving double-layered cell sheets co-culture: overlaying endothelial cell sheets onto monolayer hepatocytes utilizing temperature-responsive culture dishes." Journal of Biomedical Materials Research: An Official Journal of The Society for Biomaterials, The Japanese Society for Biomaterials, and The Australian Society for Biomaterials and the Korean Society for Biomaterials 62.3 (2002): 464-470.

He N, Fan W, Henriquez B, Yu RT, Atkins AR, Liddle C, Zheng Y, Downes M, Evans RM. Metabolic control of regulatory T cell (Treg) survival and function by Lkb1. Proc Natl Acad Sci U S A. 2017;114(47):12542-12547.

He X, Landman S, Bauland SC, van den Dolder J, Koenen HJ, Joosten I. A TNFR2-Agonist Facilitates High Purity Expansion of Human Low Purity Treg Cells. PLoS One. 2016;11(5):e0156311.

Heskins, Michael, and James E. Guillet. "Solution properties of poly (N-isopropylacrylamide)." Journal of Macromolecular Science—Chemistry 2.8 (1968): 1441-1455.

Hill JA, Feuerer M, Tash K, Haxhinasto S, Perez J, Melamed R, Mathis D, Benoist C. Foxp3 transcription-factor-dependent and -independent regulation of the regulatory T cell transcriptional signature. Immunity. 2007;27(5):786-800.

Högstedt, Benkt, Anita Karlsson, and Anders Holmén. "Frequency and size distribution of micronuclei in lymphocytes stimulated with phytohemagglutinin and pokeweed mitogen in workers exposed to piperazine." Hereditas 109.(1988): 139-142.

Hollyman et al., "Manufacturing Validation of Biologicall Functional T Cells Targeted to CD19 Antigen for Autologous Adoptive Cell Therapy," J Immunother, vol. 32, No. 2, pp. 169-180, Feb.-Mar. 2009.

Horwitz, Mitchell E., et al. "Phase I/II study of stem-cell transplantation using a single cord blood unit expanded ex vivo with nicotinamide." *Journal of Clinical Oncology* 37.5 (2019): 367-373. http://www.ucdenver.edu/academics/colleges/medicalschool/centers/cancercenter/Research/sharedresources/AnimalImaging/smallanimalimaging/Pages/MRI.aspx.

ISCT Webinar "Volume Reduction technology for Large Scale Harvest or Post-thaw Manipulation of Cellular Therapeutics".

Itkin, Tomer, and Tsvee Lapidot. "SDF-1 keeps HSC quiescent at home." Blood, The Journal of the American Society of Hematology 117.2 (2011): 373-374.

Iwashima, Shigejiro, et al. "Novel culture system of mesenchymal stromal cells from human subcutaneous adipose tissue." Stem cells and development 18.4 (2009): 533-544.

Jang, Eugene, et al. "Syndecan-4 proteoliposomes enhance fibroblast growth factor-2 (FGF-2)-induced proliferation, migration, and neovascularization of ischemic muscle." Proceedings of the National Academy of Sciences 109.5 (2012): 1679-1684.

Jarocha D, Stangel-Wojcikiewicz K, Basta A, Majka M (2014) Efficient myoblast expansion for regenerative medicine use. Int J Mol Med 34(1): 83-91.

Jin, H., and J. Bae. "Neuropeptide Y regulates the hematopoietic stem cell microenvironment and prevents nerve injury in the bone marrow." *22nd Annual ISCT Meeting* (2016): S29.

Jo CH, Lee YG, Shin WH, et al. (2014) Intra-articular injection of mesenchymal stem cells for the treatment of osteoarthritis of the knee: a proof-of-concept clinical trial. Stem Cells 32(5): 1254-1266.

Johansson, Ulrika, et al. "Pancreatic islet survival and engraftment is promoted by culture on functionalized spider silk matrices." PloS one 10.6 (2015): e0130169.

John Carvell, et al. Monitoring Live Biomass in Disposable Bioreactors, BioProcess International 14(3)s, Mar. 2016.

John Nicolette, et al (Abbott Laboratories). In Vitro Micronucleus Screening of Pharmaceutical Candidates by Flow Cyto9metry in Chinese Hamster V79 Cells, Environmental and Molecular Mutagenesis 00:000-000, 2010.

John P. Carvell and Jason E. Dowd. On-line measurements and control of viable cell density in cell culture manufacturing processes using radio frequency impedance. Cytotechnology 50: 35-48, 2006.

Johnson, Patrick A., et al. "Interplay of anionic charge, poly (ethylene glycol), and iodinated tyrosine incorporation within tyrosine? derived polycarbonates: Effects on vascular smooth muscle cell adhesion, proliferation, and motility." Journal of Biomedical Materials Research Part A: An Official Journal of The Society for Biomaterials, The Japanese Society for Biomaterials, and The Australian Society for Biomaterials and the Korean Society for Biomaterials 93.2 (2010): 505-514.

Johnston LC, Su X, Maguire-Zeiss K, Horovitz K, Ankoudinova I, Guschin D, Hadaczek P, Federoff HJ, Bankiewicz K, Forsayeth J. Human interleukin-10 gene transfer is protective in a rat model of Parkinson's disease. Mol Ther. 2008;16(8):1392-9.

Jones2016ISCT 2016 Poster 69.

Joy, Abraham, et al. "Control of surface chemistry, substrate stiffness, and cell function in a novel terpolymer methacrylate library." Langmuir 27.5 (2011): 1891-1899.

Kalamasz et al., "Optimization of Human T-Cell Expansion Ex Vivo Using Magnetic Beads Conjugated with Anti-CD3 and Anti-CD28 Antibodies," J Immunother, vol. 27, No. 5, pp. 405-418, Sep.-Oct. 2004.

Kim, Do-Hyung, et al. "mTOR interacts with raptor to form a nutrient-sensitive complex that signals to the cell growth machinery." *Cell* 110.2 (2002): 163-175.

Kishore M, Cheung KCP, Fu H, Bonacina F, Wang G, Coe D, Ward EJ, Colamatteo A, Jangani M, Baragetti A, Matarese G, Smith DM, Haas R, Mauro C, Wraith DC, Okkenhaug K, Catapano AL, De Rosa V, Norata GD, Marelli-Berg FM. Regulatory T Cell Migration is Dependent on Glucokinase-Mediated Glycolysis. Immunity. 2017;47(5):875-889 e10.

Klapper et al., "Single-Pass, Closed-System Rapid Expansion of Lymphocyte Cultures for Adoptive Cell Therapy," Journal of Immunological Methods, 345, pp. 90-99, Apr. 21, 2009.

Klein, Elias, Eva Eichholz, and Don H. Yeager. "Affinity membranes prepared from hydrophilic coatings on microporous polysulfone hollow fibers." Journal of membrane science 90.1-2 (1994): 69-80.

Klysz D, Tai X, Robert PA, Craveiro M, Cretenet G, Oburoglu L, Mongellaz C, Floess S, Fritz V, Matias MI, Yong C, Surh N, Marie JC, Huehn J, Zimmermann V, Kinet S, Dardalhon V, Taylor N. Glutamine-dependent alpha-ketoglutarate production regulates the balance between T helper 1 cell and regulatory T cell generation. Sci Signal. 2015;8(396):ra97.

Korpanty et al., "Tageting Vascular Enothelium with Avidin Microbubbles," Ultrasound in Medicine and Biology, vol. 31, No. 9, pp. 1279-1283, May 24, 2005.

Krauss et al., "Signaling Takes a Breath—New Quantitative Perspectives on Bioenergetics and Signal Transduction," Immunity, vol. 15, pp. 497-502, Oct. 2001.

Kulikov, A. V., et al. "Application of multipotent mesenchymal stromal cells from human adipose tissue for compensation of neurological deficiency induced by 3-nitropropionic acid in rats." Bulletin of experimental biology and medicine 145.4 (2008): 514-519.

Kumar P, Marinelarena A, Raghunathan D, Ragothaman VK, Saini S, Bhattacharya P, Fan J, Epstein AL, Maker AV, Prabhakar BS. Critical role of OX40 signaling in the TCR-independent phase of human and murine thymic Treg generation. Cell Mol Immunol. 2019;16(2):138-153.

Kwan, J. and Borden, M., "Lipid Monolayer Collapse and Microbubble Stability," Advances in Colloid and Interface Science, vols. 183-184, pp. 82-99, Aug. 21, 2012.

Lampugnani MG, Caveda L, Breviario F, Del Maschio A, Dejana E. Endothelial cell-to-cell junctions. Structural characteristics and functional role in the regulation of vascular permeability and leukocyte extravasation. Bailliere's clinical haematology. 1993;6:539-558.

(56) References Cited

OTHER PUBLICATIONS

Lang, Julie, et al. "Generation of hematopoietic humanized mice in the newborn BALB/c-Rag2nullIl2rγnull mouse model: a multivariable optimization approach." Clinical Immunology 140.1 (2011): 102-116.

Lataillade, Jean-Jacques, et al. "Chemokine SDF-1 enhances circulating CD34+ cell proliferation in synergy with cytokines: possible role in progenitor survival." Blood, The Journal of the American Society of Hematology 95.3 (2000): 756-768.

Lee et al., "Continued Antigen Stimulation is Not Required During CD4+ T Cell Clonal Expansion," The Journal of Immunology, 168, pp. 1682-1689, 2002.

Lee III, Daniel W., et al. "Long-term outcomes following CD19 CAR T cell therapy for B-ALL are superior in patients receiving a fludarabine/cyclophosphamide preparative regimen and post-CAR hematopoietic stem cell transplantation." Blood 128.22 (2016): 218.

Lee, Jae W., et al. "Allogeneic human mesenchymal stem cells for treatment of E. coli endotoxin-induced acute lung injury in the ex vivo perfused human lung." Proceedings of the national academy of Sciences 106.38 (2009): 16357-16362.

Levine, B., "T Lymphocyte Engineering ex vivo for Cancer and Infectious Disease," Expert Opinion on Biological Therapy, vol. 4, No. 4, pp. 475-489, 2008.

Lindstein, Tullia, et al. "Regulation of lymphokine messenger RNA stability by a surface-mediated T cell activation pathway." Science 244.4902 (1989): 339-343.

Liotta, Francesco, et al. "Frequency of regulatory T cells in peripheral blood and in tumour-infiltrating lymphocytes correlates with poor prognosis in renal cell carcinoma." BJU international 107.9 (2011): 1500-1506.

Liu W, Putnam AL, Xu-Yu Z, Szot GL, Lee MR, Zhu S, Gottlieb PA, Kapranov P, Gingeras TR, Fazekas de St Groth B, Clayberger C, Soper DM, Ziegler SF, Bluestone JA. CD127 expression inversely correlates with FoxP3 and suppressive function of human CD4+ T reg cells. J Exp Med. 2006;203(7):1701-1711.

Lum et al., "Ultrasound Radiation Force Enables Targeted Deposition of Model Drug Carriers Loaded on Microbubbles," Journal of Controlled Release, 111, pp. 128-134, 2006.

M. R. Koller, et al. Clinical-scale human umbilical cord blood cell expansion in a novel automated perfusion culture system. Bone Marrow Transplantion 21:653-663, 1998.

Malin, Stephen F., et al. "Noninvasive prediction of glucose by near-infrared diffuse reflectance spectroscopy." (1999): 1651-1658.

Malone et al., "Characterization of Human Tumor-Infiltrating Lymphocytes Expanded in Hollow-Fiber Bioreactors for Immunotherapy of Cancer," Cancer Biotherapy & Radiopharmaceuticals, vol. 16, No. 5, pp. 381-390, 2001.

Mao AS, Mooney DJ (2015) Regenerative medicine: current therapies and future directions. Proc Natl Acad Sci USA 112(47): 14452-14459.

Marek-Trzonkowska, Natalia, et al. "Administration of CD4+CD25highCD127-regulatory T cells preserves β-cell function in type 1 diabetes in children." Diabetes care 35.9 (2012): 1817-1820.

Maria Streltsova, Dean Lee (Nationwide Children's Hospital, OSU, Columbus, OH) et al (Int'l Journal of Molecular Sciences, 2019).

Markgraf CG, Clifton GL, Aguirre M, Chaney SF, Knox-Du Bois C, Kennon K, Verma N. Injury severity and sensitivity to treatment after controlled cortical impact in rats. Journal of neurotrauma. 2001;18:175-186.

Mathew et al. A Phase I Clinical Trials I with Ex Vivo Expanded Recipient Regulatory T cells in Living Donor Kidney Transplants. Nature, Scientific Reports 8:7428 (1-12), 2018.

Mathew, James M., et al. "A phase I clinical trial with ex vivo expanded recipient regulatory T cells in living donor kidney transplants." Scientific reports 8.1 (2018): 1-12.

Matthay, Michael A., et al. "Therapeutic potential of mesenchymal stem cells for severe acute lung injury." Chest 138.4 (2010): 965-972.

Maynard CL, Harrington LE, Janowski KM, Oliver JR, Zindl CL, Rudensky AY, Weaver CT. Regulatory T cells expressing interleukin 10 develop from Foxp3+ and Foxp3-precursor cells in the absence of interleukin 10. Nat Immunol. 2007;8(9):931-41.

McKenna DH, Jr., Sumstad D, Kadidlo DM, et al. Optimization of cGMP purification and expansion of umbilical cord blood-derived T-regulatory cells in support of first-in-human clinical trials. Cytotherapy 2017;19:250-62.

McLimans W, Kinetics of Gas Diffusion in Mammalian Cell Culture Systems. Biotechnology and Bioengineering 1968; 10:725-740.

McMurtrey, Richard J. "Analytic models of oxygen and nutrient diffusion, metabolism dynamics, and architecture optimization in three-dimensional tissue constructs with applications and insights in cerebral organoids." Tissue Engineering Part C: Methods 22.3 (2016): 221-249.

Menge, Tyler, et al. "Mesenchymal stem cells regulate blood-brain barrier integrity through TIMP3 release after traumatic brain injury." Science translational medicine 4.161 (2012): 161ra150-161ra150.

Miska J, Lee-Chang C, Rashidi A, Muroski ME, Chang AL, Lopez-Rosas A, Zhang P, Panek WK, Cordero A, Han Y, Ahmed AU, Chandel NS, Lesniak MS. HIF-1alpha is a Metabolic Switch between Glycolytic-Driven Migration and Oxidative Phosphorylation-Driven Immunosuppression of Tregs in Glioblastoma. Cell Rep. 2019;27(1):226-237 e4.

Miyara M, Yoshioka Y, Kitoh A, Shima T, Wing K, Niwa A, Parizot C, Taflin C, Heike T, Valeyre D, Mathian A, Nakahata T, Yamaguchi T, Nomura T, Ono M, Amoura Z, Gorochov G, Sakaguchi S. Functional delineation and differentiation dynamics of human CD4+ T cells expressing the FoxP3 transcription factor. Immunity. 2009;30(6):899-911.

Murugappan, G., et al. "Human hematopoietic progenitor cells grow faster under rotational laminar flows." Biotechnology progress 26.5 (2010): 1465-1473.

Nankervis B, Jones M, Vang B et al. (2018) Optimizing T Cell Expansion in a Hollow-Fiber Bioreactor. Curr Stem Cell Rep. Advanced online publication. https://doi.org/10.1007/s40778-018-0116-x.

Nankervis, Brian, et al. "Optimizing T cell expansion in a hollow-fiber bioreactor." Current Stem Cell Reports 4.1 (2018): 46-51.

Nedoszytko B, Lange M, Sokolowska-Wojdylo M, Renke J, Trzonkowski P, Sobjanek M, Szczerkowska-Dobosz A, Niedoszytko M, Gorska A, Romantowski J, Czarny J, Skokowski J, Kalinowski L, Nowicki R. The role of regulatory T cells and genes involved in their differentiation in pathogenesis of selected inflammatory and neoplastic skin diseases. Part II: The Treg role in skin diseases pathogenesis. Postepy Dermatol Alergol. 2017;34(5):405-417.

Nehlin JO, Just M, Rustan AC (2011) Human myotubes from myoblast cultures undergoing senescence exhibit defects in glucose and lipid metabolism. Biogerontology 12: 349-365.

New victories for adult Stem Cell Research New York Feb. 6, 2007.

Newton R, Priyadharshini B, Turka LA. Immunometabolism of regulatory T cells. Nat Immunol. 2016;17(6):618-25.

Ng TH, Britton GJ, Hill EV, Verhagen J, Burton BR, Wraith DC. Regulation of adaptive immunity; the role of interleukin-10. Front Immunol. 2013;4:129.

Nikolaychik, V. V., M. M. Samet, and P. I. Lelkes. "A New, Cryoprecipitate Based Coating for Improved Endothelial Cell Attachment and Growth on Medical Grade Artificial Surfaces." ASAIO Journal (American Society for Artificial Internal Organs: 1992) 40.3 (1994): M846-52.

Nish SA, Schenten D, Wunderlich FT, Pope SD, Gao Y, Hoshi N, Yu S, Yan X, Lee HK, Pasman L, Brodsky I, Yordy B, Zhao H, Bruning J, Medzhitov R. T cell-intrinsic role of IL-6 signaling in primary and memory responses. Elife. 2014;3:e01949.

Niwayama, Jun, et al. "Analysis of hemodynamics during blood purification therapy using a newly developed noninvasive continuous monitoring method." Therapeutic Apheresis and Dialysis 10.4 (2006): 380-386.

Nugent, Helen M., et al. "Adventitial endothelial implants reduce matrix metalloproteinase-2 expression and increase luminal diameter in porcine arteriovenous grafts." Journal of vascular surgery 46.3 (2007): 548-556.

Okano et al (Tokyo Women's Medical College, Japan) demonstrated the recovery of endothelial cells and hepatocytes from

(56) References Cited

OTHER PUBLICATIONS plasma-treated polystyrene dishes grafted with PNIAAm (Journal of Biomedical Materials Research, 1993).

Onishi Y, Fehervari Z, Yamaguchi T, Sakaguchi S. Foxp3+ natural regulatory T cells preferentially form aggregates on dendritic cells in vitro and actively inhibit their maturation. Proc Natl Acad Sci U S A. 2008;105(29):10113-8.

Onyszchuk G, LeVine SM, Brooks WM, Berman NE. Post-acute pathological changes in the thalamus and internal capsule in aged mice following controlled cortical impact injury: A magnetic resonance imaging, iron histochemical, and glial immunohistochemical study. Neuroscience letters. 2009;452:204-208.

Pacella I, Procaccini C, Focaccetti C, Miacci S, Timperi E, Faicchia D, Severa M, Rizzo F, Coccia EM, Bonacina F, Mitro N, Norata GD, Rossetti G, Ranzani V, Pagani M, Giorda E, Wei Y, Matarese G, Barnaba V, Piconese S. Fatty acid metabolism complements glycolysis in the selective regulatory T cell expansion during tumor growth. Proc Natl Acad Sci U S A. 2018;115(28):E6546-E6555.

Parhi, Purnendu, Avantika Golas, and Erwin A. Vogler. "Role of Proteins and Water in the Initial Attachment of Mammalian Cells to Biomedical Surfaces: A Review." Journal of Adhesion Science and Technology 24.5 (2010): 853-888.

Pati S, Gerber MH, Menge TD, Wataha KA, Zhao Y, Baumgartner JA, Zhao J, Letourneau PA, Huby MP, Baer LA, Salsbury JR, Kozar RA, Wade CE, Walker PA, Dash PK, Cox CS, Jr., Doursout MF, Holcomb JB. Bone marrow derived mesenchymal stem cells inhibit inflammation and preserve vascular endothelial integrity in the lungs after hemorrhagic shock. PloS one. 2011;6:e25171.

Pati S, Khakoo AY, Zhao J, Jimenez F, Gerber MH, Harting M, Redell JB, Grill R, Matsuo Y, Guha S, Cox CS, Reitz MS, Holcomb JB, Dash PK. Human mesenchymal stem cells inhibit vascular permeability by modulating vascular endothelial cadherin/beta-catenin signaling. Stem cells and development. 2011;20:89-101.

Pati, Shibani, and Todd E. Rasmussen. "Cellular therapies in trauma and critical care medicine: Looking towards the future." *PLoS Medicine* 14.7 (2017): e1002343.

Pati, Shibani, et al. "Lyophilized plasma attenuates vascular permeability, inflammation and lung injury in hemorrhagic shock." *PloS one* 13.2 (2018): e0192363.

Peters JH, Preijers FW, Woestenenk R, Hilbrands LB, Koenen HJ, Joosten I. Clinical grade Treg: GMP isolation, improvement of purity by CD127 Depletion, Treg expansion, and Treg cryopreservation. PLoS One. 2008;3(9):e3161.

Peters, R.; Jones, M.; Brecheisen, M.; Startz, T.; Vang, B.; Nankervis, B.; Frank, N.; Nguyen, K. (2012) TerumoBCT. https://www.terumobct.com/location/north-america/products-and-services/Pages/Quantum-Materials.aspx.

Porter CM, Horvath-Arcidiacono JA, Singh AK, Horvath KA, Bloom ET, Mohiuddin MM. Characterization and expansion of baboon CD4+CD25+ Treg cells for potential use in a non-human primate xenotransplantation model. Xenotransplantation. 2007;14(4):298-308.

Povsic TJ, O'Connor CM, Henry T, et al. (2011) A double-blind, randomized, controlled, multicenter study to assess the safety and cardiovascular effects of skeletal myoblast implantation by catheter delivery in patients with chronic heart failure after myocardial infarction. Am Heart J 162(4): 654-662.

Prockop, Darwin J., Carl A. Gregory, and Jeffery L. Spees. "One strategy for cell and gene therapy: harnessing the power of adult stem cells to repair tissues." Proceedings of the National Academy of Sciences 100.suppl_1 (2003): 11917-11923.

Q. L. Hao, et al. A functional comparison of CD34+ CD38= cells in cord blood and bone marrow. Blood 86:3745-3753, 1995.

Rahmahwati, Nurlaela, Deana Wahyuningrum, and Anita Alni. "The Synthesis of Polyethersulfone (PES) Derivatives for the Immobilization of Lipase Enzyme." Key Engineering Materials. vol. 811. Trans Tech Publications Ltd, 2019.

Rey-Jurado, Emma, et al. "Assessing the importance of domestic vaccine manufacturing centers: an overview of immunization programs, vaccine manufacture, and distribution." Frontiers in immunology 9 (2018): 26.

Roballo KC, Dhungana S, Z. J, Oakey J, Bushman J. Localized delivery of immunosuppressive regulatory T cells to peripheral nerve allografts promotes regeneration of branched segmental defects. Biomaterials. 2019;209:1-9.

Rodrigues, C., Fernandes, T., Diogo, M., Lobato da Silva, C., Cabral, J. Stem Cell Cultivation in Bioreactors. 2011. Biotechnology Advances v. 29, pp. 815-829.

Ronco C1, Levin N, Brendolan A, Nalesso F, Cruz D, Ocampo C, Kuang D, Bonello M, De Cal M, Corradi V, Ricci Z. Flow distribution analysis by helical scanning in polysulfone hemodialyzers: effects of fiber structure and design on flow patterns and solute clearances. Hemodial Int. Oct. 2006; 10(4):380-8.

Ronco, C., Brendolan, A., Crepaldi, C., Todighiero, M., Scabardi, M. Blood and Dialysate Flow Distributions in Hollow-Fiber Hemodialyzers Analyzed by Computerized Helical Scanning Technique. 2002. Journal of the American Society of Nephrology. V. 13, pp. S53-S61.

Rosenblum MD, Way SS, Abbas AK. Regulatory T cell memory. Nat Rev Immunol. 2016;16(2):90-101.

Rubtsov YP, Rasmussen JP, Chi EY, Fontenot J, Castelli L, Ye X, Treuting P, Siewe L, Roers A, Henderson WR, Jr., Muller W, Rudensky AY. Regulatory T cell-derived interleukin-10 limits inflammation at environmental interfaces. Immunity. 2008;28(4):546-58.

Rudensky, Alexander Y. "Regulatory T cells and Foxp3." Immunological reviews 241.1 (2011): 260-268.

Ryu, Min-Hyung, and Mark Gomelsky. "Near-infrared light responsive synthetic c-di-GMP module for optogenetic applications." ACS synthetic biology 3.11 (2014): 802-810.

S. Koestenbauer, et al. Protocols for Hematopoietic Stem Cell Expansion from Umbilical Cord Blood. Cell Transplantation 18: 1059-1068, 2009.

S. L. Smith, et al. Expansion of neutrophil precursors and progenitors in suspension cultures of CD34+ cells enriched from human bone marrow. Experimental Hematology 21:870-877, 1993.

Safinia N, Grageda N, Scotta C, Thirkell S, Fry LJ, Vaikunthanathan T, Lechler RI, Lombardi G. Cell Therapy in Organ Transplantation: Our Experience on the Clinical Translation of Regulatory T Cells. Front Immunol. 2018;9:354.

Sahay A, Scobie KN, Hill AS, O'Carroll CM, Kheirbek MA, Burghardt NS, Fenton AA, Dranovsky A, Hen R. Increasing adult hippocampal neurogenesis is sufficient to improve pattern separation. Nature. 2011;472:466-470.

Sakaguchi S, Sakaguchi N, Asano M, Itoh M, Toda M. Immunologic self-tolerance maintained by activated T cells expressing IL-2 receptor alpha-chains (CD25). Breakdown of a single mechanism of self-tolerance causes various autoimmune diseases. J Immunol. 1995;155(3):1151-64.

Sakaguchi S, Sakaguchi N, Shimizu J, Yamazaki S, Sakihama T, Itoh M, Kuniyasu Y, Nomura T, Toda M, Takahashi T. Immunologic tolerance maintained by CD25+ CD4+ regulatory T cells: their common role in controlling autoimmunity, tumor immunity, and transplantation tolerance. Immunol Rev. 2001;182:18-32.

Schild, Howard G. "Poly (N-isopropylacrylamide): experiment, theory and application." Progress in polymer science 17.2 (1992): 163-249.

Schmitz R, Alessio A, Kina P. The Physics of PET/CT scanners. Imaging Research Laboratory, Department of Radiology, University of Washington http://depts.washington.edu/imreslab/education/Physics%20of%20PET.pdf.

Schwartz RH. T cell anergy. Annu Rev Immunol. 2003;21:305-34.

Shevkoplyas et al., "The Force Acting on a Superparamagnetic Bead due to an Applied Magnetic Field," Lab on a Chip, 7, pp. 1294-1302, 2007.

Shimazu Y, Shimazu Y, Hishizawa M, Hamaguchi M, Nagai Y, Sugino N, Fujii S, Kawahara M, Kadowaki N, Nishikawa H, Sakaguchi S, Takaori-Kondo A. Hypomethylation of the Treg-Specific Demethylated Region in FOXP3 is a Hallmark of the Regulatory T-cell Subtype in Adult T-cell Leukemia. Cancer Immunol Res. 2016;4(2):136-45.

(56) References Cited

OTHER PUBLICATIONS

Shimizu et al (TWMU & Heart Institute of Japan) described the detachment of avian cardiomyocytes from PIPAAm matrixes that were observed to pulse spontaneously with neovascularization in layered sheets three (3) weeks after transplantation (Circulation Research, 2002).
Sigma-Aldrich Cheimcals Mitomycin C (M4287) Msds, v4.4, Jul. 7, 2011.
Sirsi, S. and Borden, M., "Microbubble Composition, Properties, and Biomedical Applications," Bubble Science, Engineering & Technolology, vol. 1, No. 1-2, pp. 3-17, 2009.
Smith C, Okern G, Rehan S, et al. Ex vivo expansion of human T cells for adoptive immunotherapy using the novel Xeno-free CTS Immune Cell Serum Replacement. Clinical & Translational Immunology 2015;4:e31.
Somerville et al., "Clinical Scale Rapid Expansion of Lymphocytes for Adoptive Cell Transfer Therapy in the Wave® Bioreactor," Journal of Translational Medicine, vol. 10, No. 69, pp. 1-11, 2012.
Somerville, R. and Dudley, M., "Bioreactors Get Personal," Oncolmmunology, vol. 1, No. 8, pp. 1435-1437, Nov. 2012.
Spectrum Labs KrosFlo Research IIi TFF System, undated, Spectrum Laboratories, Inc., 4 pages.
Stafano Tiziani, et al. Metabolomic Profiling of Drug Response in Acute Myeloid Leukaemia Cell lines. PLOSone 4(1): e4251 (Jan. 22, 2009).
StAR_Abstract, undated, author unknown, 1 page.
Startz et al May 2016 TBCT T-cell White Paper.
Startz, T., et al. "Maturation of dendritic cells from CD14+ monocytes in an automated functionally closed hollow fiber bioreactor system." Cytotherapy 16.4 (2014): S29.
Steven M. Bryce, et al (Litron Laboratories). In vitro micronucleus assay scored by flow cytometry provides a comprehensive evaluation of cytogenetic damage and cytotoxicity. Mutation Research 630(1-2): 78-91, 2007.
Steven M. Bryce, et al (Novartis Pharma AG, Johnson & Johnson Pharmaceutical Research, GlaxoSmithKline). Interlaboratory evaluation of a flow cytometric, high content in vitro micronucleus assay. Genetic Toxicology and Environmental Mutagenesis 650: 181-195, 2008.
Stuart, Martien A. Cohen, et al. "Emerging applications of stimuli-responsive polymer materials." Nature materials 9.2 (2010): 101-113.
Su LF, Del Alcazar D, Stelekati E, Wherry EJ, Davis MM. Antigen exposure shapes the ratio between antigen-specific Tregs and conventional T cells in human peripheral blood. Proc Natl Acad Sci U S A. 2016;113(41):E6192-E6198.
Takezawa, Toshiaki, Yuichi Mori, and Katsutoshi Yoshizato. "Cell culture on a thermo-responsive polymer surface." Bio/technology 8.9 (1990): 854-856.
The effect of rocking rate and angle on T cell cultures grown in Xuri™ Cell Expansion Systems, Aug. 2014, GE Healthcare UK Limited, 4 pages.
Trzonkowski et al., "Ex Vivo Expansion of CD4+ CD25+ T Regulatory Cells for Immunosuppressive Therapy," Cytometry Part A, 75A, pp. 175-188, 2009.
Trzonkowski, Piotr, et al. "First-in-man clinical results of the treatment of patients with graft versus host disease with human ex vivo expanded CD4+ CD25+ CD127? T regulatory cells." Clinical immunology 133.1 (2009): 22-26.
Tsvetkov, Ts, et al. "Isolation and cryopreservation of human peripheral blood monocytes." Cryobiology 23.6 (1986): 531-536.
Ueda, Ryosuke, et al. "Interaction of natural killer cells with neutrophils exerts a significant antitumor immunity in hematopoietic stem cell transplantation recipients." Cancer medicine 5.1 (2015): 49-60.
Underwood, P. Anne, et al. "Effects of base material, plasma proteins and FGF2 on endothelial cell adhesion and growth." Journal of Biomaterials Science, Polymer Edition 13.8 (2002): 845-862.

Urbich, et al from the Goethe-Universität, demonstrated that human endothelial cells increased VEGFR-2 mRNA expression when exposed to 5-15 dynes/cm2 of constant shear force for a period of 6-24 hours (FEBS, 2002).
Van der Net JB, Bushell A, Wood KJ, Harden PN. Regulatory T cells: first steps of clinical application in solid organ transplantation. Transpl Int. 2016;29(1):3-11.
Van der Windt GJ, Pearce EL. Metabolic switching and fuel choice during T-cell differentiation and memory development. Immunol Rev. 2012;249(1):27-42.
Vera et al., "Accelerated Production of Antigen-Specific T-Cells for Pre-Clinical and Clinical Applications Using Gas-Permeable Rapid Expansion Cultureware (G-Rex)," J Immunother, vol. 33, No. 3, pp. 305-315, Apr. 2010.
Villa, Alma Y. Camacho, et al. "CD133+ CD34+ and CD133+ CD38+ blood progenitor cells as predictors of platelet engraftment in patients undergoing autologous peripheral blood stem cell transplantation." Transfusion and Apheresis Science 46.3 (2012): 239-244.
Visser EP1, Disselhorst JA, Brom M, Laverman P, Gotthardt M, Oyen WJ, Boerman OC. Spatial resolution and sensitivity of the Inveon small-animal PET scanner. J Nucl Med. Jan. 2009;50(1):139-47.
Von Laer, D., et al. "Loss of CD38 antigen on CD34+ CD38+ cells during short-term culture." Leukemia 14.5 (2000): 947-948.
Wagner Jr, John E., et al. "Phase I/II trial of StemRegenin-1 expanded umbilical cord blood hematopoietic stem cells supports testing as a stand-alone graft." Cell stem cell 18.1 (2016): 144-155.
Walker, Peter A., et al. "Direct intrathecal implantation of mesenchymal stromal cells leads to enhanced neuroprotection via an NF?B-mediated increase in interleukin-β production." Stem cells and development 19.6 (2010): 867-876.
Wang R, Dillon CP, Shi LZ, Milasta S, Carter R, Finkelstein D, McCormick LL, Fitzgerald P, Chi H, Munger J, Green DR. The transcription factor Myc controls metabolic reprogramming upon T lymphocyte activation. Immunity. 2011;35(6):871-82.
Wang, Jiamian, John A. Jansen, and Fang Yang. "Electrospraying: possibilities and challenges of engineering carriers for biomedical applications—a mini review." Frontiers in Chemistry 7 (2019): 258.
Ward H, Vigues S, Poole S, Bristow AF. The rat interleukin 10 receptor: cloning and sequencing of cDNA coding for the alpha-chain protein sequence, and demonstration by western blotting of expression in the rat brain. Cytokine. 2001;15(5):237-40.
Wawman, Rebecca Ellen, Helen Bartlett, and Ye Htun Oo. "Regulatory T cell metabolism in the hepatic microenvironment." Frontiers in immunology 8 (2018): 1889.
Weber et al., "White Paper on Adoptive Cell Therapy for Cancer with Tumor-Infiltrating Lymphocytes: A Report of the CTEP Subcommittee on Adoptive Cell Therapy," Clinical Cancer Research, vol. 17, No. 7, pp. 1664-1673, Apr. 1, 2011.
Weiss RA, Weiss MA, Beasley KL, Munavalli G (2007) Autologous cultured fibroblast injection for facial contour deformities: a prospective, placebo-controlled, Phase III clinical trial. Dermatol Surg 33(3): 263-268.
Widdel, F. 2010. "Theory and measurement of bacterial growth" http://www.mpi-bremen.de/Binaries/Binary13037/Wachstumsversuch.pdf.
Yamada, Noriko, et al. "Thermo?responsive polymeric surfaces; control of attachment and detachment of cultured cells." Die Makromolekulare Chemie, Rapid Communications 11.11 (1990): 571-576.
Yang, Hee Seok, et al. "Suspension culture of mammalian cells using thermosensitive microcarrier that allows cell detachment without proteolytic enzyme treatment." Cell transplantation 19.9 (2010): 1123-1132.
Yi, Zhuan, et al. "A readily modified polyethersulfone with amino-substituted groups: its amphiphilic copolymer synthesis and membrane application." Polymer 53.2 (2012): 350-358.
Yoshinari, Masao, et al. "Effect of cold plasma-surface modification on surface wettability and initial cell attachment." International Journal of Biomedical and Biological Engineering 3.10 (2009): 507-511.

(56) References Cited

OTHER PUBLICATIONS

Zappasodi et al., "The Effect of Artificial Antigen-Presenting Cells with Preclustered Anit-CD28/-CD3/LFA-1 Monoclonal Antibodies on the Induction of ex vivo Expansion of Functional Human Antitumor T Cells," Haematologica, vol. 93, No. 10, pp. 1523-1534, 2008.

Zemmour D, Zilionis R, Kiner E, Klein AM, Mathis D, Benoist C. Publisher Correction: Single-cell gene expression reveals a landscape of regulatory T cell phenotypes shaped by the TCR. Nat Immunol. 2018; 19(6):645.

Zeng B, Kwak-Kim J, Liu Y, Liao AH. Treg cells are negatively correlated with increased memory B cells in pre-eclampsia while maintaining suppressive function on autologous B-cell proliferation. Am J Reprod Immunol. 2013;70(6):454-63.

Zheng, et al at the University of Iowa have shown that the differential effects of pulsatile blood flow and cyclic stretch are an important growth stimulus (American Journal of Physiology—Heart and Circulatory Physiology, 2008).

\* cited by examiner

| IC Inlet: (100mL SDE CPPT) | Step 1 | Step 2 | Step 3 |
|---|---|---|---|
| IC Inlet Rate (mL/min) | Reagent | Wash | Wash |
| IC Circulation Rate (mL/min) | 10 | 10 | 50 |
| EC Inlet | 100 | 100 | -25 |
| EC Inlet Rate (mL/min) | None | None | Wash |
| EC Circulation Rate (mL/min) | 0 | 0 | 0.1 |
| Outlet | 30 | 30 | 30 |
| Rocker Control | EC Outlet | EC Outlet | EC Outlet |
| Stop Condition | Stationary (0) | Stationary (0) | Stationary (0) |
| | Empty Bag | IC Volume: 22mL | Time: 10.0 min |

FIG. 8C

METHODS AND SYSTEMS FOR COATING A CELL GROWTH SURFACE

CROSS-REFERENCE TO RELATED APPLICATION

This application is a divisional application of, and claims priority to, U.S. patent application Ser. No. 15/616,635, entitled, "Methods and Systems for Coating a Cell Growth Surface," filed on Jun. 7, 2017, which claims priority to, and the benefit of, U.S. Provisional Application Ser. No. 62/347,025, filed on Jun. 7, 2016, and entitled, "Growth Surface Coating." The disclosures of the above-identified applications are hereby incorporated by reference in their entireties as if set forth herein in full for all that they teach and for all purposes.

BACKGROUND

Cell Expansion Systems (CESs) may be used to expand and differentiate cells. Cell expansion systems may be used to expand, e.g., grow, a variety of adherent and suspension cells. For example, cell expansion systems may be used to expand mesenchymal stem cells (MSCs) and other types of cells, such as bone marrow cells. Stem cells which are expanded from donor cells may be used to repair or replace damaged or defective tissues and have broad clinical applications for a wide range of diseases. Cells, of both adherent and non-adherent type, may be grown in a bioreactor in a cell expansion system.

SUMMARY

Embodiments of the present disclosure generally relate to a cell expansion system for expanding cells. Such expansion may occur through the use of a bioreactor or cell growth chamber comprising a hollow fiber membrane. In embodiments, a hollow fiber membrane comprises a plurality of hollow fibers. Such hollow fiber membrane may include an extracapillary (EC) space and an intracapillary (IC) space. A cell expansion system may expand a variety of cell types, such as mesenchymal stem cells, cancer cells, T-cells, fibroblasts, and myoblasts. In expanding cells, a compound or coating agent may be applied to a cell growth surface. For example, an adherence-promoting compound may be applied to a cell growth surface to promote contact, e.g., adherence, and subsequent expansion of cells, such as a cell line including human mesenchymal stem cells (hMSCs). In embodiments, for cells to adhere to the surface of the hollow fibers, the surface may be modified in some way, such as by coating at least the cell growth surface with a protein, for example. In embodiments, a coating agent may be applied to the inner surface or inner aspect of bioreactor fibers. For example, a coating agent may be applied to the intracapillary (IC) surface of a hollow fiber(s). In another embodiment, a coating agent may be applied to the extracapillary (EC) surface of a hollow fiber(s). As an example of a coating agent(s), cryoprecipitate (CPPT), fibronectin (FN), human fibronectin (hFN), and/or combinations of such coating agents may be used. In other embodiments, a plurality of coating agents, or a combination of coating agent(s), may be used.

Embodiments provide for fluid movement in a cell growth chamber or bioreactor to be controlled to actively promote a coating agent(s) to a cell growth surface, e.g., to a surface of a hollow fiber(s). For example, such fluid movement may be controlled so as to move fluid from one side, e.g., IC side, of a hollow fiber to the other side, e.g., EC side, of the hollow fiber. In an embodiment, ultrafiltration may be used to move fluid in a bioreactor. For example, positive ultrafiltration may be used to move fluid from the IC side of a bioreactor to the EC side of the bioreactor. In another embodiment, negative ultrafiltration may be used to move fluid from the EC side of a bioreactor to the IC side of the bioreactor. In embodiments, other types of ultrafiltration or directions of fluid movement may be used. The direction of fluid movement may depend on the surface upon which cells are being expanded.

By controlling fluid movement, a coating solution, e.g., a fluid(s) and a coating agent(s), may be actively pushed to the IC (or EC) loop, and the fluid(s) may be pushed through the pores, for example, of a hollow fiber(s), leaving a residual layer of adherence-promoting protein(s), for example, on the IC (or EC) side of the hollow fiber(s) and therefore facilitating the contact, e.g., attachment, of cells, e.g., adherent cells. Such fluid movement, e.g., ultrafiltration, may decrease the time required for a chemical reaction between a coating agent and the growth surface of the bioreactor to occur to coat the fiber(s). Such fluid movement may be controlled through the adjusting of one or more valve(s), pump(s), or other type of fluid flow control device(s).

Embodiments of the present disclosure provide for implementing such coating procedure(s) through the use of one or more protocols or tasks for use with a cell expansion system. Such protocols or tasks may include pre-programmed protocols or tasks for use with an automated CES, for example. In embodiments, a pre-programmed, default, or otherwise previously saved task may be selected. A task may comprise one or more steps. In other embodiments, such protocols or tasks may include custom or user-defined protocols or tasks for use with an automated CES, for example. Through a user interface (UI) and graphical user interface (GUI) elements, a custom or user-defined protocol or task may be created. In embodiments, a combination of pre-programmed, default, custom, and/or user-defined tasks, for example, may be used.

This Summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items.

FIG. 8C illustrates example steps and parameters for applying an agent to a cell growth surface in accordance with an embodiment of the present disclosure.

DETAILED DESCRIPTION

Figure 1A:
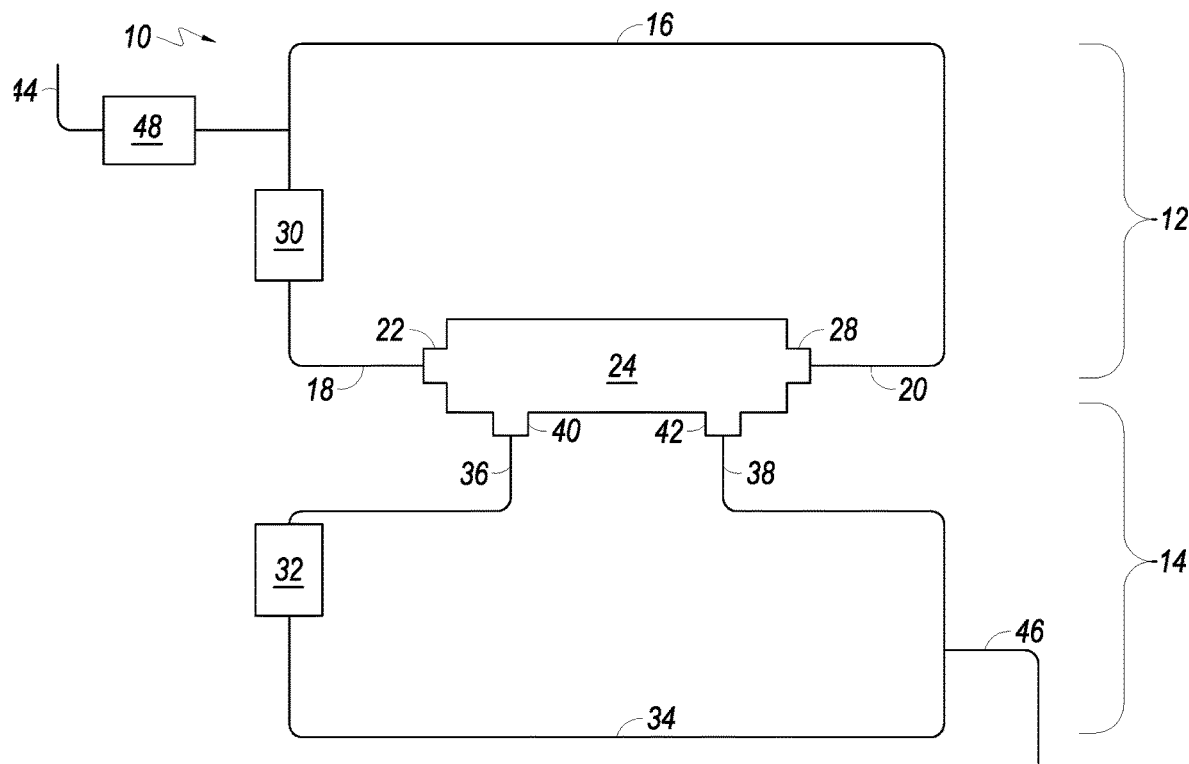
FIG. 1A depicts an embodiment of a cell expansion system (CES).

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will appreciate that other embodiments, including improvements, are within the spirit and scope of the present disclosure. Further, any alternatives or additions, including any listed as separate embodiments, may be used or incorporated with any other embodiments herein described.

Embodiments of the present disclosure are generally directed to methods and systems for applying a coating agent or reagent to a cell growth surface to promote cell contact, e.g., adherence, and subsequent expansion of cells. In an embodiment, such application comprises an active promotion of a coating agent or reagent to the cell growth surface, such as the cell growth surface of a hollow fiber(s) where a hollow fiber bioreactor may be used for cell expansion in a cell expansion system. Controlling fluid movement in a bioreactor or cell growth chamber allows for the active promotion of a coating agent or reagent to a cell growth surface.

Passive coating processes may involve the passive application of a coating agent to a cell growth surface, in which a coating agent(s) may be passively applied to a cell growth chamber of an automated cell expansion system using circulating flow, for example. A coating agent(s) may be loaded into an intracapillary or extracapillary side of a bioreactor, for example. The coating agent(s) may then be circulated in the intracapillary or extracapillary loop for a particular, e.g., first, time period. As such, the bioreactor may be passively coated using circulating flow in the IC (or EC) loop, in which such process may take multiple hours, for example. Such coating procedure may take from about four (4) hours to about twenty-four (24) hours, for example, of circulation of a coating agent to achieve coating of the cell growth surface. As an example, a bioreactor coating protocol may load a coating agent into the intracapillary side of a bioreactor in a cell expansion system. The coating agent may then be circulated in the intracapillary circulation loop for a minimum of sixteen (16) hours. A user utilizing such process may therefore use at least two cell expansion systems, in which the user may begin, in a second cell expansion system, any additional expansion of a population of cells harvested from a first cell expansion system (where cells may not be stored in a non-cryopreserved state for up to sixteen (16) hours, for example).

Embodiments herein provide for the active pushing or active promotion of a coating agent solution to a cell growth surface. Rather than passively coating the bioreactor using circulating flow in the IC loop, for example, for many hours, a coating solution, e.g., a fluid(s) and a coating agent(s), can be actively pushed into the IC loop, and the fluid(s) may be pushed through the pores of the bioreactor, leaving a residual layer of adherence promoting proteins on the IC side of the bioreactor fibers to facilitate the attachment of adherent cells. In an embodiment, ultrafiltration may be used to allow a coating agent or reagent to be promoted to the growth surface of a hollow fiber, for example. Ultrafiltration, e.g., positive ultrafiltration, may be used to move fluid from a first side of a hollow fiber to a second side of a hollow fiber. For example, utilizing positive ultrafiltration of a fluid, the fluid may be moved from the IC side of a hollow fiber or hollow fiber membrane to the EC side of the hollow fiber or hollow fiber membrane. Such fluid movement may decrease the time it takes for a chemical reaction to occur between a coating agent or reagent and a growth surface of the bioreactor to coat the cell growth surface. The molecular barrier created by the specified construction of the hollow fibers in the bioreactor may be such that the coating agent or reagent may not be able to pass through the fiber wall along with the fluid in which it is suspended. The adherence promoting proteins of the coating agent may remain in a residual layer on a first side of the hollow fiber(s) as the solution is pushed through the pores of the fibers to a second side of the hollow fiber(s). Moving the fluid using ultrafiltration, e.g., positive ultrafiltration, may thus result in "actively" promoting the coating agent or reagent to the surface of the hollow fiber(s), according to embodiments.

For example, a coating agent(s) may be introduced to the fibers of a hollow fiber bioreactor on the IC (or EC) side. Such coating agent(s) may be suspended in a solution, e.g., coating solution. The IC outlet or waste valve may be closed, with the EC outlet or waste valve open. The IC inlet rate may be set to wash the IC side with media, such as phosphate buffered saline (PBS), for example. Such fluid may have no pathway but through the pores of the fibers (IC outlet valve closed). Accordingly, the solution may flow through the pores of the fibers from the IC side to the EC side. The coating agent, e.g., CPPT, may be hydrostatically deposited onto the inner wall(s) of the bioreactor fiber for a defined time period. For example, such time period may be about ten (10) minutes, according to an embodiment. Such membrane ultrafiltration method allows adherence promoting proteins to be physisorbed on the bioreactor fibers as the solution flows through the pores of the fiber from the IC side to the EC side, for example.

In an embodiment, such active moving of the coating agent to the cell growth surface(s) may significantly decrease the amount of time it may take to coat the cell growth surface as compared to other methods of coating a cell growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc.

Embodiments are directed to a cell expansion system, as described above. In embodiments, such cell expansion system is closed, in which a closed cell expansion system comprises contents that are not directly exposed to the atmosphere. Such cell expansion system may be automated. In embodiments, cells, of both adherent and non-adherent or suspension type, may be grown in a bioreactor in the cell expansion system. According to embodiments, the cell expansion system may include base media or other type of media. Methods for replenishment of media are provided for cell growth occurring in a bioreactor of the closed cell expansion system. In embodiments, the bioreactor used with such systems is a hollow fiber bioreactor. Many types of bioreactors may be used in accordance with embodiments of the present disclosure.

The system may include, in embodiments, a bioreactor that further includes a first fluid flow path having at least opposing ends, a first opposing end of the first fluid flow path fluidly associated with a first port of a hollow fiber membrane and a second end of the first fluid flow path fluidly associated with a second port of the hollow fiber membrane, in which the first fluid flow path comprises an intracapillary portion of the hollow fiber membrane. In embodiments, a hollow fiber membrane comprises a plurality of hollow fibers. The system may further include a fluid inlet path fluidly associated with the first fluid flow path, in which a plurality of cells are introduced into the first fluid flow path through a first fluid inlet path. A first pump for circulating fluid in the first fluid flow path of the bioreactor may also be included. In embodiments, the system includes a controller for controlling operation of the first pump. In an embodiment, the controller is a computing system, including a processor, for example. The controller is configured, in embodiments, to control the pump to circulate a fluid at a first rate within the first fluid flow path. In some embodiments, a second pump for transferring intracapillary inlet fluid from an intracapillary media bag to the first fluid flow path and a second controller for controlling operation of the second pump are included. The second controller, in embodiments, controls the second pump to transfer cells from a cell inlet bag to the first fluid flow path, for example. Additional controllers, e.g., third controller, fourth controller, fifth controller, sixth controller, etc., may be used in accordance with embodiments. Further, additional pumps, e.g., third pump, fourth pump, fifth pump, sixth pump, etc., may be used in accordance with embodiments of the present disclosure. In addition, while the present disclosure may refer to a media bag, a cell inlet bag, etc., multiple bags, e.g., a first media bag, a second media bag, a third media bag, a first cell inlet bag, a second cell inlet bag, a third cell inlet bag, etc., and/or other types of containers, may be used in embodiments. In other embodiments, a single media bag, a single cell inlet bag, etc., may be used. Further, additional or other fluid paths, e.g., a second fluid flow path, a second fluid inlet path, etc., may be included in embodiments.

In other embodiments, the system is controlled by, for example: a processor coupled to the cell expansion system; a display device, in communication with the processor, and operable to display data; and a memory, in communication with and readable by the processor, and containing a series of instructions. In embodiments, when the instructions are executed by the processor, the processor receives an instruction to coat the bioreactor, for example. In response to the instruction to coat the bioreactor, the processor may execute a series of steps to coat the bioreactor and may next receive an instruction to load cells into the bioreactor, for example. In response to the instruction to load cells, the processor may execute a series of steps to load the cells from a cell inlet bag, for example, into the bioreactor.

A schematic of an example cell expansion system (CES) is depicted in FIG. 1A, in accordance with embodiments of the present disclosure. CES 10 includes first fluid circulation path 12 and second fluid circulation path 14. First fluid flow path 16 has at least opposing ends 18 and 20 fluidly associated with a hollow fiber cell growth chamber 24 (also referred to herein as a "bioreactor"), according to embodiments. Specifically, opposing end 18 may be fluidly associated with a first inlet 22 of cell growth chamber 24, and opposing end 20 may be fluidly associated with first outlet 28 of cell growth chamber 24. Fluid in first circulation path 12 flows through the interior of hollow fibers 116 (see FIG. 1B) of hollow fiber membrane 117 (see FIG. 1B) disposed in cell growth chamber 24 (cell growth chambers and hollow fiber membranes are described in more detail infra). Further, first fluid flow control device 30 may be operably connected to first fluid flow path 16 and may control the flow of fluid in first circulation path 12.

Second fluid circulation path 14 includes second fluid flow path 34, cell growth chamber 24, and a second fluid flow control device 32. The second fluid flow path 34 has at least opposing ends 36 and 38, according to embodiments.

Opposing ends 36 and 38 of second fluid flow path 34 may be fluidly associated with inlet port 40 and outlet port 42 respectively of cell growth chamber 24. Fluid flowing through cell growth chamber 24 may be in contact with the outside of hollow fiber membrane 117 (see FIG. 1B) in the cell growth chamber 24, in which a hollow fiber membrane comprises a plurality of hollow fibers. Second fluid circulation path 14 may be operably connected to second fluid flow control device 32.

Figure 1B:
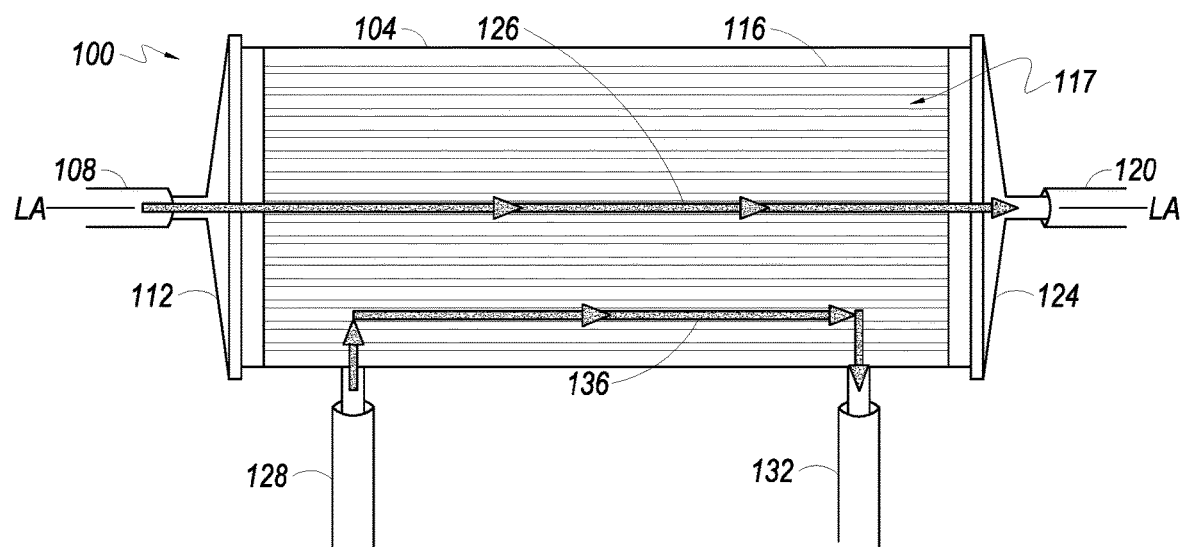
FIG. 1B illustrates a front elevation view of an embodiment of a bioreactor showing circulation paths through the bioreactor.

First and second fluid circulation paths 12 and 14 may thus be separated in cell growth chamber 24 by a hollow fiber membrane 117 (see FIG. 1B). Fluid in first fluid circulation path 12 flows through the intracapillary ("IC") space of the hollow fibers in the cell growth chamber 24. First circulation path 12 may be referred to as the "IC loop." Fluid in second circulation path 14 flows through the extracapillary ("EC") space in the cell growth chamber 24. Second fluid circulation path 14 may be referred to as the "EC loop." Fluid in first fluid circulation path 12 may flow in either a co-current or counter-current direction with respect to the flow of fluid in second fluid circulation path 14, according to embodiments.

Fluid inlet path 44 may be fluidly associated with first fluid circulation path 12. Fluid inlet path 44 allows fluid into first fluid circulation path 12, while fluid outlet path 46 allows fluid to leave CES 10. Third fluid flow control device 48 may be operably associated with fluid inlet path 44. Alternatively, third fluid flow control device 48 may alternatively be associated with first outlet path 46.

Fluid flow control devices as used herein may comprise a pump, valve, clamp, or combination thereof, according to embodiments. Multiple pumps, valves, and/or clamps can be arranged in any combination. In various embodiments, the fluid flow control device is or includes a peristaltic pump. In embodiments, fluid circulation paths, inlet ports, and outlet ports may be constructed of tubing of any material.

Various components are referred to herein as "operably associated." As used herein, "operably associated" refers to components that are linked together in operable fashion and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g., a peristaltic pump that pumps fluids through flexible tubing by compressing the exterior of the tube).

Generally, any kind of fluid, including buffers, protein containing fluid, and cell-containing fluid, for example, can flow through the various circulations paths, inlet paths, and outlet paths. As used herein, "fluid," "media," and "fluid media" are used interchangeably.

Turning to FIG. 1B, an example of a hollow fiber cell growth chamber 100 which may be used with the present disclosure is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132.

According to embodiments of the present disclosure, fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116 comprising hollow fiber membrane 117, and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber 100 via the EC inlet port 128 may be in contact with the outside of the hollow fibers 116. Small molecules (e.g., ions, water, oxygen, lactate, etc.) may diffuse through the hollow fibers 116 from the interior or IC space of the hollow fiber to the exterior or EC space, or from the EC space to the IC space. Large molecular weight molecules, such as growth factors, are typically too large to pass through the hollow fiber membrane, and may remain in the IC space of the hollow fibers 116. The media may be replaced as needed, in embodiments. Media may also be circulated through an oxygenator or gas transfer module to exchange gasses as needed. Cells may be contained within a first circulation path and/or a second circulation path, as described below, and may be on either the IC side and/or EC side of the membrane, according to embodiments.

The material used to make the hollow fiber membrane 117 may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein such as fibronectin or collagen, for example, or by exposing the surface to radiation, according to embodiments. Gamma treating the membrane surface allows for attachment of adherent cells without additionally coating the membrane with fibronectin, cryoprecipitate, or the like. Bioreactors made of gamma treated membranes may be reused. Other coatings and/or treatments for cell attachment may be used in accordance with embodiments of the present disclosure.

Figure 1C:
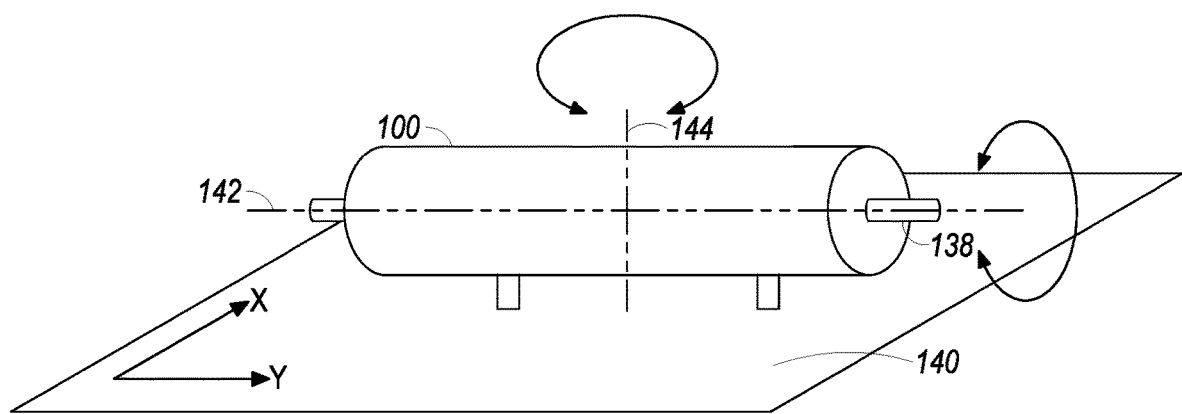
FIG. 1C depicts a rocking device for moving a cell growth chamber rotationally or laterally during operation of a cell expansion system, according to embodiments of the present disclosure.

In embodiments, the CES (such as CES 500 (see FIG. 5) and/or CES 600 (see FIG. 6), for example) may include a device configured to move or "rock" the cell growth chamber relative to other components of the cell expansion system by attaching it to a rotational and/or lateral rocking device. FIG. 1C shows one such device, in which a bioreactor 100 may be rotationally connected to two rotational rocking components and to a lateral rocking component, according to an embodiment.

A first rotational rocking component 138 rotates the bioreactor 100 around central axis 142 of the bioreactor 100. Rotational rocking component 138 may be rotationally associated with bioreactor 100. In embodiments, bioreactor 100 may be rotated continuously in a single direction around central axis 142 in a clockwise or counterclockwise direction. Alternatively, bioreactor 100 may rotate in alternating fashion, first clockwise, then counterclockwise, for example, around central axis 142, according to embodiments.

The CES may also include a second rotational rocking component that rotates bioreactor 100 around rotational axis 144. Rotational axis 144 may pass through the center point of bioreactor 100 and may be normal to central axis 142. Bioreactor 100 may be rotated continuously in a single direction around rotational axis 144 in a clockwise or counterclockwise direction, in embodiments. Alternatively, bioreactor 100 may be rotated around rotational axis 144 in an alternating fashion, first clockwise, then counterclockwise, for example. In various embodiments, bioreactor 100 may also be rotated around rotational axis 144 and positioned in a horizontal or vertical orientation relative to gravity.

In embodiments, lateral rocking component 140 may be laterally associated with bioreactor 100. The plane of lateral rocking component 140 moves laterally in the −x and −y directions, in embodiments. The settling of cells in the bioreactor may be reduced by movement of cell-containing media within the hollow fibers, according to embodiments.

The rotational and/or lateral movement of a rocking device may reduce the settling of cells within the device and reduce the likelihood of cells becoming trapped within a portion of the bioreactor. The rate of cells settling in the cell growth chamber is proportional to the density difference between the cells and the suspension media, according to Stoke's Law. In some embodiments, a 180 degree rotation (fast) with a pause (having a total combined time of 30 seconds, for example) repeated as described above keeps non-adherent red blood cells suspended. A minimum rotation of about 180 degrees would be preferred in an embodiment; however, one could use rotation of up to 360 degrees or greater. Different rocking components may be used separately, or may be combined in any combination. For example, a rocking component that rotates bioreactor 100 around central axis 142 may be combined with the rocking component that rotates bioreactor 100 around axis 144. Likewise, clockwise and counterclockwise rotation around different axes may be performed independently in any combination.

Figure 2:
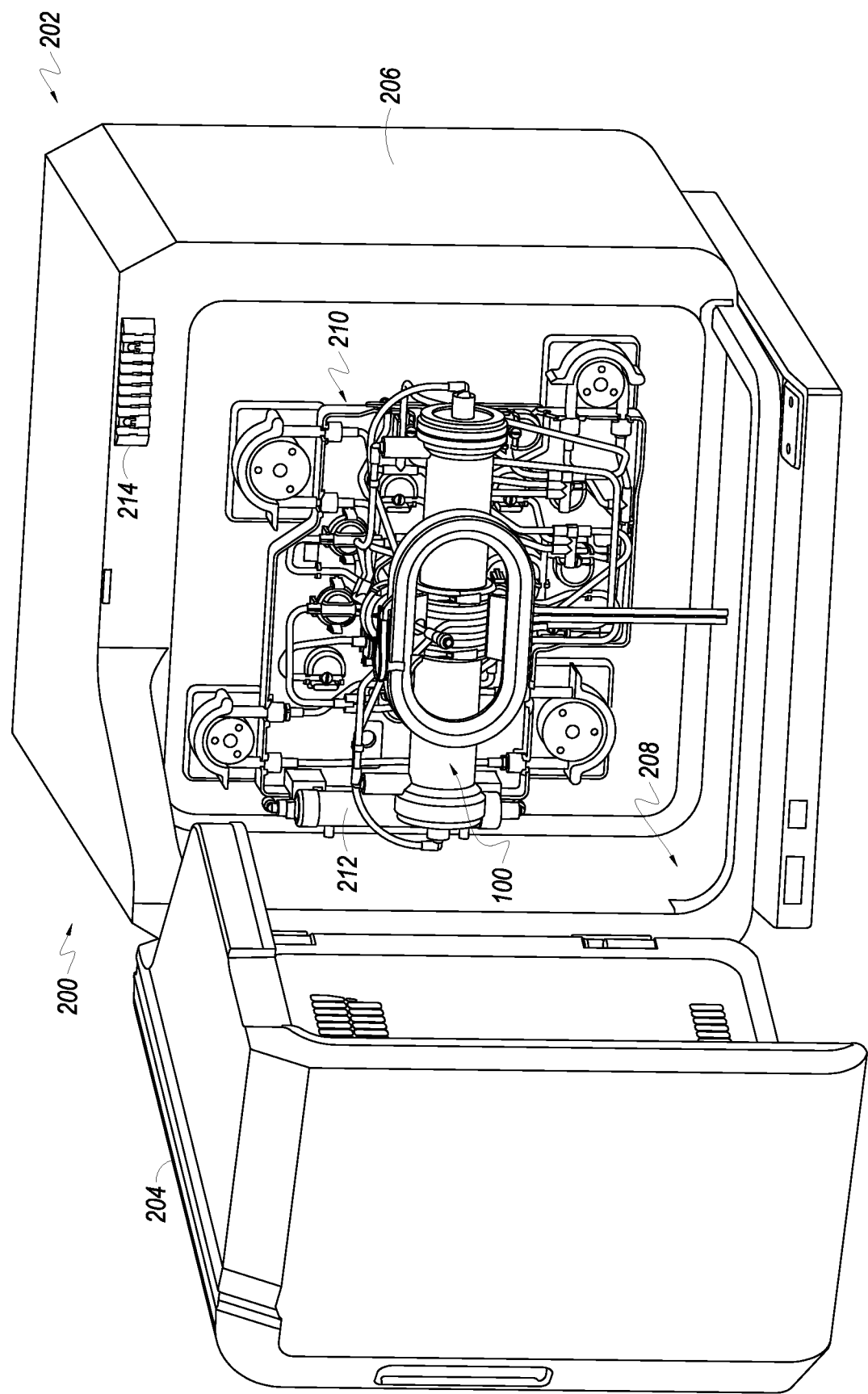
FIG. 2 illustrates a perspective view of a cell expansion system with a pre-mounted fluid conveyance device, in accordance with embodiments of the present disclosure.

Turning to FIG. 2, an embodiment of a cell expansion system 200 with a pre-mounted fluid conveyance assembly is shown in accordance with embodiments of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a pre-mounted fluid conveyance assembly 210. The pre-mounted fluid conveyance assembly 210 is detachably-attachable to the cell expansion machine 202 to facilitate relatively quick exchange of a new or unused pre-mounted fluid conveyance assembly 210 at a cell expansion machine 202 for a used pre-mounted fluid conveyance assembly 210 at the same cell expansion machine 202. A single cell expansion machine 202 may be operated to grow or expand a first set of cells using a first pre-mounted fluid conveyance assembly 210 and, thereafter, may be used to grow or expand a second set of cells using a second pre-mounted fluid conveyance assembly 210 without needing to be sanitized between interchanging the first pre-mounted fluid conveyance assembly 210 for the second pre-mounted fluid conveyance assembly 210. The pre-mounted fluid conveyance assembly 210 includes a bioreactor 100 and an oxygenator or gas transfer module 212 (also see FIG. 4). Tubing guide slots are shown as 214 for receiving various media tubing connected to pre-mounted fluid conveyance assembly 210, according to embodiments.

Figure 3:
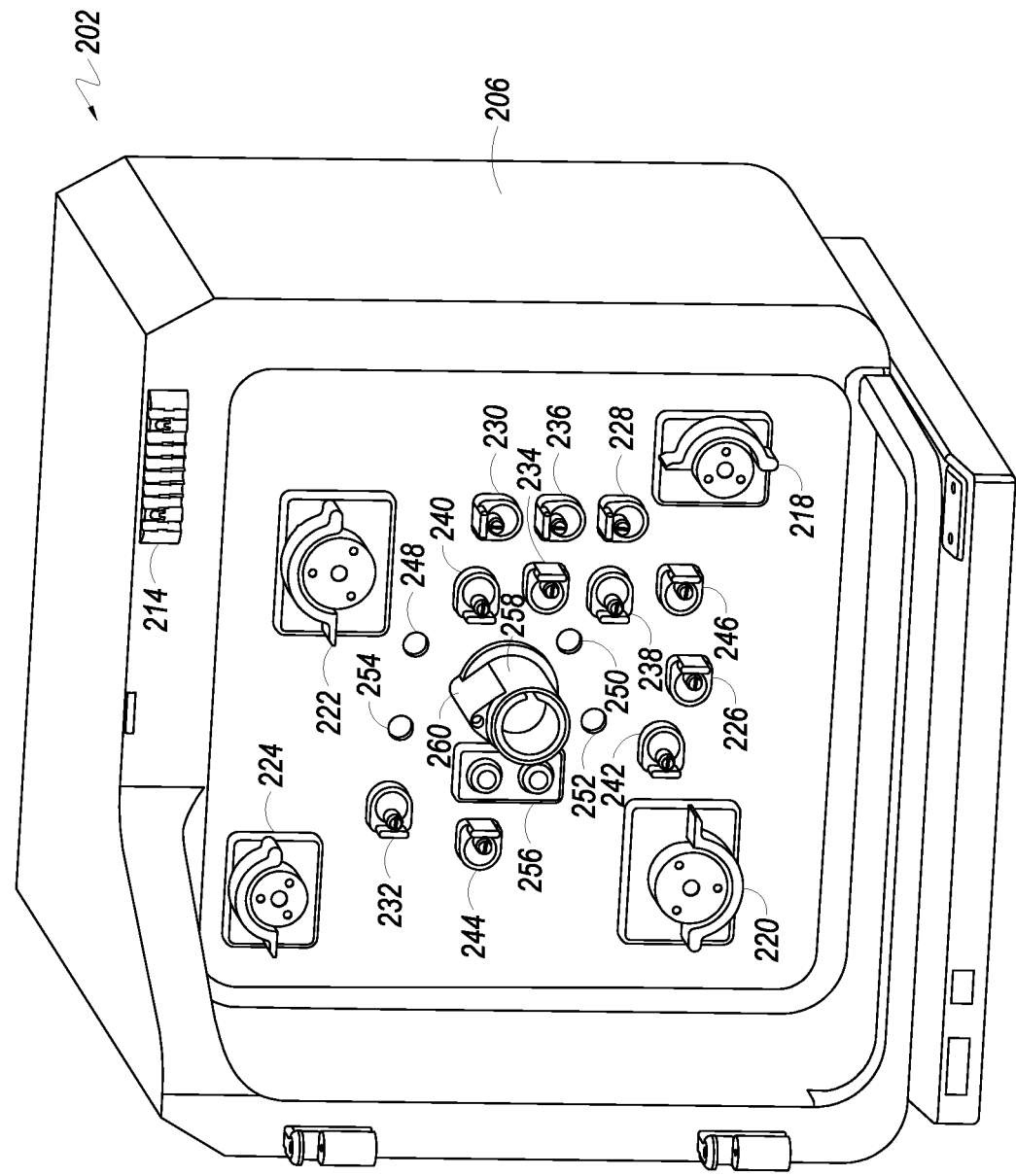
FIG. 3 depicts a perspective view of a housing of a cell expansion system, in accordance with embodiments of the present disclosure.

Next, FIG. 3 illustrates the back portion 206 of cell expansion machine 202 prior to detachably-attaching a pre-mounted fluid conveyance assembly 210 (FIG. 2), in accordance with embodiments of the present disclosure. The closable door 204 (shown in FIG. 2) is omitted from FIG. 3. The back portion 206 of the cell expansion machine 202 includes a number of different structures for working in combination with elements of a pre-mounted fluid conveyance assembly 210. More particularly, the back portion 206 of the cell expansion machine 202 includes a plurality of peristaltic pumps for cooperating with pump loops on the pre-mounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste or outlet valve 242, the EC waste or outlet valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber, according to an embodiment.

In accordance with embodiments, a shaft or rocker control 258 for rotating the bioreactor 100 is shown. Shaft fitting 260 associated with the shaft or rocker control 258 allows for proper alignment of a shaft access aperture, see e.g., 424 (FIG. 4) of a tubing-organizer, see e.g., 300 (FIG. 4) of a pre-mounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused pre-mounted fluid conveyance assembly 400 (FIG. 4) to the cell expansion machine 202, the alignment is a relatively simple matter of properly orienting the shaft access aperture 424 (FIG. 4) of the pre-mounted fluid conveyance assembly 210 or 400 with the shaft fitting 260.

Figure 4:
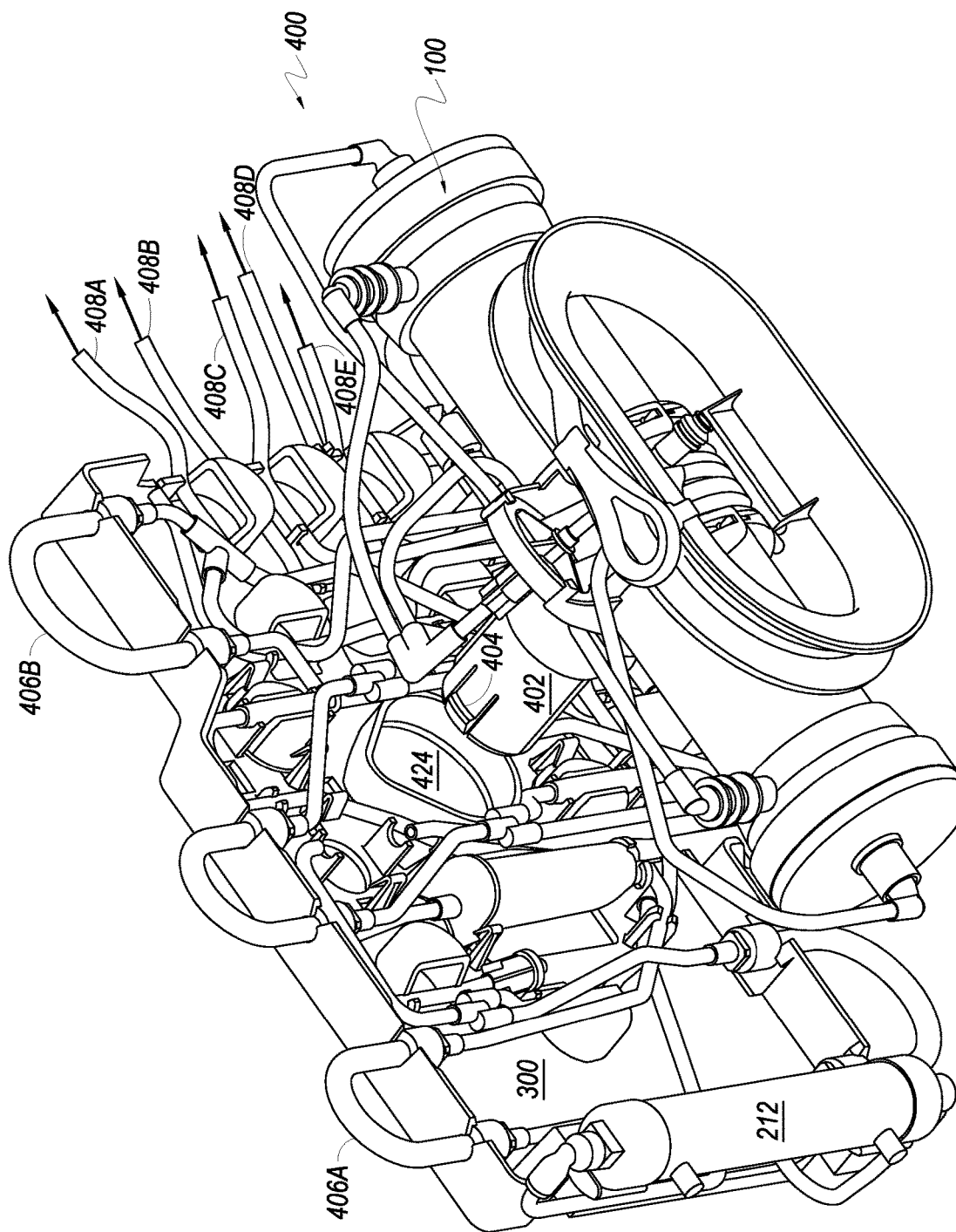
FIG. 4 illustrates a perspective view of a pre-mounted fluid conveyance device, in accordance with embodiments of the present disclosure

Turning to FIG. 4, a perspective view of a detachably-attachable pre-mounted fluid conveyance assembly 400 is shown. The pre-mounted fluid conveyance assembly 400 may be detachably-attachable to the cell expansion machine 202 (FIGS. 2 and 3) to facilitate relatively quick exchange of a new or unused pre-mounted fluid conveyance assembly 400 at a cell expansion machine 202 for a used pre-mounted fluid conveyance assembly 400 at the same cell expansion machine 202. As shown in FIG. 4, the bioreactor 100 may be attached to a bioreactor coupling that includes a shaft fitting 402. The shaft fitting 402 includes one or more shaft fastening mechanisms, such as a biased arm or spring member 404 for engaging a shaft, e.g., 258 (shown in FIG. 3), of the cell expansion machine 202.

According to embodiments, the pre-mounted fluid conveyance assembly 400 includes tubing 408A, 408B, 408C, 408D, 408E, etc., and various tubing fittings to provide the fluid paths shown in FIGS. 5 and 6, as described below. Pump loops 406A and 406B may also be provided for the pump(s). In embodiments, although the various media may be provided at the site where the cell expansion machine 202 is located, the pre-mounted fluid conveyance assembly 400 may include sufficient tubing length to extend to the exterior of the cell expansion machine 202 and to enable welded connections to tubing associated with media bag(s) or container(s), according to embodiments.

Figure 5:
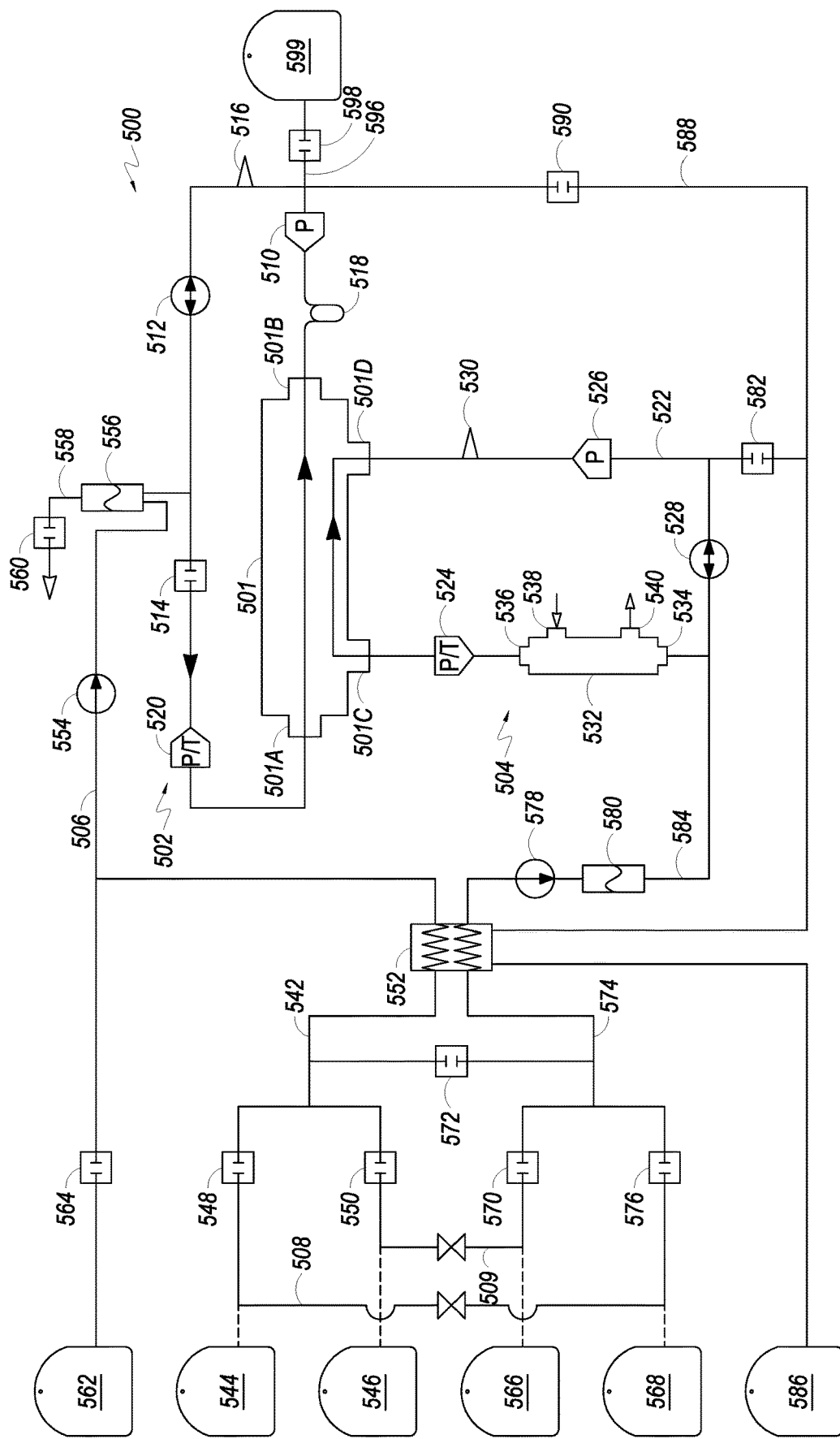
FIG. 5 depicts a schematic of a cell expansion system, in accordance with an embodiment of the present disclosure.
Figure 6:
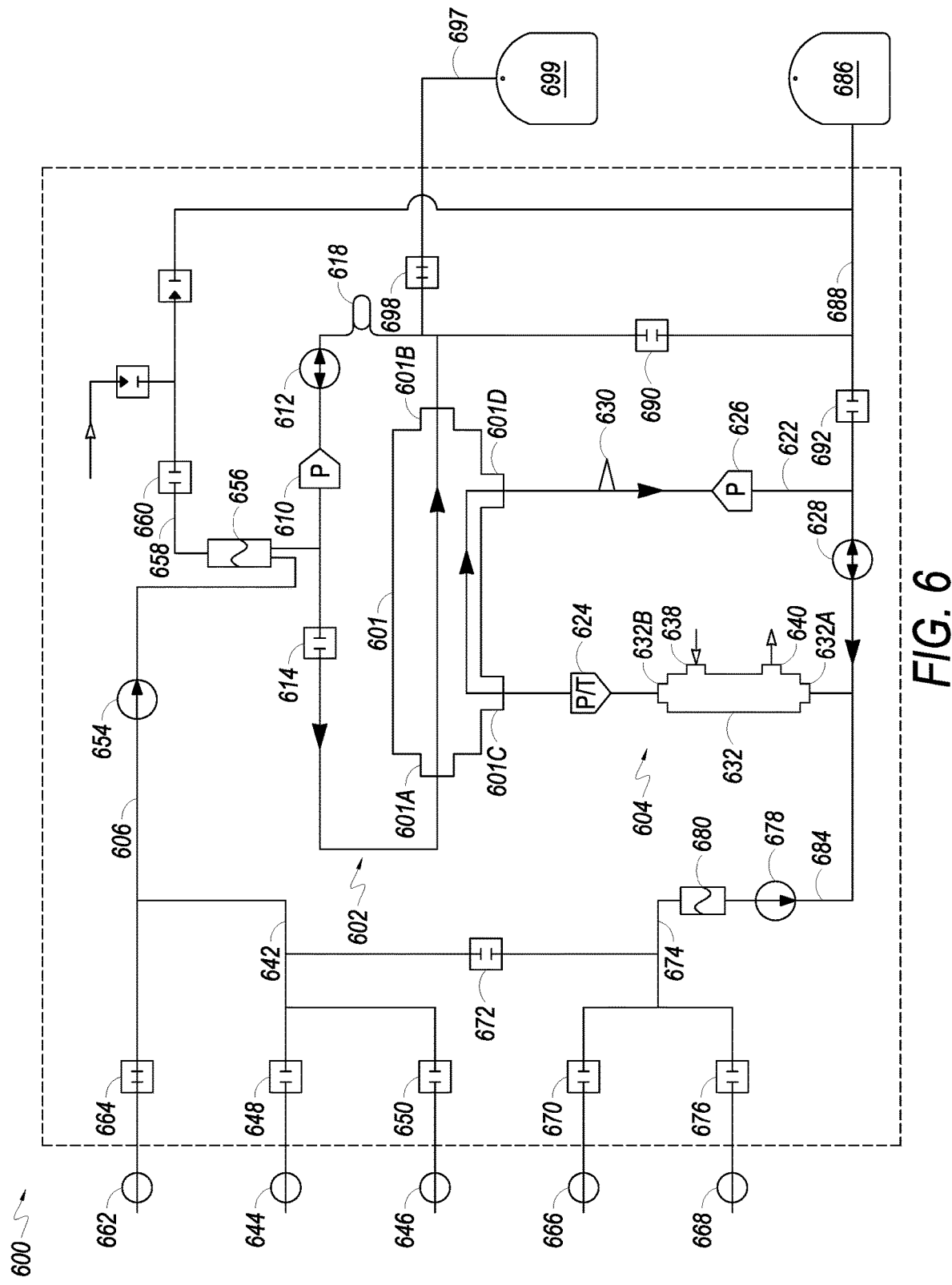
FIG. 6 illustrates a schematic of a cell expansion system, in accordance with another embodiment of the present disclosure.

Next, FIG. 5 illustrates a schematic of an embodiment of a cell expansion system 500, and FIG. 6 illustrates a schematic of another embodiment of a cell expansion system 600. In the embodiments shown in FIGS. 5 and 6, and as described below, the cells are grown in the IC space. However, the disclosure is not limited to such examples and may in other embodiments provide for cells to be grown in the EC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"), according to embodiments. First fluid flow path 506 may be fluidly associated with cell growth chamber 501 to form first fluid circulation path 502. Fluid flows into cell growth chamber 501 through IC inlet port 501A, through hollow fibers in cell growth chamber 501, and exits via IC outlet port 501B. Pressure gauge 510 measures the pressure of media leaving cell growth chamber 501. Media flows through IC circulation pump 512 which may be used to control the rate of media flow. IC circulation pump 512 may pump the fluid in a first direction or second direction opposite the first direction. Exit port 501B may be used as an inlet in the reverse direction. Media entering the IC loop may enter through valve 514. As those skilled in the art will appreciate, additional valves, pressure gauges, pressure/temperature sensors, ports, and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present embodiments.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in cell growth chamber 501 may be flushed out of cell growth chamber 501 into harvest bag 599 through valve 598 or redistributed within the hollow fibers for further growth.

Fluid in second fluid circulation path 504 enters cell growth chamber 501 via EC inlet port 501C, and leaves cell growth chamber 501 via EC outlet port 501D. Media in the EC loop 504 may be in contact with the outside of the hollow fibers in the cell growth chamber 501, thereby allowing diffusion of small molecules into and out of the hollow fibers.

Pressure/temperature gauge 524 disposed in the second fluid circulation path 504 allows the pressure and temperature of media to be measured before the media enters the EC space of the cell growth chamber 501, according to an embodiment. Pressure gauge 526 allows the pressure of media in the second fluid circulation path 504 to be measured after it leaves the cell growth chamber 501. With regard to the EC loop, samples of media may be obtained from sample port 530 or a sample coil during operation.

In embodiments, after leaving EC outlet port 501D of cell growth chamber 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator or gas transfer module 532 adds oxygen to, and removes bubbles from, media in the CES 500, for example. In various embodiments, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In the configuration depicted for CES 500, fluid media in first fluid circulation path 502 and second fluid circulation path 504 flows through cell growth chamber 501 in the same direction (a co-current configuration). The CES 500 may also be configured to flow in a counter-current conformation.

In accordance with at least one embodiment, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 570 and 576. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols may vent to the atmosphere out air valve 560 via line 558 that may be fluidly associated with air removal chamber 556.

EC media (e.g., from bag 568) or wash solution (e.g., from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing distribution valve 572.

An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste or outlet line 588. When valve 590 is opened, IC media may flow through waste line 588 and to waste or outlet bag 586. Likewise, when valve 582 is opened, EC media may flow through waste line 588 to waste or outlet bag 586.

In embodiments, cells may be harvested via cell harvest path 596. Here, cells from cell growth chamber 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media, for example, at a predetermined temperature.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with cell growth chamber 601 to form first fluid circulation path 602. Fluid flows into cell growth chamber 601 through IC inlet port 601A, through hollow fibers in cell growth chamber 601, and exits via IC outlet port 601B. Pressure sensor 610 measures the pressure of media leaving cell growth chamber 601. In addition to pressure, sensor 610 may, in embodiments, also be a temperature sensor that detects the media pressure and temperature during operation. Media flows through IC circulation pump 612 which may be used to control the rate of media flow. IC circulation pump 612 may pump the fluid in a first direction or second direction opposite the first direction. Exit port 601B may be used as an inlet in the reverse direction. Media entering the IC loop may enter through valve 614. As those skilled in the art will appreciate, additional valves, pressure gauges, pressure/temperature sensors, ports, and/or other devices may be placed at various locations to isolate and/or measure characteristics of the media along portions of the fluid paths. Accordingly, it is to be understood that the schematic shown represents one possible configuration for various elements of the CES 600, and modifications to the schematic shown are within the scope of the one or more present embodiments.

With regard to the IC loop, samples of media may be obtained from sample coil 618 during operation. Media then returns to IC inlet port 601A to complete fluid circulation path 602. Cells grown/expanded in cell growth chamber 601 may be flushed out of cell growth chamber 601 into harvest bag 699 through valve 698 and line 697. Alternatively, when valve 698 is closed, the cells may be redistributed within chamber 601 for further growth.

Fluid in second fluid circulation path 604 enters cell growth chamber 601 via EC inlet port 601C and leaves cell growth chamber 601 via EC outlet port 601D. Media in the EC loop may be in contact with the outside of the hollow fibers in the cell growth chamber 601, thereby allowing diffusion of small molecules into and out of the hollow fibers that may be within chamber 601, according to an embodiment.

Pressure/temperature sensor 624 disposed in the second fluid circulation path 604 allows the pressure and temperature of media to be measured before the media enters the EC space of the cell growth chamber 601. Sensor 626 allows the pressure and/or temperature of media in the second fluid circulation path 604 to be measured after it leaves the cell growth chamber 601. With regard to the EC loop, samples of media may be obtained from sample port 630 or a sample coil during operation.

After leaving EC outlet port 601D of cell growth chamber 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to, and removes bubbles from, media in the CES 600, for example. In various embodiments, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through cell growth chamber 601 in the same direction (a co-current configuration). The CES 600 may also be configured to flow in a counter-current conformation, according to embodiments.

In accordance with at least one embodiment, media, including cells (from a source such as a cell container, e.g., a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations.

Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668, and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing distribution valve 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one embodiment, first and second fluid circulation paths 602 and 604 are connected to waste or outlet line 688. When valve 690 is opened, IC media may flow through waste line 688 and to waste or outlet bag 686. Likewise, when valve 692 is opened, EC media may flow to waste or outlet bag 686.

After cells have been grown in cell growth chamber 601, they may be harvested via cell harvest path 697. Here, cells from cell growth chamber 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media, for example, at a predetermined temperature. It is further noted that, in embodiments, components of CES 600 and CES 500 (FIG. 5) may be combined. In other embodiments, a CES may include fewer or additional components than those shown in FIGS. 5 and 6 and still be within the scope of the present disclosure. An example of a cell expansion system that may incorporate features of the present disclosure is the Quantum® Cell Expansion System (the "Quantum® System"), manufactured by Terumo BCT, Inc. in Lakewood, Colorado.

Examples and further description of cell expansion systems are provided in U.S. patent application Ser. No. 12/042, 798 (U.S. Pat. No. 8,309,347), entitled, "Cell Expansion System and Methods of Use," issued on Nov. 13, 2012, which is hereby incorporated by reference herein in its entirety for all that it teaches and for all purposes.

Figure 7:
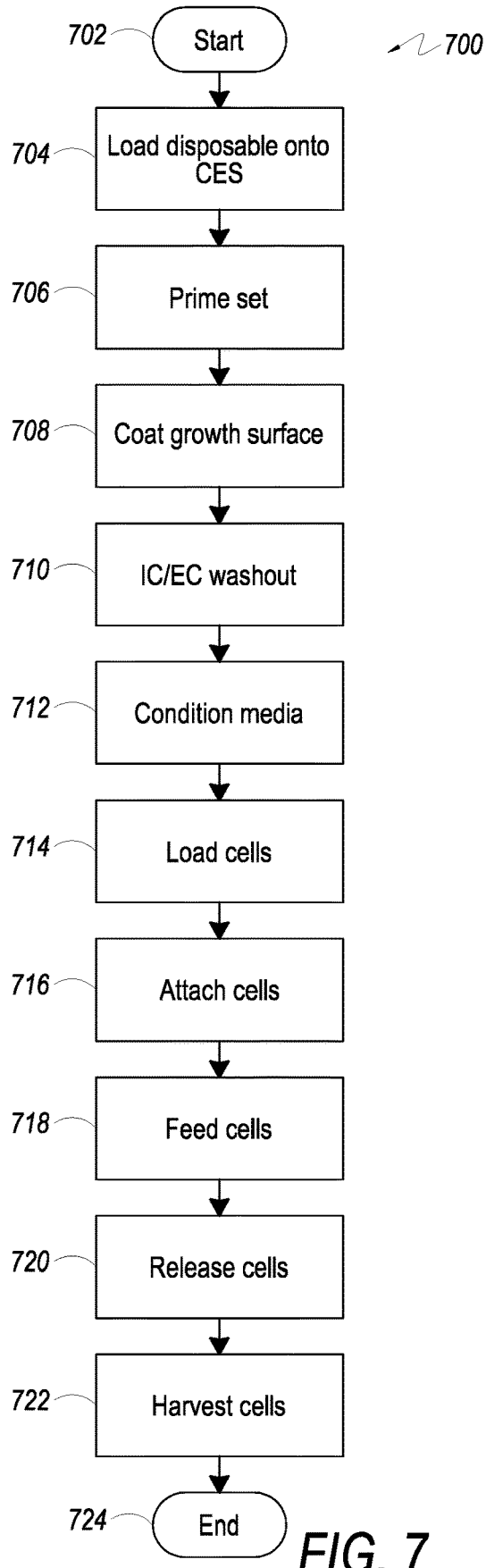
FIG. 7 depicts a flow diagram illustrating the operational characteristics of a process for applying an agent to a cell growth surface in accordance with embodiments of the present disclosure.

While various example embodiments of a cell expansion system and methods associated therewith have been described, FIG. 7 illustrates example operational steps 700 of a process for applying an agent to a cell growth surface that may be used with a cell expansion system, such as CES 500 (FIG. 5) or CES 600 (FIG. 6), in accordance with embodiments of the present disclosure. FIG. 7 will be described in conjunction with example settings and media introduction. However, the embodiments presented herein are not limited to this example; rather, the embodiments can be modified to meet other system designs or configurations. START operation is initiated 702, and process 700 proceeds to load the disposable tubing set 704 onto the cell expansion system. Next, the system may be primed 706. In an embodiment, a user or an operator, for example, may provide an instruction to the system to prime by selecting a task for priming, for example. In an embodiment, such task for priming may be a pre-programmed task. The system 500 (FIG. 5) or 600 (FIG. 6) may be primed, for example, with phosphate-buffered saline (PBS). To prime the bioreactor 501, 601, a bag (e.g., 546) may be attached (for example, to connection point 646) to the system 500, 600. When referring to numerals in the Figures, for example, such as "Numeral, Numeral" (e.g., 500, 600), such nomenclature can mean "Numeral and/or Numeral" (e.g., 500 and/or 600). Valve 550, 650 may be opened. The PBS can then be directed into the first fluid circulation path 502, 602 by the IC inlet pump 554, 654 set to pump the PBS into the first fluid circulation path 502, 602. Valve 514, 614 may be opened while the PBS enters the bioreactor 501, 601 through the inlet 501A, 601A and out the outlet 501B, 601B. Once the bioreactor 501, 601 and/or the first fluid circulation path 502, 602 have media therein with air removed by the air removal chamber 556, 656, the bioreactor 501, 601 is primed, according to an embodiment.

In an embodiment, to further prime the bioreactor 501, 601, a bag (e.g., 568) may be attached (for example, to connection point 668) to the system 500, 600. Valve 576, 676 may be opened. A media, e.g., PBS, can then be directed into the second fluid circulation path 504, 604 by the EC inlet pump 578, 678 set to pump the media into the second fluid circulation path 504, 604. Valve 582, 692 may be closed while the media enters the bioreactor 501, 601 through the inlet 501C, 601C and out the outlet 501D, 601D of the EC loop. Once the bioreactor 501, 601 and/or the second fluid circulation path 504, 604 have media therein with air removed, e.g., by an air removal chamber, the bioreactor 501, 601 is primed, according to an embodiment.

Process 700 then proceeds to coat the cell growth surface, e.g., bioreactor 501, 601, in step 708, in which the cell growth surface may be coated with a coating agent or reagent. Any coating agent(s) or reagent(s), such as fibronectin or cryoprecipitate, for example, understood by those of skill in the art may be used. In embodiments, any combination of coating agent(s) or reagent(s) may be used. In an embodiment, an outlet or waste valve 590, 690 to one of the circulation loops, e.g., IC loop 502, 602, may be closed, while the outlet or waste valve 582, 692 to the other circulation loop, e.g., EC loop 504, 604, may be opened or remains open. For example, the IC waste or outlet valve 590, 690 may be closed while the EC waste or outlet valve 582, 692 is open. In embodiments, a coating agent or reagent may be loaded into a circulation loop, e.g., IC loop 502, 602, of the cell expansion system 500, 600 until the reagent bag (e.g., 544) or container is empty. Next, the reagent may be chased from an air removal chamber 556, 656 into the circulation loop, e.g., IC loop 502, 602. The bioreactor 501, 601, e.g., cell growth surface of hollow fibers where a hollow fiber bioreactor is used, may then be coated by controlling the fluid movement in the bioreactor 501, 601. In embodiments, such control of the fluid movement uses ultrafiltration, e.g., positive ultrafiltration, to move fluid from one side (e.g., the IC side 502, 602) of the bioreactor 501, 601 to the other side (e.g., the EC side 504, 604). For example, where the IC outlet or waste valve 590, 690 may be closed, with the EC outlet or waste valve open 582, 692, a fluid in the bioreactor 501, 601 may have no pathway but through the pores of the fibers (IC outlet valve 590, 690 closed). In an embodiment, the IC inlet rate may be set to wash the IC side 502, 602 with media or a fluid, such as phosphate buffered saline (PBS), for example. Accordingly, the solution may then flow through the pores of the fibers from the IC side 502, 602 to the EC side 504, 604. The coating agent, e.g., CPPT, may be hydrostatically deposited onto the wall(s), e.g., inner wall(s), of the bioreactor fiber for a defined time period. For example, such time period may be about ten (10) minutes, according to an embodiment. Other time periods may apply according to other embodiments of the present disclosure. Such membrane ultrafiltration method allows adherence promoting proteins to be physisorbed on the bioreactor fibers as the solution flows through the pores of the fiber from the IC side 502, 602 to the EC side 504, 604.

An example of the solutions being introduced to the system 500, 600 to coat the bioreactor may be as shown below:

TABLE 1

| Bag (Connection Point) | Solution in Bag | Volume (estimation based on factory default values) |
| --- | --- | --- |
| Cell Inlet 562 (662) | None | N/A |
| Reagent 544 (644) | Reagent (e.g., CPPT or Fibronectin) | e.g., 6-25 mL CPPT in 100 mL total volume w/PBS |
| IC Media 546 (646) | None | N/A |
| Wash 566 (666) | PBS | 1 L |
| EC Media 568 (668) | None | N/A |

The coating of the bioreactor may occur in three stages. An example of the settings for the system 500, 600 for the first stage of introducing the solution(s) above may be as shown below:

TABLE 2

| Component | Setting |
| --- | --- |
| IC Inlet valve configuration | Reagent (e.g., valves 548, 648, 514, 614 open) |
| IC Inlet Rate for Pump 554, 654 | 10 mL/min |
| IC Circulation Rate for Pump 512, 612 | 100 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | Stationary (0°) |
| Stop Condition | Empty Bag for bag 544 |

An example of the settings for the system 500, 600 for the second stage of coating the bioreactor, which chases or washes reagent from the air removal chamber 556, 656, may be as shown below:

TABLE 3

| Component | Setting |
| --- | --- |
| IC Inlet valve configuration | Wash (e.g., valves 570, 670, 572, 672, 514, 614, 560, 660 open) |
| IC Inlet Rate for Pump 554, 654 | 10 mL/min |
| IC Circulation Rate for Pump 512, 612 | 100 mL/min |

TABLE 3-continued

| Component | Setting |
| --- | --- |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | Stationary (0°) |
| Stop Condition | IC Volume (e.g., 22 mL) |

An example of the settings for the system 500, 600 for the third stage of coating the bioreactor, which causes ultrafiltration from the IC side 502, 602 to the EC side 504, 604, for example, may be as shown below:

TABLE 4

| Component | Setting |
| --- | --- |
| IC Inlet valve configuration | Wash (e.g., valves 570, 670, 572, 672, 514, 614 open) |
| IC Inlet Rate for Pump 554, 654 | 50 mL/min |
| IC Circulation Rate for Pump 512, 612 | −25 mL/min |
| EC Inlet valve configuration | Wash |
| EC Inlet Rate for Pump 578, 678 | 0.1 mL/min |
| EC Circulation Rate for Pump 528, 628 | 30 mL/min |
| Outlet valve configuration | EC Outlet (e.g., valve 582, 692 open) |
| Rocker Control | Stationary (0°) |
| Stop Condition | 10 Min |

In an embodiment, such active promoting of the coating agent to a cell growth surface, as described above, may significantly decrease the amount of time to coat the cell growth surface as compared to other methods of coating a cell growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc. As described above, passive coating procedures may take about sixteen (16) hours to coat the bioreactor, for example. A significant time savings may be realized by using ultrafiltration for coating the bioreactor.

Returning to FIG. 7, once the bioreactor is coated, the IC/EC Washout task may be performed in step 710, in which fluid on the IC circulation loop 502, 602 and on the EC circulation loop 504, 604 may be replaced. The replacement volume may be determined by the number of IC Volumes and EC Volumes exchanged. An example of the solutions being introduced to the system 500, 600 during the IC/EC Washout task may be as shown below:

TABLE 5

| Bag (Connection Point) | Solution in Bag | Volume (estimation based on factory default values) |
|---|---|---|
| Cell Inlet 562 (662) | None | N/A |
| Reagent 544 (644) | None | N/A |
| IC Media 546 (646) | Media with Protein | 1.4 L |
| Wash 566 (666) | None | N/A |
| EC Media 568 (668) | None | N/A |

An example of the settings for an IC/EC Washout task of the system 500, 600 may be as shown below:

TABLE 6

| Component | Setting |
|---|---|
| IC Inlet valve configuration | IC Media (e.g., valves 550, 650, 514, 614 open) |
| IC Inlet Rate for Pump 554, 654 | 100 mL/min |
| IC Circulation Rate for Pump 512, 612 | −17 mL/min |
| EC Inlet valve configuration | IC Media (e.g., valves 550, 650, 572, 672 open) |
| EC Inlet Rate for Pump 578, 678 | 148 mL/min |
| EC Circulation Rate for Pump 528, 628 | −1.7 mL/min |
| Outlet valve configuration | IC and EC Outlet (e.g., valves 590, 690 and 582, 692 open) |
| Rocker Control | In Motion (−90°, 180°, in 1 sec intervals) |
| Stop Condition | Exchange (2.5 IC Volumes; 2.5 EC Volumes) |

Next, to maintain the proper or desired gas concentration across the fibers in the bioreactor membrane, the condition media task 712 may be executed to allow the media to reach equilibrium with the provided gas supply before cells are loaded into the bioreactor. For example, rapid contact between the media and the gas supply provided by the gas transfer module or oxygenator 532, 632 may be provided by using a high EC circulation rate. The system 500, 600 may then be maintained in a proper or desired state until a user or operator, for example, is ready to load cells into the bioreactor 501, 601. In an embodiment, the system 500, 600 may be conditioned with complete media, for example. Complete media may be any media source used for cell growth. In an embodiment, complete media may comprise alpha-MEM (α-MEM) and fetal bovine serum (FBS), for example. Any type of media known to those of skill in the art may be used.

The condition media task 712 may be a two-step process where, in the first step, the system 500, 600 provides rapid contact between the media and the gas supply by using a high EC circulation rate.

In the second step, the system 500, 600 maintains the bioreactor 501, 601 in a proper state until an operator, for example, is ready to load the cells. An example of the solutions being introduced to the system 500, 600 during the condition media task 712 may be as shown below.

While an example media is shown in Table 7, any type of media known to those of skill in the art may be used.

TABLE 7

| Bag (Connection Point) | Solution in Bag | Volume (estimation based on factory default values) |
|---|---|---|
| Cell Inlet 562 (662) | None | N/A |
| Reagent 544 (644) | None | N/A |
| IC Media 546 (646) | None | N/A |
| Wash 566 (666) | None | N/A |

TABLE 7-continued

| Bag (Connection Point) | Solution in Bag | Volume (estimation based on factory default values) |
|---|---|---|
| EC Media 568 (668) | Media with Protein (e.g., αMEM with GlutaMAX plus 10% FBS) | 0.1 L plus 6 mL/hour |

An example of the settings for a first step of the condition media task 712 may be as shown below:

TABLE 8

| Component | Setting |
|---|---|
| IC Inlet valve configuration | None |
| IC Inlet Rate for Pump 554, 654 | 0 mL/min |
| IC Circulation Rate for Pump 512, 612 | 100 mL/min |
| EC Inlet valve configuration | EC Media (and/or IC Media) (e.g., valve 576, 676 open) |
| EC Inlet Rate for Pump 578, 678 | 0.1 mL/min |
| EC Circulation Rate for Pump 528, 628 | 250 mL/min |
| Outlet valve configuration | EC Outlet (e.g., valve 582, 692 open) |
| Rocker Control | Stationary |
| Stop Condition | Time (e.g., 10 min) |

An example of the settings for a second step of the condition media task 712 may be as shown below:

TABLE 9

| Component | Setting |
|---|---|
| IC Inlet valve configuration | None |
| IC Inlet Rate for Pump 554, 654 | 0 mL/min |
| IC Circulation Rate for Pump 512, 612 | 100 mL/min |
| EC Inlet valve configuration | EC Media (and/or IC Media) (e.g., valve 576, 676 open) |
| EC Inlet Rate for Pump 578, 678 | 0.1 mL/min |
| EC Circulation Rate for Pump 528, 628 | 30 mL/min |
| Outlet valve configuration | EC Outlet (e.g., valve 582, 692 open) |
| Rocker Control | Stationary |
| Stop Condition | Manual |

Process 700 next proceeds to loading cells 714 into the bioreactor 501, 601 from a cell inlet bag 562 (at connection point 662), for example. In an embodiment, the cells are loaded with uniform suspension 714. In an embodiment, the cells may be loaded into the bioreactor 501, 601 from the cell inlet bag 562 (at connection point 662) until the bag 562 is empty. Cells may then be chased or washed from the air removal chamber 556, 656 to the bioreactor 501, 601, according to an embodiment. In embodiments that utilize larger chase volumes, cells may be spread and move toward the IC outlet port 501B, 601B. The distribution of cells may be promoted across the membrane via IC circulation, such as through an IC circulation pump 512, 612, with no IC inlet, for example. Examples and further description of loading and distributing cells are provided in U.S. patent application Ser. No. 13/971,500 (U.S. Pat. No. 9,175,259), entitled, "Method of Loading and Distributing Cells in a Bioreactor of a Cell Expansion System," issued Nov. 3, 2015, which is hereby incorporated by reference herein in its entirety for all that it teaches and for all purposes.

In another embodiment, the cells may be loaded 714 using another type of cell loading, such as a high flux cell load. In yet another embodiment, the cells may be loaded 714 using another type of loading, such as a bulls-eye cell loading technique. Examples and further description of bulls-eye cell loading procedure(s) are provided in U.S. patent application Ser. No. 14/542,276 (U.S. Pat. No. 9,617,506), entitled, "Expanding Cells in a Bioreactor," issued on Apr. 11, 2017, which is hereby incorporated by reference herein in its entirety for all that it teaches and for all purposes.

An example of the solutions being introduced to the system 500, 600 to load cells 714 may be as shown below:

TABLE 10

| Bag (Connection Point) | Solution in Bag | Volume (estimation based on factory default values) |
|---|---|---|
| Cell Inlet 562 (662) | Cells | Cells (e.g., mesenchymal stem cells (MSC)) in 100 mL complete media |
| Reagent 544 (644) | None | N/A |
| IC Media 546 (646) | Media with Protein | 0.1 L |
| Wash 566 (666) | None | N/A |
| EC Media 568 (668) | None | N/A |

The loading of cells 714 may occur in stages. An example of the settings for the system 500, 600 for an example first stage may be as shown below:

TABLE 11

| Component | Setting |
|---|---|
| IC Inlet valve configuration | Cell Inlet (e.g., valves 564, 664, 514, 614 open) |
| IC Inlet Rate for Pump 554, 654 | 50 mL/min |
| IC Circulation Rate for Pump 512, 612 | 200 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | In Motion (−90°, 180°, in 1 sec intervals) |
| Stop Condition | ARC stop |

An example of the settings for the system 500, 600 for an example second stage may be as shown below:

TABLE 12

| Component | Setting |
|---|---|
| IC Inlet valve configuration | IC Media (e.g., valves 550, 650, 514, 614 open) |
| IC Inlet Rate for Pump 554, 654 | 50 mL/min |
| IC Circulation Rate for Pump 512, 612 | 200 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | In Motion (−90°, 180°, in 1 sec intervals) |
| Stop Condition | IC Volume (e.g., 22 mL) |

An example of the settings for the system 500, 600 for an example third stage may be as shown below:

TABLE 13

| Component | Setting |
|---|---|
| IC Inlet valve configuration | None |
| IC Inlet Rate for Pump 554, 654 | 0 mL/min |
| IC Circulation Rate for Pump 512, 612 | 200 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | In Motion (−90°, 180°, in 1 sec intervals) |
| Stop Condition | Time (2.0 Min) |

Further, the cells, e.g., adherent cells, may be allowed to attach 716 to the hollow fibers. In an embodiment, in allowing the cells to attach 716, adherent cells are enabled to attach to the bioreactor membrane while allowing flow on the EC circulation loop 504, 604, with the pump (e.g., 512, 612, 554, 654) flow rate to the IC loop 502, 602 set to zero. An example of the solutions being introduced to the system 500, 600 during the process of cells attaching to the membrane 716 may be as shown below:

TABLE 14

| Bag (Connection Point) | Solution in Bag | Volume (estimation based on factory default values) |
|---|---|---|
| Cell Inlet 562 (662) | None | N/A |
| Reagent 544 (644) | None | N/A |
| IC Media 546 (646) | Media with Protein | 6 mL/hour |
| Wash 566 (666) | None | N/A |
| EC Media 568 (668) | None | N/A |

An example of the settings for attaching to the membrane 716 in the system 500, 600 may be as shown below:

TABLE 15

| Component | Setting |
|---|---|
| IC Inlet valve configuration | None |
| IC Inlet Rate for Pump 554, 654 | 0 mL/min |
| IC Circulation Rate for Pump 512, 612 | 0 mL/min |
| EC Inlet valve configuration | IC Media (e.g., valves 550, 650, 572, 672 open) |
| EC Inlet Rate for Pump 578, 678 | 0.1 mL/min |
| EC Circulation Rate for Pump 528, 628 | 30 mL/min |
| Outlet valve configuration | EC Outlet (e.g., valve 582, 692 open) |
| Rocker Control | Stationary (at 180°) |
| Stop Condition | Manual |

Next, the cells may be fed in step 718, in which a flow rate, e.g., low flow rate in an embodiment, is continuously added to the IC circulation loop 502, 602 and/or the EC circulation loop 504, 604. In an embodiment, the cells may be fed with media, such as media with protein, for example. Outlet settings allow for the removal of fluid added to the system, in accordance with embodiments. An example of the solutions being introduced to the system 500, 600 during the feed step 718 may be as shown below:

TABLE 16

| Bag (Connection Point) | Solution in Bag | Volume (estimation based on factory default values) |
|---|---|---|
| Cell Inlet 562 (662) | None | N/A |
| Reagent 544 (644) | None | N/A |
| IC Media 546 (646) | Media with Protein | 6 mL/hour |
| Wash 566 (666) | None | N/A |
| EC Media 568 (668) | None | N/A |

An example of the settings for the feed step 718 in the system 500, 600 may be as shown below:

TABLE 17

| Component | Setting |
|---|---|
| IC Inlet valve configuration | IC Media (e.g., valves 550, 650, 514, 614 open) |
| IC Inlet Rate for Pump 554, 654 | 0.1 mL/min |
| IC Circulation Rate for Pump 512, 612 | 20 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | IC Outlet (e.g., valve 590, 690 open) |
| Rocker Control | Stationary (at 0°) |
| Stop Condition | Manual |

When it is determined to harvest the expanded cells, such as after the cells have reached confluence, after a defined period of time, according to user preference, etc., process 700 proceeds to release cells 720, in which the cells may be released from the membrane of the bioreactor 501, 601 and may be suspended in the IC loop 502, 602. Following the release of any adherent cells, harvest operation 722 transfers the cells in suspension from the IC circulation loop 502, 602, including any cells remaining in the bioreactor 501, 601, to a harvest bag 599, 699 or other container. Process 700 then terminates at END operation 724.

The releasing of cells 720 and harvesting of those cells 722 may be a five-step process, according to embodiments. An example of the solutions being introduced to the system 500, 600 during the release/harvest steps 720, 722 may be as shown below:

TABLE 18

| Bag (Connection Point) | Solution in Bag | Volume (estimation based on factory default values) |
|---|---|---|
| Cell Inlet 562 (662) | None | N/A |
| Reagent 544 (644) | Trypsin | 180 mL |
| IC Media 546 (646) | Media with Protein | 0.6 L |
| Wash 566 (666) | PBS | 1.4 L |
| EC Media 568 (668) | None | N/A |

A first step in the releasing of cells 720 may perform an IC/EC Washout task in preparation for adding a reagent. For example, IC/EC media may be replaced with a phosphate buffered saline (PBS) to remove protein, calcium ($Ca^{2+}$), and magnesium ($Mg^{2+}$) in preparation for adding trypsin, or another chemical-releasing agent, to release any adherent cells. An example of the settings for an example first step of the release step 720 with the system 500, 600 may be as shown below:

TABLE 19

| Component | Setting |
|---|---|
| IC Inlet valve configuration | Wash (e.g., valves 570, 670, 572, 672, 514, 614 open) |
| IC Inlet Rate for Pump 554, 654 | 100 mL/min |
| IC Circulation Rate for Pump 512, 612 | −17 mL/min |
| EC Inlet valve configuration | Wash |
| EC Inlet Rate for Pump 578, 678 | 148 mL/min |
| EC Circulation Rate for Pump 528, 628 | −1.7 mL/min |
| Outlet valve configuration | IC Outlet (e.g., valve 590, 690 open) and EC outlet (e.g., valve 582, 692 open) |
| Rocker Control | In Motion (−90°, 180°, 1 second interval) |
| Stop Condition | Exchange (2.5 IC volumes; 2.5 EC volumes) |

A second step of the releasing cell process 720 includes loading a reagent into the system 500, 600 until the reagent bag 544 is empty. An example of the settings for an example second step of the release step 720 with the system 500, 600 may be as shown below:

TABLE 20

| Component | Setting |
|---|---|
| IC Inlet valve configuration | Reagent (e.g., valves 548, 648, 514, 614 open) |
| IC Inlet Rate for Pump 554, 654 | 50 mL/min |
| IC Circulation Rate for Pump 512, 612 | 300 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC outlet (e.g., valve 582, 692 open) |
| Rocker Control | In Motion (−90°, 180°, 1 second interval) |
| Stop Condition | Empty Bag (Reagent Bag 544 empty) |

A third step in the releasing cell process can chase the reagent into the IC loop 502, 602. An example of the settings for an example third step of the release step 720 with the system 500, 600 may be as shown below:

TABLE 21

| Component | Setting |
|---|---|
| IC Inlet valve configuration | Wash (e.g., valves 570, 670, 572, 672, 514, 614 open) |
| IC Inlet Rate for Pump 554, 654 | 50 mL/min |
| IC Circulation Rate for Pump 512, 612 | 300 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC outlet (e.g., valve 582, 692 open) |
| Rocker Control | In Motion (−90°, 180°, 1 second interval) |
| Stop Condition | IC Volume (22 mL) |

A fourth step in the releasing cell process 720 can mix the reagent within the IC loop 502, 602. An example of the settings for an example fourth step of the release step 720 with the system 500, 600 may be as shown below:

TABLE 22

| Component | Setting |
| --- | --- |
| IC Inlet valve configuration | None |
| IC Inlet Rate for Pump 554, 654 | 0 mL/min |
| IC Circulation Rate for Pump 512, 612 | 300 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC outlet (e.g., valve 582, 692 open) |
| Rocker Control | In Motion (−90°, 180°, 1 second interval) |
| Stop Condition | Time (4 Minutes) |

An example of the settings for an example fifth step, which may generally be a harvest step 722, with the system 500, 600 may be as shown below:

TABLE 23

| Component | Setting |
| --- | --- |
| IC Inlet valve configuration | IC Media (e.g., valves 550, 650, 514, 614 open) |
| IC Inlet Rate for Pump 554, 654 | 400 mL/min |
| IC Circulation Rate for Pump 512, 612 | −70 mL/min |
| EC Inlet valve configuration | IC Media (e.g., valves 550, 650, 572, 672 open) |
| EC Inlet Rate for Pump 578, 678 | 60 mL/min |
| EC Circulation Rate for Pump 528, 628 | 30 mL/min |
| Outlet valve configuration | Harvest (e.g., valve 598, 698 open) |
| Rocker Control | In Motion (−90°, 180°, 1 second interval) |
| Stop Condition | IC Volume (378 mL) |

As described above, following release step 720 and harvest step 722, process 700 terminates at END operation 724.

Figure 8A:
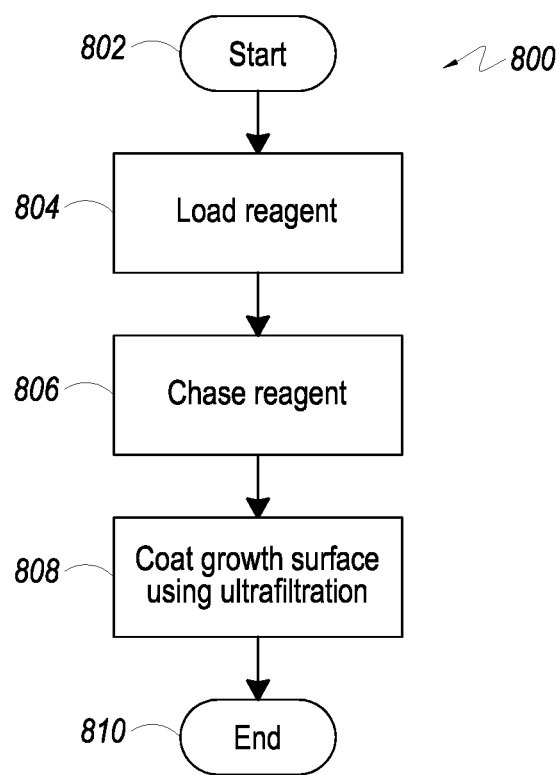
FIG. 8A illustrates a flow diagram depicting the operational characteristics of a process for applying a reagent to a cell growth surface in accordance with embodiments of the present disclosure.

Turning to FIG. 8A, example operational steps 800 of a process for applying an agent or reagent to a cell growth surface that may be used with a cell expansion system, such as CES 500 (FIG. 5) or CES 600 (FIG. 6), are provided in accordance with embodiments of the present disclosure. START operation is initiated 802, and process 800 proceeds to load a reagent, or coating agent, 804 into a circulation loop, e.g., IC loop 502, 602, of a cell expansion system 500, 600. In an embodiment, such loading proceeds until a bag (e.g., 544) or container including the reagent or coating agent is empty. In another embodiment, such loading proceeds for a defined period of time or other condition as understood by a person of skill in the art. Example parameters 822 and 828 for such loading step 804 may be found in FIG. 8C, in which Table 821 provides example parameters or settings 828 for various steps 822, 824, and 826 of applying an agent to a cell growth surface in accordance with an embodiment of the present disclosure. Such example parameters or settings 828 include an example IC inlet of about 100 mL SDE CPPT, as an example coating solution. In an embodiment, CPPT may be prepared so as to create about 25 mL "single donor equivalent (SDE)" aliquots: (1) unprocessed CPPT may be obtained from a blood center; (2) CPPT may be diluted in PBS to a final volume of about 100 mL for every donor represented by the product (e.g.: 5 donors for CPPT product=about 500 mL of total solution); (3) this stock solution may be divided into about 25 mL aliquots. In an embodiment, each aliquot may be sufficient to coat one cell expansion system, e.g., Quantum System®, bioreactor, for example. Other volumes and/or proportions may be used in accordance with embodiments of the present disclosure.

In an embodiment, prior to loading such reagent or coating agent, an outlet or waste valve 590, 690 to one of the circulation loops, e.g., IC loop 502, 602, may be closed, while the outlet or waste valve 582, 692 to the other circulation loop, e.g., EC loop 504, 604, remains open. For example, the IC waste or outlet valve 590, 690 may be closed while the EC waste or outlet valve 582, 692 may be open, according to an embodiment. In another embodiment, such closing of an outlet or waste valve, e.g., IC waste or outlet valve 590, 690, while keeping another outlet or waste valve, e.g., EC waste or outlet valve 582, 692, open may occur after loading the reagent into the circulation loop 502, 602. In other embodiments, other types of fluid flow control device(s) to control fluid movement may be used as understood by a person of skill in the art.

Next, the reagent may be chased or washed 806 from an air removal chamber 556, 656 into the circulation loop, e.g., IC loop 502, 602. Example parameters 824 and 828 for such chase step 806 may be found in FIG. 8C.

The cell growth surface of the bioreactor 501, 601, e.g., cell growth surface of hollow fibers where a hollow fiber bioreactor is used, may then be coated 808 by controlling the fluid movement, e.g., ultrafiltration, in the bioreactor 501, 601. Example parameters 826 and 828 for such coating step 808 may be found in FIG. 8C. As shown in FIG. 8C, coating step 808 and example parameters 826, 828 may include a stop condition of about ten (10) minutes, according to an embodiment. Steps 822, 824, and 826 for applying an agent to a growth surface may be followed by an IC/EC Washout step, for example, and/or other steps, where it is desired to continue with a process for expanding cells in a cell expansion system 500, 600, according to an embodiment.

As described above, control of the fluid movement may use ultrafiltration, such as positive ultrafiltration, to move fluid from one side (the IC side 502, 602) of the bioreactor 501, 601 to the other side (the EC side 504, 604), according to embodiments. For example, where the IC outlet or waste valve 590, 690 may be closed, with the EC outlet or waste valve 582, 692 open, a fluid in the bioreactor 501, 601 may have no pathway but through the pores of the fibers (IC outlet valve 590, 690 closed). In an embodiment, the IC inlet rate may be set to wash the IC side 502, 602 with media or a fluid, such as phosphate buffered saline (PBS), for example. Accordingly, the solution may flow through the pores of the fibers from the IC side 502, 602 to the EC side 504, 604. Such coating agent, e.g., CPPT, may be hydrostatically deposited onto the inner wall(s) of the bioreactor fiber for a defined time period. For example, such time period may be about ten (10) minutes, according to an embodiment. Such membrane ultrafiltration method allows adherence promoting proteins to be physisorbed on the bioreactor fibers as the coating solution flows through the pores of the fiber from the IC side to the EC side, for example.

As described above, the active promoting of the coating agent to a cell growth surface may significantly decrease the amount of time it may take to coat the growth surface as compared to other methods of coating a growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc.

Following the application of the reagent or coating agent to the cell growth surface, process 800 then terminates at END operation 810.

Figure 8B:
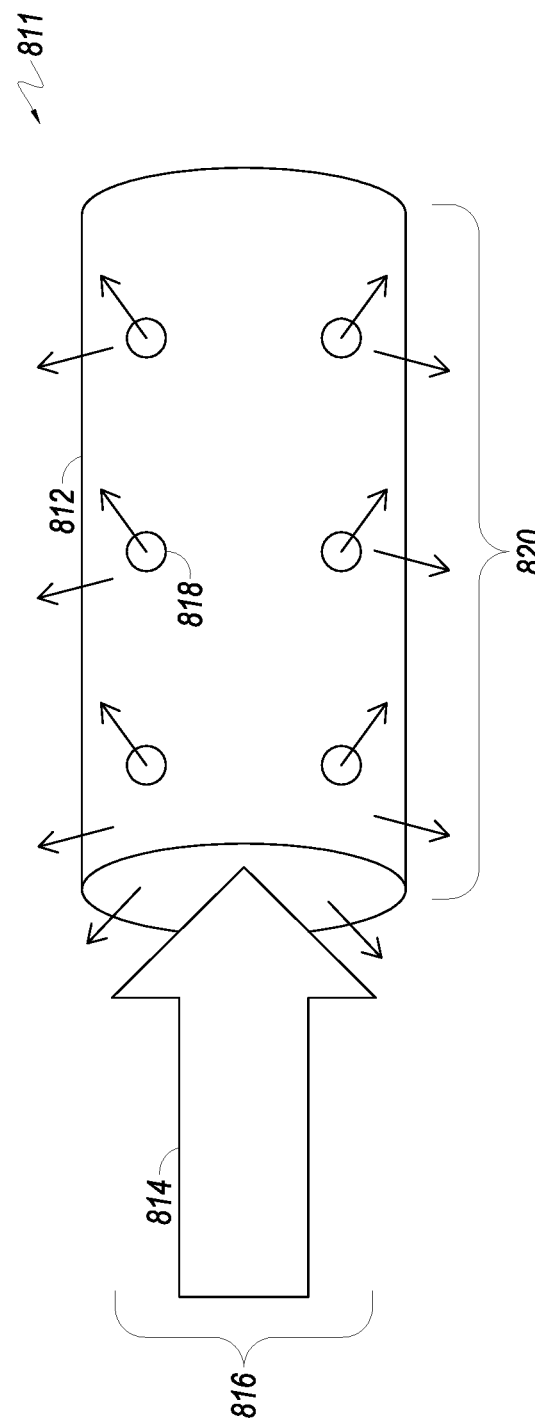
FIG. 8B depicts a schematic of applying an agent to a cell growth surface of a hollow fiber in accordance with embodiments of the present disclosure.

While FIG. 8A illustrates a method for applying a coating agent or reagent to a cell growth surface, FIG. 8B depicts a schematic of applying an agent to a growth surface of a hollow fiber, in accordance with embodiments of the present disclosure. In embodiments, schematic 811 depicts the flow of a coating agent or reagent solution, such as cryoprecipitate solution 814, through a single fiber 812, e.g., hollow fiber, of a bioreactor during an active coating procedure. In schematic 811, a coating agent and/or coating solution, e.g., a cryoprecipitate solution, may be introduced to the fibers of a bioreactor, e.g., a hollow fiber bioreactor 501, 601, on the intracapillary (IC) side 816, for example. In such embodiment, an IC waste valve or IC outlet valve 590, 690 may be closed, while an EC waste valve or EC outlet valve 582, 692 may be open. In embodiments, the IC inlet rate for a chase step, e.g., step 824 (FIG. 8C), may be set. The IC inlet rate may then be set for a Wash step, e.g., step 826 (FIG. 8C), according to an embodiment. For example, the IC inlet rate may be set to about 50 mL/minute for a wash task with media or a fluid, such as phosphate buffered saline (PBS). In embodiments, the IC inlet rate may be set to any rate in a range including a value greater than or equal to about 5 mL/minute to less than or equal to about 100 mL/minute. For example, the IC inlet rate may be set to a value greater than or equal to about 40 mL/minute to less than or equal to about 60 mL/minute.

Returning to FIG. 8B, the coating agent in the coating solution, e.g., cryoprecipitate solution 814, may be hydrostatically deposited onto the inner wall of bioreactor fiber 812 for a specified time period, e.g., about ten (10) minutes. Various time periods may be used based on the CES 500, 600 configurations, for example. Such membrane ultrafiltration process allows adherence promoting protein(s) to be physisorbed on the bioreactor fibers as the reagent solution or coating solution flows through the pores 818 of the fiber 812 from the IC side of the fiber 816 to the EC side of the fiber 820.

Figure 9A:
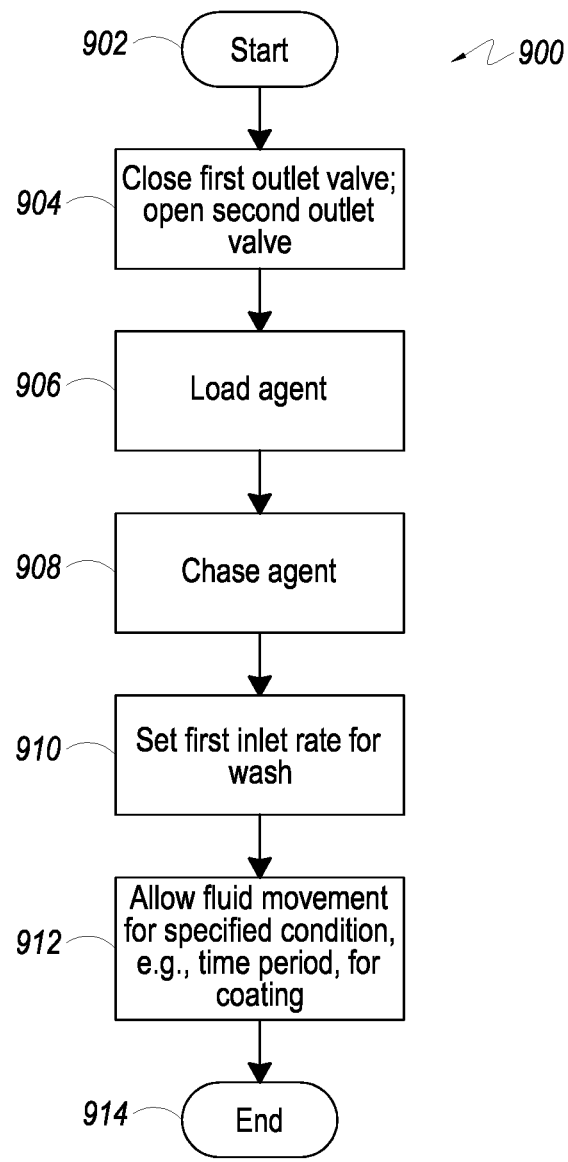
FIG. 9A depicts a flow diagram illustrating the operational characteristics of a process for applying an agent to a cell growth surface in accordance with embodiments of the present disclosure.

Turning to FIG. 9A, example operational steps 900 of a process for applying an agent or reagent to a cell growth surface that may be used with a cell expansion system, such as CES 500 (FIG. 5) or CES 600 (FIG. 6), are provided in accordance with embodiments of the present disclosure. In embodiments, such CES is automated, and various steps and/or parameters may be pre-programmed, set, and/or created to execute one or more tasks to expand cells. START operation is initiated 902, and process 900 proceeds to close 904 a first outlet or waste valve 590, 690, and open (or leave/remain open) a second outlet or waste valve 582, 692, where the first 590, 690 and second 582, 682 outlet valves are different. In an embodiment, such as where cells may be grown on the IC side, for example, an IC outlet valve or IC waste valve 590, 690 may be closed, while an EC outlet valve or EC waste valve 582, 692 may be open or remain open. In another embodiment, such as where cells may be grown on the EC side, for example, an EC outlet valve or EC waste valve 582, 692 may be closed, while an IC outlet valve or IC waste valve 590, 690 may be open or remain opened. In an embodiment, step 904 occurs before loading a coating agent or reagent into the cell expansion system 500, 600. In another embodiment, step 904 occurs after the loading of a coating agent. In an embodiment, step 904 may occur at any time during process 900. Process 900 is offered for illustrative purposes and may be rearranged, combined into other steps, etc. Further, additional or fewer steps may be used in other embodiments.

Returning to FIG. 9, process 900 proceeds to load an agent 906 or agent solution, e.g., coating agent or coating solution, into a cell expansion system, such as cell expansion system 500, 600, for example. In an embodiment, a coating agent or coating agent solution is loaded into a circulation loop, e.g., IC loop 502, 602, of a cell expansion system 500, 600. In an embodiment, such loading proceeds until a bag (e.g., 544) or container including the reagent or coating agent is empty. In another embodiment, such loading proceeds for a defined period of time or other condition as understood by a person of skill in the art.

Next, the agent or reagent may be chased or washed 908 from an air removal chamber 556, 656 into the circulation loop, e.g., IC loop 502, 602. Process 900 next proceeds to set a first inlet rate 910, e.g., IC inlet rate, to wash a first side, e.g., IC side 816 (FIG. 8B), with media or a fluid, such as phosphate buffered saline (PBS), for example. For example, the IC inlet rate may be set to about 50 mL/minute for a wash task with media or a fluid, such as phosphate buffered saline (PBS). In embodiments, the IC inlet rate may be set to any rate in a range including a value greater than or equal to about 5 mL/minute to less than or equal to about 100 mL/minute. For example, the IC inlet rate may be set to a value greater than or equal to about 40 mL/minute to less than or equal to about 60 mL/minute. In embodiments, the IC inlet rate may be set to about 51 mL/minute; about 52 mL/minute; about 53 mL/minute; about 54 mL/minute; about 55 mL/minute; about 56 mL/minute; about 57 mL/minute; about 58 mL/minute; about 59 mL/minute; about 60 mL/minute; about 49 mL/minute; about 48 mL/minute; about 47 mL/minute; about 46 mL/minute; about 45 mL/minute; about 44 mL/minute; about 43 mL/minute; about 42 mL/minute; about 41 mL/minute; about 40 mL/minute; etc.

Such washing, or increased inlet rate, promotes the movement of fluid 912 from a first side 816 (FIG. 8B) of a hollow fiber 812 to a second side 820 of the hollow fiber 812, e.g., from the IC side 816 to the EC side 820, in which ultrafiltration allows proteins or molecules that are too large to pass through the pores 818 of a hollow fiber 812 to adhere to the bioreactor fiber 812 and thus coat the walls while the fluid in which the coating agent is suspended flows through the pores 818. Where the fluid flows through the pores 818 of the fiber 812 from the IC 816 to the EC side 820, positive ultrafiltration may result in the deposit of the coating agent or reagent on the inner walls, or IC side 816, of the fiber(s). On the other hand, in an embodiment where cells are grown on an EC side 820 and where the solution flows through the pores 818 of the fiber 812 from the EC side 820 to the IC side 816, negative ultrafiltration may result in the deposit of the coating agent or reagent on the outer walls, or EC side 820, of the fiber(s) 812. In an embodiment, such fluid movement may occur for a specified time period, e.g., about ten (10) minutes, to allow for such coating. In an embodiment, such active promoting of the coating agent to a cell growth surface may significantly decrease the amount of time it may take to coat the cell growth surface as compared to other methods of coating a cell growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc. In other embodiments, other conditions may be used to determine when to stop or decrease the active promotion of the fluid. For example, such active promotion may be stopped or decreased when a media bag (e.g., 566) containing a wash solution is empty. Other conditions may be used according to embodiments. Process 900 then terminates at END operation 914.

Figure 9B:
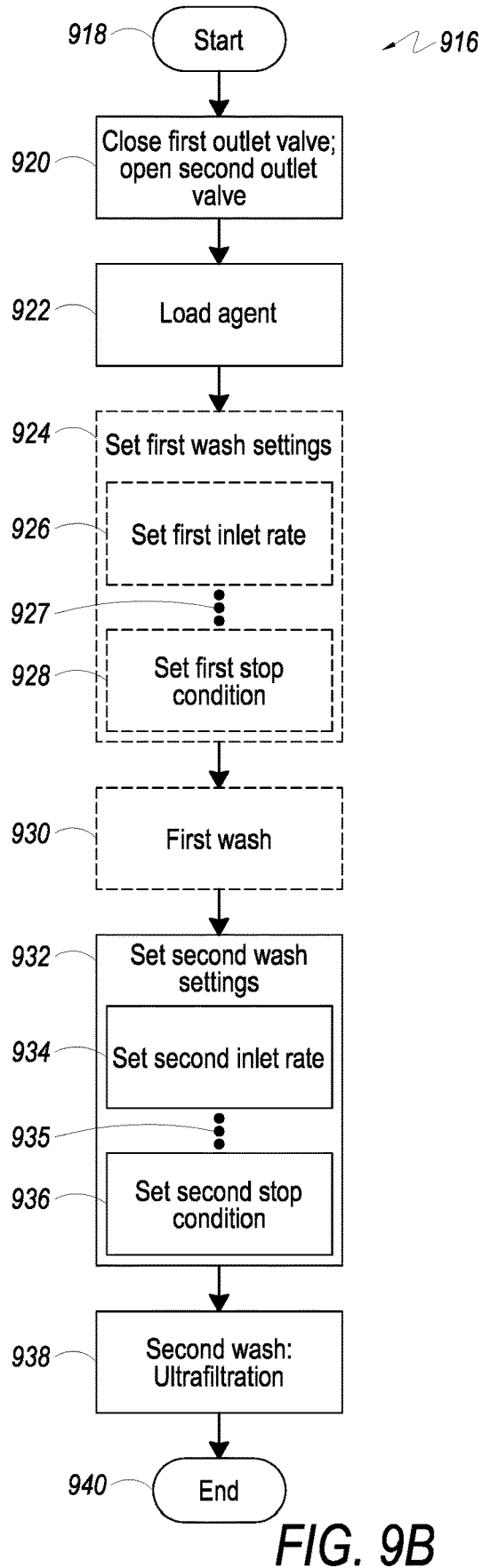
FIG. 9B depicts a flow diagram illustrating the operational characteristics of a process for applying an agent to a cell growth surface in accordance with embodiments of the present disclosure.

Turning to FIG. 9B, example operational steps 916 of a process for applying an agent to a cell growth surface that may be used with a cell expansion system, such as CES 500 (FIG. 5) or CES 600 (FIG. 6), are provided in accordance with embodiments of the present disclosure. In embodiments, such CES is automated, and various steps and/or parameters may be pre-programmed, set, and/or created as custom or user-defined tasks to expand cells. START operation is initiated 918, and process 916 proceeds to close 920 a first outlet or waste valve 590, 690, and open (or leave/remain open) a second outlet or waste valve 582, 692, where the first 590, 690 and second 582, 692 outlet valves are different. In an embodiment, such as where cells may be grown on the IC side, for example, an IC outlet valve or IC waste valve 590, 690 may be closed, while an EC outlet valve or EC waste valve 582, 692 may be open or remain open. In another embodiment, such as where cells may be grown on the EC side, for example, an EC outlet valve or EC waste valve 582, 692 may be closed, while an IC outlet valve or IC waste valve 590, 690 may be open or remain opened. In an embodiment, step 920 occurs before loading a coating agent or reagent into the cell expansion system 500, 600. In another embodiment, step 920 occurs after the loading of a coating agent. In an embodiment, step 920 may occur at any time during process 916. Process 916 is offered for illustrative purposes and may be rearranged, combined into other steps, etc. Further, additional or fewer steps may be used in other embodiments.

Returning to FIG. 9B, process 916 proceeds to load an agent 922 or agent solution, e.g., coating agent or coating solution, into a cell expansion system, such as cell expansion system 500, 600, for example. In an embodiment, a coating agent or coating agent solution is loaded into a circulation loop, e.g., IC loop 502, 602, of a cell expansion system 500, 600. In an embodiment, such loading proceeds until a bag (e.g., 544) or container including the reagent or coating agent is empty. In another embodiment, such loading proceeds for a defined period of time or other condition as understood by a person of skill in the art.

Next, process 916 proceeds to optional step 924, in which the settings for a first wash may be set. During such first wash, the agent may be chased or washed from an air removal chamber 556, 656 into the circulation loop, e.g., IC loop 502, 602. The settings may include, for example, optionally setting a first inlet rate 926 and/or optionally setting a first stop condition 928. An example of a first stop condition may include a particular volume, e.g., an IC volume. Optional settings 926 and 928 are offered merely for illustrative purposes. Other settings and/or subsets of settings to control a first wash may be included. There may be fewer or more settings as represented by ellipsis 927. When settings for a first wash are set, process 916 next proceeds to optional first wash 930.

Following optional first wash 930 (or where no first wash is desired, following load agent 922), process 916 proceeds to set second wash settings 932. For example, a second inlet rate, e.g., IC inlet rate, may be set 934 to wash a first side, e.g., IC side 816 (FIG. 8B), with media or a fluid, such as phosphate buffered saline (PBS), for example. For example, the IC inlet rate may be set to about 50 mL/minute for a wash task with media or a fluid, such as phosphate buffered saline (PBS). In embodiments, the IC inlet rate may be set to any rate in a range including a value greater than or equal to about 5 mL/minute to less than or equal to about 100 mL/minute. For example, the IC inlet rate may be set to a value greater than or equal to about 40 mL/minute to less than or equal to about 60 mL/minute.

Additional or other settings may also be set to control such second wash. For example, a second stop condition may be set 936. Such stop condition may include a time period, or time interval, in which the second wash may be stopped when such stop condition is reached. As an example, a ten (10) minute time period may be set as a second stop condition for a second wash. Any time period may be used in accordance with embodiments of the present disclosure. Settings 934 and 936 are offered merely for illustrative purposes. Other settings and/or subsets of settings to control a second wash may be included. There may be fewer or more settings as represented by ellipsis 935.

Following the entering of the second wash settings at step 932, process 916 next proceeds to conducting a second wash 938. Such washing, or increased inlet rate, promotes the movement of fluid from a first side 816 (FIG. 8B) of a hollow fiber 812 to a second side 820 of the hollow fiber 812, e.g., from the IC side 816 to the EC side 820, in which ultrafiltration allows proteins or molecules that are too large to pass through the pores 818 of a hollow fiber 812 to adhere to the bioreactor fiber 812 and thus coat the walls while the solution flows through the pores 818. Where the solution flows through the pores 818 of the fiber 812 from the IC 816 to the EC side 820, positive ultrafiltration may result in the deposit of the coating agent or reagent on the inner walls, or IC side 816, of the fiber(s). On the other hand, in an embodiment where cells are grown on an EC side 820 and where the solution flows through the pores 818 of the fiber 812 from the EC side 820 to the IC side 816, negative ultrafiltration may result in the deposit of the coating agent or reagent on the outer walls, or EC side 820, of the fiber(s) 812.

Active promoting of the coating agent to a cell growth surface may significantly decrease the amount of time it may take to coat the growth surface as compared to other methods of coating a growth surface. In embodiments, such coating procedure using ultrafiltration may be referred to as an expedited coating procedure. For example, such expedited coating procedure may take less than or equal to about four (4) hours. In an embodiment, such fluid movement may occur for a specified time period, e.g., about ten (10) minutes, to allow for such coating. For example, such coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc. Any time period may be used in accordance with embodiments of the present disclosure. In an embodiment, such time period may be based on a stop condition, such as a second stop condition set in step 936. For example, a stop condition may be set where an automated CES is used to expand cells. In other embodiments, other conditions may be used to determine when to stop or decrease the active promotion of the fluid. For example, such active promotion may be stopped or decreased when a media bag (e.g., 566) containing the wash solution is empty. Other conditions may be used according to embodiments. Process 916 then terminates at END operation 940.

With respect to the processes illustrated in FIGS. 7-9, the operational steps depicted are offered for purposes of illustration and may be rearranged, combined into other steps, used in parallel with other steps, etc., according to embodiments of the present disclosure. Fewer or additional steps may be used in embodiments without departing from the spirit and scope of the present disclosure. Also, steps (and any sub-steps), such as priming, coating a bioreactor, loading cells, for example, may be performed automatically in some embodiments, such as by a processor executing custom and/or pre-programmed tasks stored in memory.

Examples and further description of tasks and protocols, including custom tasks and pre-programmed tasks, for use with a cell expansion system are provided in U.S. patent application Ser. No. 13/269,323 ("Configurable Methods and Systems of Growing and Harvesting Cells in a Hollow Fiber Bioreactor System," filed Oct. 7, 2011) and U.S. patent application Ser. No. 13/269,351 ("Customizable Methods and Systems of Growing and Harvesting Cells in a Hollow Fiber Bioreactor System," filed Oct. 7, 2011), which applications are hereby incorporated by reference herein in their entireties for all that they teach and for all purposes.

Figure 10:
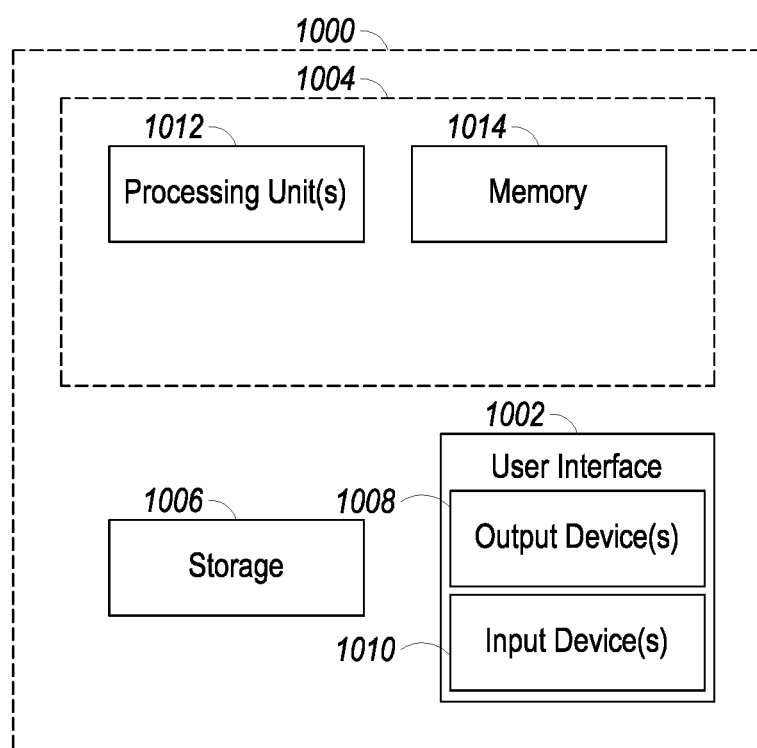
FIG. 10 illustrates an example processing system of a cell expansion system upon which embodiments of the present disclosure may be implemented.

Next, FIG. 10 illustrates example components of a computing system 1000 upon which embodiments of the present disclosure may be implemented. Computing system 1000 may be used in embodiments, for example, where a cell expansion system uses a processor to execute tasks, such as custom tasks or pre-programmed tasks performed as part of a process, such as process 700, 800, 900, and/or 916 described above. In embodiments, pre-programmed tasks may include, "IC/EC Washout" task and/or "Feed Cells" task, for example.

The computing system 1000 may include a user interface 1002, a processing system 1004, and/or storage 1006. The user interface 1002 may include output device(s) 1008, and/or input device(s) 1010 as understood by a person of skill in the art. Output device(s) 1008 may include one or more touch screens, in which the touch screen may comprise a display area for providing one or more application windows. The touch screen may also be an input device 1010 that may receive and/or capture physical touch events from a user or operator, for example. The touch screen may comprise a liquid crystal display (LCD) having a capacitance structure that allows the processing system 1004 to deduce the location(s) of touch event(s), as understood by those of skill in the art. The processing system 1004 may then map the location of touch events to UI elements rendered in predetermined locations of an application window. The touch screen may also receive touch events through one or more other electronic structures, according to embodiments. Other output devices 1008 may include a printer, speaker, etc. Other input devices 1010 may include a keyboard, other touch input devices, mouse, voice input device, etc., as understood by a person of skill in the art.

Processing system 1004 may include a processing unit 1012 and/or a memory 1014, according to embodiments of the present disclosure. The processing unit 1012 may be a general purpose processor operable to execute instructions stored in memory 1014. Processing unit 1012 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 1014 may include any short-term or long-term storage for data and/or processor executable instructions, according to embodiments. The memory 1014 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 1006 may be any long-term data storage device or component. Storage 1006 may include one or more of the systems described in conjunction with the memory 1014, according to embodiments. The storage 1006 may be permanent or removable. In embodiments, storage 1006 stores data generated or provided by the processing system 1004.

EXAMPLES

Results for some examples of protocols/methods/processes that may be used with a cell expansion system, such as CES 500 (FIG. 5) and/or CES 600 (FIG. 6), for example, that implement aspects of the embodiments may be as shown in FIGS. 11, 12A, 12B, 13A, and 13B. Although specific features may be described in the examples, such examples are provided merely for illustrative and descriptive purposes. For example, while examples may provide for the expansion of MSCs, other cell types may be used in other embodiments. The present embodiments are not limited to the examples provided herein.

It is noted that the example protocols/methods/processes are provided for illustrative purposes and are not intended to limit other embodiments, which may include different or additional steps, parameters, or other features. The example protocols/methods/processes, including the steps (and any sub-steps), may be performed automatically in some embodiments, such as by a processor executing custom tasks or pre-programmed tasks stored in memory. In other embodiments, the steps (and any sub-steps) may be performed through the combination of automated and manual execution of operations. In further embodiments, the steps (and any sub-steps) may be performed by an operator(s) or user(s) or through other manual means.

Some examples provide example data from embodiments providing for the expansion of cells using various coating procedures, various cell loading procedures, various coating materials (e.g., cryoprecipitate (CPPT), fibronectin (FN)), and/or combination(s) of such procedures and/or materials. Such procedures include, for example: positive ultrafiltration coating procedure; positive ultrafiltration coating procedure with a bulls-eye (BE) cell load procedure; positive ultrafiltration coating procedure with a load cells with uniform suspension (LWUS) cell loading procedure; overnight coating with cryoprecipitate; overnight coating with fibronectin; bulls-eye coating procedure; 28-minute bulls-eye coating procedure; etc. Examples and further description of a bulls-eye coating procedure(s) are provided in U.S. patent application Ser. No. 15/616,745, entitled, "Coating a Bioreactor," filed on Jun. 7, 2017, which claims priority to U.S. Provisional Application Ser. No. 62/347,012, entitled "Coating a Bioreactor," and filed on Jun. 7, 2016. These applications are hereby incorporated by reference herein in their entireties for all that they teach and for all purposes. As described above, examples and further description of a bulls-eye cell loading procedure(s) are provided in U.S. patent application Ser. No. 14/542,276 (U.S. Pat. No. 9,617,506), entitled, "Expanding Cells in a Bioreactor," issued on Apr. 11, 2017, which is hereby incorporated by reference herein in its entirety for all that it teaches and for all purposes.

Example 1

Figure 11:
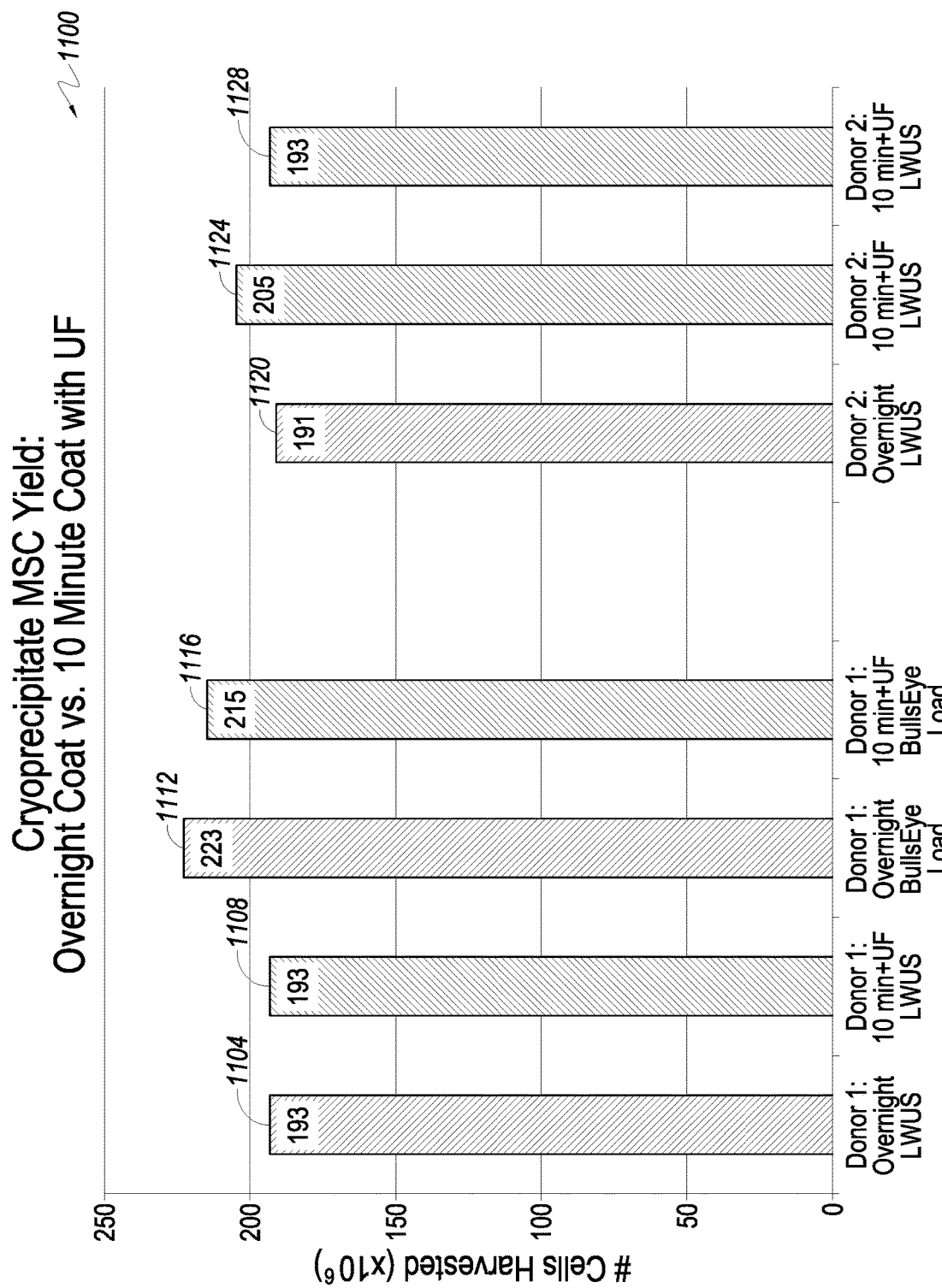
FIG. 11 depicts example cell yields using a coating application(s) in accordance with embodiments of the present disclosure.

Example results of expanding cells using a coating procedure(s) with, for example, the above methods 700, 800, 900, and/or 916 and/or with systems 500 (FIG. 5), 600 (FIG. 6), are shown in graph 1100 of FIG. 11, in accordance with embodiments of the present disclosure. For example, such cell growth surface coating and resulting cell expansion may use the Quantum® Cell Expansion System (the "Quantum® System"), manufactured by Terumo BCT, Inc. in Lakewood, Colorado. FIG. 11 illustrates example results for coating a cell growth surface through a coating procedure with ultrafiltration, e.g., about 10-minute positive ultrafiltration coating procedure (10 min+UF), versus an overnight circulating coating procedure. As shown in graph 1100 of FIG. 11, example results may be provided for using cryoprecipate (CPPT) as a coating agent. In this example, two donors, e.g., Donor 1 and Donor 2, may be used to determine a cell harvest yield, e.g., MSC harvest yield, from the expansion of mesenchymal stem cells (MSCs) in a CES, e.g., Quantum® System. Donor 1 data includes both a Load Cells with Uniform Suspension cell loading procedure (LWUS) 1104, 1108 and a bulls-eye cell loading procedure (BullsEye Load) 1112, 1116. Donor 2 data includes results for using a load with uniform suspension cell loading procedure (LWUS) 1120, 1124, and 1128.

For Donor 1 and Donor 2, 5E+6 MSC may be loaded into a bioreactor, e.g., bioreactor 501, 601, preconditioned with cell culture media comprised of αMEM+GlutaMAX (Gibco CAT #32561102) and 10% FBS (Hyclone CAT #5H30070.03). Donor 1 MSC may be cultured for 6.8 days and Donor 2 MSC may be cultured for 6.9 days. For Donor 1, n=1 (where n=number of machines or CESs, e.g., Quantum® Systems) for both overnight-coated and 10-minute ultrafiltration coated bioreactors. For Donor 2, n=1 for the overnight-coated CES, e.g., Quantum® System, and n=2 for the two 10-minute ultrafiltration coated CESs, e.g., Quantum® Systems.

Harvest yields for both Donor 1 Quantum® System runs with load with uniform suspension cell loading procedures may both be observed to be 1.93E+8 MSC. For example, overnight coating with load with uniform suspension cell loading procedure (LWUS) may yield 1.93E+8 MSC 1104; and 10-minute ultrafiltration coating with load with uniform suspension cell loading procedure (LWUS) may yield 1.93E+8 MSC 1108. To confirm efficacy of the 10-minute coating technique with other cell load protocols, an additional comparison may be made between Quantum® Systems loaded using the bulls-eye cell loading procedure (BullsEye Load). The Donor 1 MSC yield for the overnight coated with bulls-eye cell loading may be observed to be 2.23E+8 MSC 1112, and MSC yield for the 10-minute ultrafiltration coat with bulls-eye cell loading procedure (BullsEye Load) may be observed to be 2.15E+8 MSC 1116. The Donor 2 MSC expansion may be observed to yield 1.91E+8 MSC 1120 for the overnight coated Quantum® System (n=1) with load with uniform suspension cell loading procedure (LWUS), and 2.05E+8 MSC 1124 and 1.93E+8 MSC 1128, respectively, for the two runs of 10-minute ultrafiltration coated Quantum® Systems (n=2) with load with uniform suspension cell loading procedure (LWUS).

In other examples, fibronectin (FN) may be used as a coating agent with similar methods and systems as described above. Example results when using fibronectin include: cell yields for 10-minute ultrafiltration FN coated Quantum® Systems may be observed to be in the range of 40% to 50% of overnight-coated harvests for a substantially same cell load.

Example 2

Figure 12A:
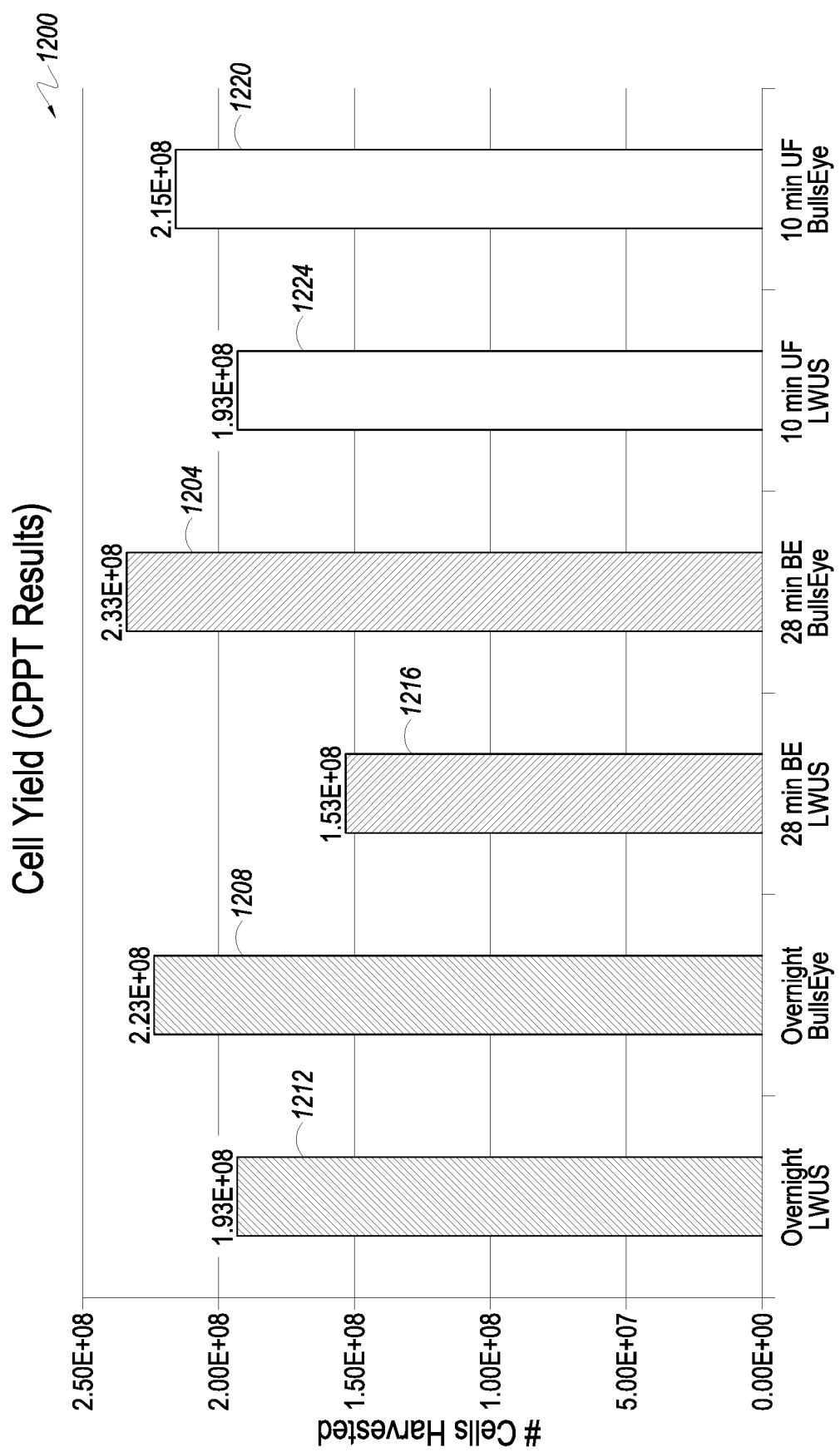
FIG. 12A illustrates example results of expanding cells using various coating and cell loading procedures in accordance with embodiments of the present disclosure.
Figure 12B:
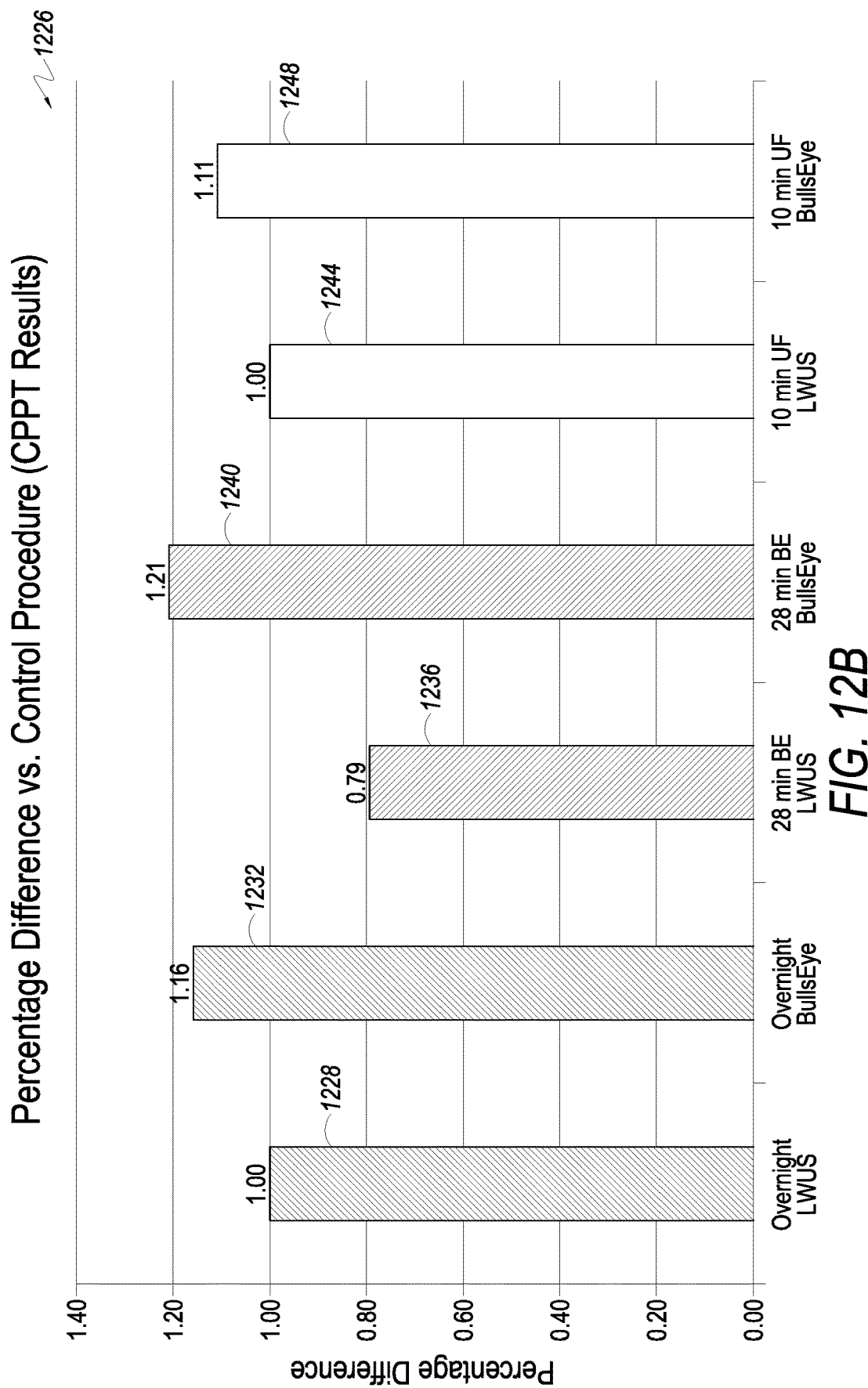
FIG. 12B depicts example results of expanding cells using various coating and cell loading procedures in accordance with embodiments of the present disclosure.

Example results of expanding cells by coating a cell growth surface of a cell expansion system, such as CES 500 (FIG. 5) and/or CES 600 (FIG. 6), for example, with various coating and cell loading procedures are illustrated in FIGS. 12A and 12B. For example, such cell growth surface coating and resulting cell expansion may use the Quantum® Cell Expansion System manufactured by Terumo BCT, Inc. in Lakewood, Colorado. FIGS. 12A and 12B illustrate example results of coating a cell growth surface through a coating procedure with ultrafiltration, e.g., about 10-minute ultrafiltration coating procedure (10 min UF), versus coating using an overnight circulating coating procedure or a bulls-eye coating procedure, e.g., a 28-minute modified bulls-eye coating procedure (28 min BE). For example, a 10-minute positive ultrafiltration coating procedure may be used. In such procedures, 5 million MSCs may be loaded into the system, and 25 mL of a cryoprecipitate solution may be used for coating the cell growth surface of a hollow fiber bioreactor. The 28-minute bulls-eye coating time period used to coat the hollow fiber(s), e.g., fiber(s) 812 (FIG. 8B), may be divided into seven (7) different time periods, each division being four (4) minutes long. During each 4-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be about −300 mL/min, 250 mL/min, −200 mL/min, 150 mL/min, −100 mL/min, 50 mL/min, and −25 mL/min. The results from using these coating procedures with cryoprecipitate (CPPT) may be as shown in FIGS. 12A and 12B.

FIGS. 12A and 12B illustrate example results of using CPPT to coat the cell growth surface of a plurality of hollow fibers using various coating and cell loading procedures, and combinations thereof. As shown in graph 1200 of FIG. 12A, the 28-minute bulls-eye coating procedure (28 min BE) with bulls-eye cell loading procedure (BullsEye) may outperform the following procedures: the 28-minute bulls-eye coating procedure (28 min BE) with load with uniform suspension cell loading procedure (LWUS); the overnight (o/n) coating procedure with load with uniform suspension cell loading procedure (LWUS); the overnight coating procedure with bulls-eye cell loading procedure (BullsEye); the 10-minute ultrafiltration coating procedure (10 min UF) with load with uniform suspension cell loading procedure (LWUS); and the 10-minute ultrafiltration coating procedure (10 min UF) with bulls-eye cell loading procedure (BullsEye).

As shown in graph 1200 of FIG. 12A, the 28-minute bulls-eye coating procedure (28 min BE) with bulls-eye cell loading procedure (BullsEye) may yield 2.33E+08 cells 1204 while the overnight coating procedure with bulls-eye cell loading procedure (BullsEye) may yield 2.23E+08 cells 1208. The overnight coating procedure with load with uniform suspension cell loading procedure (LWUS) may yield 1.93E+08 cells 1212, while the 28-minute bulls-eye coating procedure with load with uniform suspension cell loading procedure (LWUS) may yield 1.53E+08 cells 1216. A 10-minute ultrafiltration procedure (10 min UF) with bulls-eye cell loading procedure (BullsEye) may result in 2.15E+08 cells 1220, while a 10-minute ultrafiltration coating procedure (10 min UF) with load with uniform suspension cell loading procedure (LWUS) may yield 1.93E+08 cells 1224.

These example yields are compared in FIG. 12B. Graph 1226 of FIG. 12B illustrates a percentage difference versus control procedure using cryoprecipitate (CPPT) as a coating agent in various coating procedures and cell loading procedures, and combinations thereof. As shown in graph 1226 of FIG. 12B, compared to the overnight coating procedure with load with uniform suspension cell loading procedure (LWUS) 1228, the overnight coating procedure with bulls-eye cell loading procedure (BullsEye) may yield 16% 1232 more cells; the 28-minute bulls-eye coating procedure with load with uniform suspension cell loading procedure (LWUS) may yield 21% 1236 fewer cells; the 28-minute bulls-eye coating procedure (28 min BE) with bulls-eye cell loading procedure (BullsEye) may yield 21% 1240 more cells; the 10-minute ultrafiltration coating procedure (10 min UF) with load with uniform suspension cell loading procedure (LWUS) may yield substantially the same number 1244 of cells; and the 10-minute ultrafiltration coating procedure (10 min UF) with bulls-eye cell loading procedure (BullsEye) may yield 11% 1248 more cells.

Example 3

Figure 13A:
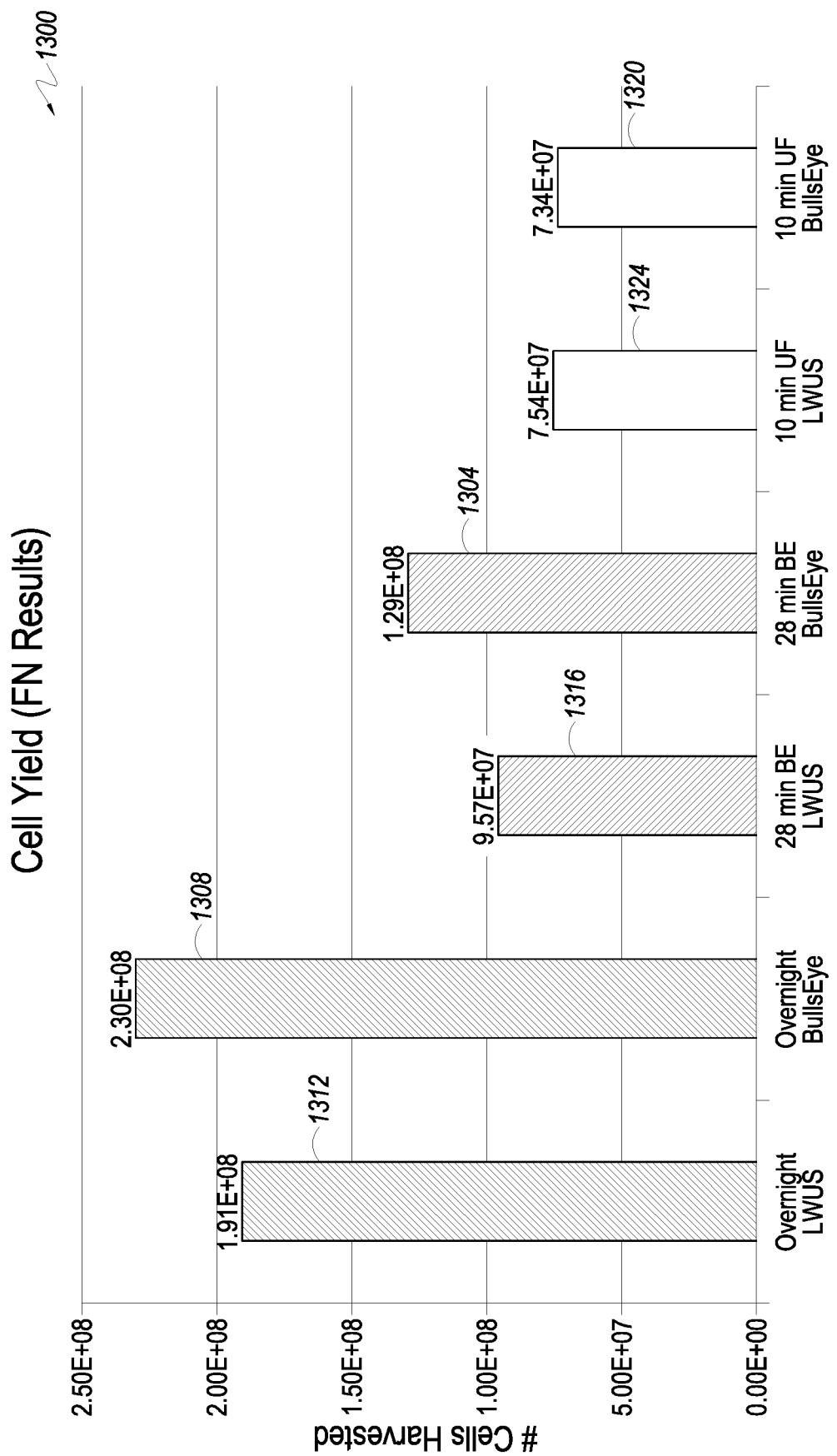
FIG. 13A illustrates example results of expanding cells using various coating and cell loading procedures in accordance with embodiments of the present disclosure.
Figure 13B:
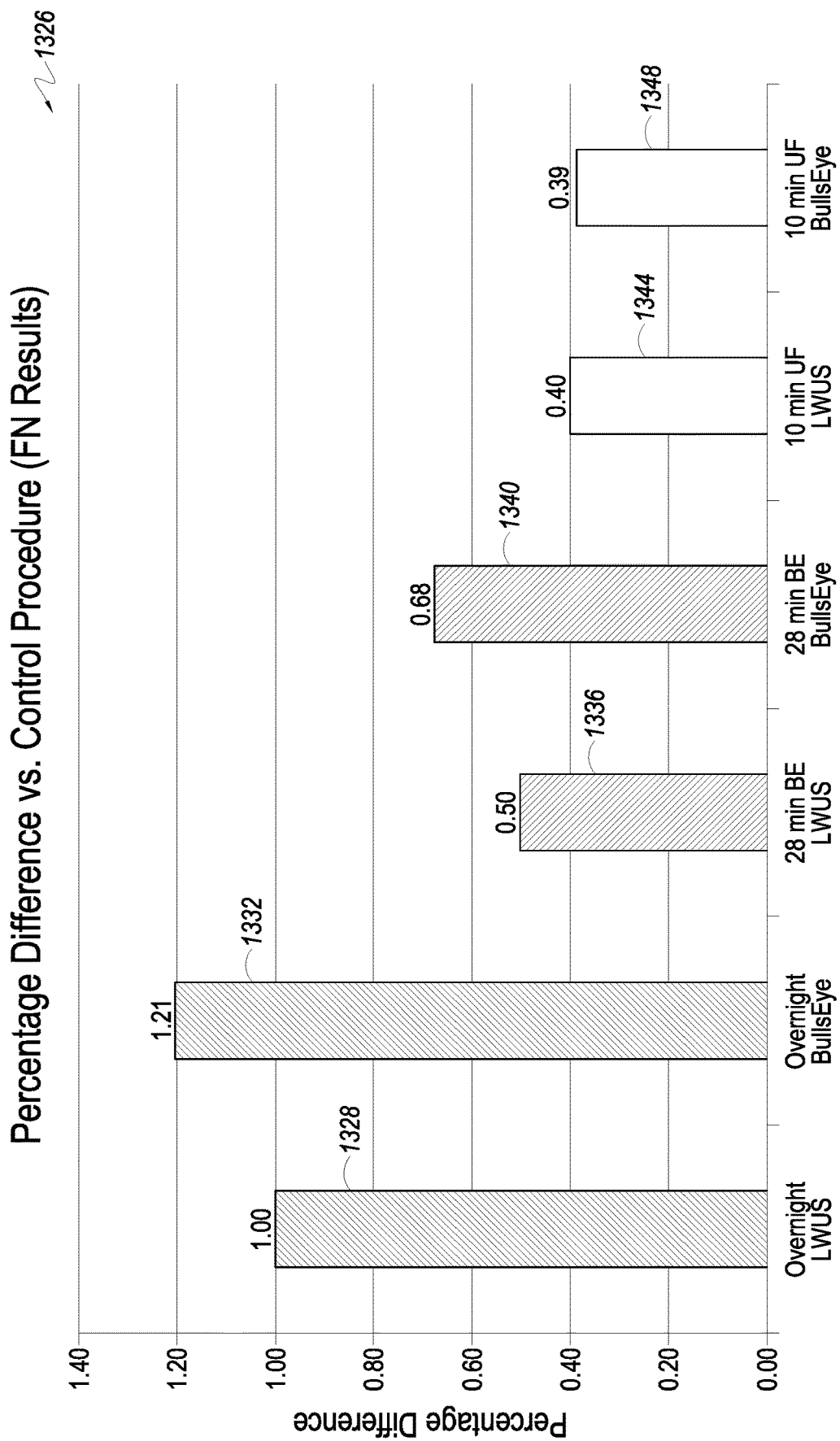
FIG. 13B depicts example results of expanding cells using various coating and cell loading procedures in accordance with embodiments of the present disclosure.

Example results of expanding cells by coating a cell growth surface of a cell expansion system, such as CES 500 (FIG. 5) and/or CES 600 (FIG. 6), for example, with various coating and cell loading procedures are illustrated in FIGS. 13A and 13B. For example, such cell growth surface coating and resulting cell expansion may use the Quantum® Cell Expansion System manufactured by Terumo BCT, Inc. in Lakewood, Colorado. FIGS. 13A and 13B illustrate example results of coating a cell growth surface through a coating procedure with ultrafiltration, e.g., about 10-minute ultrafiltration coating procedure (10 min UF), versus coating using an overnight circulating coating procedure or a bulls-eye coating procedure, e.g., a 28-minute modified bulls-eye coating procedure (28 min BE). For example, a 10-minute positive ultrafiltration coating procedure may be used. In such procedures, 5 million MSCs may be loaded into the system, and a 5 mg fibronectin (FN) solution may be used for coating the cell growth surface of a hollow fiber bioreactor. In an embodiment, such 5 mg FN solution may be circulated at 20 mL/minute. In the Quantum® System, such 5 mg FN solution may be circulated at 20 mL/minute in the 189 mL IC loop, according to an embodiment. The 28-minute bulls-eye coating time period used to coat the hollow fibers, e.g., fiber(s) 812 (FIG. 8B), may be divided into seven (7) different time periods, each division being four (4) minutes long. During each 4-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be about −300 mL/min, 250 mL/min, −200 mL/min, 150 mL/min, −100 mL/min, 50 mL/min, and −25 mL/min. The results from using these coating and cell loading procedures with fibronectin (FN) may be as shown in FIGS. 13A and 13B.

FIGS. 13A and 13B illustrate example results of using FN to coat the cell growth surface of a plurality of hollow fibers using various coating and cell loading procedures, and combinations thereof. As shown in graph 1300 of FIG. 13A, the overnight coating procedure with bulls-eye cell loading procedure (BullsEye) may outperform the following: the overnight coating procedure with load with uniform suspension cell loading procedure (LWUS); the 28-minute bulls-eye coating procedure (28 min BE) with load with uniform suspension cell loading procedure (LWUS); the 28-minute bulls-eye coating procedure (28 min BE) with bulls-eye cell loading procedure (BullsEye); the 10-minute ultrafiltration coating procedure (10 min UF) with load with uniform suspension cell loading procedure (LWUS); and the 10-minute ultrafiltration coating procedure (10 min UF) with bulls-eye cell loading procedure (BullsEye). As shown in graph 1300 of FIG. 13A, the 28-minute bulls-eye coating procedure (28 min BE) with bulls-eye cell loading procedure (BullsEye) may yield 1.29E+08 cells 1304, while the overnight coating procedure with bulls-eye cell loading procedure (BullsEye) may yield 2.30E+08 cells 1308. The overnight coating procedure with load with uniform suspension cell loading procedure (LWUS) may yield 1.91E+08 cells 1312, while the 28-minute bulls-eye coating procedure (28 min BE) with load with uniform suspension cell loading procedure (LWUS) may yield 9.57E+07 cells 1316. A 10-minute ultrafiltration coating procedure (10 min UF) with a bulls-eye cell loading procedure (BullsEye) may result in 7.34E+07 cells 1320, while a 10-minute ultrafiltration procedure (10 min UF) with load with uniform suspension cell loading procedure (LWUS) may yield 7.54E+07 cells 1324.

These example yields are compared in FIG. 13B. Graph 1326 of FIG. 13B illustrates a percentage difference versus control procedure using fibronectin (FN) as a coating agent in various coating procedures and cell loading procedures, and combinations thereof. As shown in graph 1326 of FIG. 13B, compared to the overnight coating procedure with load with uniform suspension cell loading procedure (LWUS) 1328, the overnight coating procedure with bulls-eye cell loading procedure (BullsEye) may yield 21% 1332 more cells; the 28-minute bulls-eye coating procedure with load with uniform suspension cell loading procedure (LWUS) may yield 50% 1336 fewer cells; the 28-minute bulls-eye coating procedure (28 min BE) with bulls-eye cell loading procedure (BullsEye) may yield 32% 1340 fewer cells; the 10-minute ultrafiltration coating procedure (10 min UF) with load with uniform suspension cell loading procedure (LWUS) may yield 60% 1344 fewer cells; and the 10-minute ultrafiltration coating procedure (10 min UF) with bulls-eye cell loading procedure (BullsEye) may yield 61% 1348 fewer cells.

Although specific features may be described in the examples, such examples are provided merely for illustrative and descriptive purposes. For example, while such examples may provide for the expansion of MSCs, other cell types may be used in other embodiments. It is noted that the example data are provided for illustrative purposes and are not intended to limit other embodiments, which may include different steps, parameters, materials, or other features. The present embodiments are not limited to the examples provided herein.

The embodiments of the disclosure may have one or more aspects, including, for example: a method of applying an agent to a cell growth surface in a cell expansion system, the method comprising: loading the agent into the cell expansion system; conducting a first wash to push the agent into a circulation loop; and conducting a second wash to cause the agent to coat the cell growth surface by ultrafiltration.

One or more of the above aspects, wherein the agent comprises cryoprecipitate.

One or more of the above aspects, wherein conducting the first wash further comprises: pushing the agent from an air removal chamber into the circulation loop.

One or more of the above aspects, wherein the circulation loop comprises an intracapillary loop.

One or more of the above aspects, wherein the cell expansion system comprises a hollow fiber bioreactor, and wherein the hollow fiber bioreactor comprises a plurality of hollow fibers.

One or more of the above aspects, wherein each of the plurality of hollow fibers comprises the cell growth surface.

One or more of the above aspects, wherein the agent coats the cell growth surface in about 60 minutes or less.

One or more of the above aspects, wherein the agent is in solution with a fluid, wherein, during the second wash, the fluid is actively moved from an intracapillary (IC) side of the hollow fiber bioreactor to an extracapillary (EC) side of the hollow fiber bioreactor by closing an IC outlet valve and opening an EC outlet valve, wherein the agent remains on at least a portion of the plurality of the hollow fibers while the fluid is pushed to the EC side from the IC side.

One or more of the above aspects, wherein the agent is hydrostatically deposited onto an inner wall of the IC side of each of the plurality of hollow fibers.

One or more of the above aspects, wherein the agent coats the cell growth surface in about 10 minutes or less.

The embodiments of the disclosure may have one or more aspects, also including, for example: a cell expansion system comprising: a bioreactor, wherein the bioreactor comprises a hollow fiber membrane; a first fluid flow path having at least opposing ends, wherein the first fluid flow path is fluidly associated with an intracapillary portion of the hollow fiber membrane; a processor; a memory, in communication with and readable by the processor, and containing a series of instructions that, when executed by the processor, cause the processor to: close a first outlet of the cell expansion system associated with the intracapillary portion of the hollow fiber membrane; load a coating solution into the cell expansion system, wherein the coating solution comprises a coating agent and a first fluid; and increase an inlet flow of a second fluid into the intracapillary portion of the hollow fiber membrane to push the first fluid through the intracapillary portion to the extracapillary portion of the hollow fiber membrane, wherein the coating agent coats a surface of the hollow fiber membrane.

One or more of the above aspects, wherein the memory further contains an instruction that, when executed by the processor, causes the processor to: open a second outlet of a second fluid path associated with the extracapillary portion of the hollow fiber membrane.

One or more of the above aspects, wherein the hollow fiber membrane comprises a cell growth surface, and wherein the coating agent coats the cell growth surface.

One or more of the above aspects, wherein the coating agent coats the cell growth surface through ultrafiltration.

One or more of the above aspects, wherein the coating occurs in less than about 60 minutes.

One or more of the above aspects, wherein the second fluid path is fluidly associated with an extracapillary circulation loop.

One or more of the above aspects, wherein the coating solution comprises cryoprecipitate and phosphate buffered saline.

One or more of the above aspects, wherein the memory further contains an instruction that, when executed by the processor, causes the processor to: set a stop condition for the inlet flow of the second fluid.

One or more of the above aspects, wherein the stop condition comprises a time period.

The embodiments of the disclosure may have one or more aspects, also including, for example: a method for rapidly coating a cell growth surface in a cell expansion system, the method comprising: priming the cell expansion system, wherein the cell expansion system comprises: a bioreactor, wherein the bioreactor comprises: a hollow fiber membrane having an intracapillary portion and an extracapillary portion, wherein the hollow fiber membrane comprises a plurality of hollow fibers, the plurality of hollow fibers comprising a cell growth surface; a first fluid flow path having a first inlet and a first outlet at at least opposing ends of the bioreactor, wherein the first fluid flow path is fluidly associated with the intracapillary portion of the hollow fiber membrane; a second fluid flow path having a second inlet and a second outlet, wherein the second fluid flow path is fluidly associated with the extracapillary portion of the hollow fiber membrane; a first connection port fluidly associated with the first fluid flow path; a first outlet valve fluidly associated with the first fluid flow path; a second outlet valve fluidly associated with the second fluid flow path; and a harvest bag; connecting a first bag containing a reagent for coating the cell growth surface of the plurality of hollow fibers; closing the first outlet valve; opening the second outlet valve; coating, through ultrafiltration, the cell growth surface with the reagent; connecting a second bag to the first connection port to introduce cells to the bioreactor; feeding the cells; connecting the harvest bag to the first fluid flow path to harvest the cells; and harvesting the cells into the harvest bag.

Embodiments further include one or more means for conducting the one or more above aspects.

Embodiments further include a system on chip, processor, application specific integrated circuit, field programmable gate array, or other control for executing the one or more above aspects.

While embodiments and examples have been illustrated and described, it is to be understood that the embodiments and examples are not limited to the precise configuration(s) and/or resource(s) described above. Various modifications, changes, and variations apparent to those skilled in the art may be made in the arrangement, operation, and details of the methods and systems of the present embodiments and examples disclosed herein without departing from the scope of the present claims.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" can mean A alone, B alone, C alone, A and B together, A and C together, B and C together, or A, B and C together.

It will be apparent to those skilled in the art that various modifications and variations may be made to the methods and structure of the present embodiments without departing from the scope of the claims. Thus, it should be understood that the embodiments are not to be limited to the specific examples given. Rather, the embodiments are intended to cover modifications and variations within the scope of the following claims and their equivalents.

What is claimed is:

1. A method of applying an agent to a cell growth surface in a cell expansion system, the method comprising:
   loading the agent and a fluid into the cell expansion system;
   conducting a first wash at a first inlet flow rate to push the agent and the fluid into a circulation loop;
   closing an outlet to the circulation loop; and
   after the closing, conducting a second wash at a second inlet flow rate higher than the first inlet flow rate to force a portion of the fluid through pores in a wall of the circulation loop and hydrostatically deposit the agent on the cell growth surface of the wall.

2. The method of claim 1, wherein the agent comprises cryoprecipitate.

3. The method of claim 1, wherein conducting the first wash further comprises: pushing the agent from an air removal chamber into the circulation loop.

4. The method of claim 3, wherein the circulation loop comprises an intracapillary loop.

5. The method of claim 4, wherein the cell expansion system comprises a hollow fiber bioreactor, and wherein the hollow fiber bioreactor comprises a plurality of hollow fibers.

6. The method of claim 5, wherein each of the plurality of hollow fibers comprises the cell growth surface.

7. The method of claim 5, wherein, during the second wash, the fluid is actively moved from an intracapillary (IC) side of the hollow fiber bioreactor to an extracapillary (EC) side of the hollow fiber bioreactor by closing an IC outlet valve and opening an EC outlet valve, and wherein the agent remains on at least a portion of the plurality of hollow fibers while the fluid is pushed to the EC side from the IC side.

8. The method of claim 7, wherein the agent is hydrostatically deposited onto an inner wall of the IC side of each of the plurality of hollow fibers.

9. The method of claim 1, wherein the conducting the second wash is performed for a duration ranging from 5 minutes to 60 minutes.

10. A method for rapidly coating a cell growth surface in a cell expansion system, the method comprising:
    priming the cell expansion system, wherein the cell expansion system comprises:
      a bioreactor, wherein the bioreactor comprises:
        a hollow fiber membrane having an intracapillary portion and an extracapillary portion, wherein the hollow fiber membrane comprises a plurality of hollow fibers, the plurality of hollow fibers comprising a cell growth surface;
        a first fluid flow path having a first inlet and a first outlet at at least opposing ends of the bioreactor, wherein the first fluid flow path is fluidly associated with the intracapillary portion of the hollow fiber membrane;
        a second fluid flow path having a second inlet and a second outlet, wherein the second fluid flow path is fluidly associated with the extracapillary portion of the hollow fiber membrane;
        a first connection port fluidly associated with the first fluid flow path;
        a first outlet valve fluidly associated with the first fluid flow path;
        a second outlet valve fluidly associated with the second fluid flow path; and
        a harvest bag;
    connecting a first bag containing a solution including a fluid and a reagent for coating the cell growth surface of the plurality of hollow fibers;
    closing the first outlet valve;
    opening the second outlet valve;
    flowing the solution into the first fluid flow path;
    conducting a first wash by flowing a second fluid into the first flow path at a first inlet flow rate;
    conducting a second wash by flowing the second fluid into the first flow path at a second inlet flow rate greater than the inlet first flow rate for a duration, thereby coating, through ultrafiltration, the cell growth surface with the reagent;
    connecting a second bag to the first connection port to introduce cells to the bioreactor; feeding the cells;
    connecting the harvest bag to the first fluid flow path to harvest the cells; and
    harvesting the cells into the harvest bag.

11. The method of claim 7, wherein the fluid includes phosphate buffered saline.

12. The method of claim 10, wherein the first fluid and the second fluid include phosphate buffered saline.

13. The method of claim 10, wherein the reagent includes cryoprecipitate (CPPT), fibronectin (FN), or a combination of CPPT and FN.

14. The method of claim 9, wherein the duration is 10 minutes or less.

15. The method of claim 1, wherein the second inlet flow rate ranges from 40 mL/min to 60 mL/min.

* * * * *